US012377423B2

(12) United States Patent
Kessler et al.

(10) Patent No.: US 12,377,423 B2
(45) Date of Patent: Aug. 5, 2025

(54) CENTRIFUGE SYSTEM FOR SEPARATING CELLS IN SUSPENSION

(71) Applicant: Pneumatic Scale Corporation, Cuyahoga Falls, OH (US)

(72) Inventors: Stephen B. Kessler, Princeton, MA (US); T. David Marro, Magnolia, MA (US)

(73) Assignee: PNEUMATIC SCALE CORPORATION, Cuyahoga Falls, OH (US)

( * ) Notice: Subject to any disclaimer, the term of this patent is extended or adjusted under 35 U.S.C. 154(b) by 0 days.

(21) Appl. No.: 18/396,084

(22) Filed: Dec. 26, 2023

(65) Prior Publication Data

US 2024/0131529 A1 Apr. 25, 2024

Related U.S. Application Data

(63) Continuation of application No. 17/587,691, filed on Jan. 28, 2022, now Pat. No. 11,878,311, which is a continuation of application No. 17/323,154, filed on May 18, 2021, which is a continuation of application No. 16/433,180, filed on Jun. 6, 2019, now Pat. No. 11,065,629, which is a continuation-in-part of application No. 16/003,659, filed on Jun. 8, 2018, now Pat. No. 11,033,911, and a continuation-in-part of application No. 15/886,382, filed on Feb. 1, 2018, now Pat. No. 10,384,216, said application No. 16/003,659 is a continuation of application No. 15/886,382, filed on Feb. 1, 2018, now Pat. No. 10,384,216, which is a continuation-in-part of application No. 14/698,995, filed on Apr. 29, 2015, now abandoned, which is a continuation of application No. 13/684,051, filed on Nov. 21, 2012, now Pat. No. 9,222,067.

(60) Provisional application No. 62/682,376, filed on Jun. 8, 2018, provisional application No. 61/562,438, filed on Nov. 21, 2011.

(51) Int. Cl.
| | | |
|---|---|---|
| B04B 11/04 | (2006.01) | |
| B04B 5/04 | (2006.01) | |
| B04B 11/02 | (2006.01) | |
| B04B 11/08 | (2006.01) | |

(52) U.S. Cl.
CPC ............. B04B 11/04 (2013.01); B04B 11/02 (2013.01); B04B 11/082 (2013.01); B04B 2005/0464 (2013.01)

(58) Field of Classification Search
CPC ........ B04B 11/04; B04B 1/06; B04B 5/0442; B04B 11/082; B04B 15/08; B04B 11/02; B04B 7/08; B04B 2005/0464; B04B 2005/045; C12M 25/06; C12M 33/10; C12M 47/02; B01D 21/262; B01D 2221/10

USPC ......... 494/12, 83, 41, 38, 43, 84–85, 56, 36, 494/25–26

See application file for complete search history.

(56) References Cited

U.S. PATENT DOCUMENTS

| | | | | |
|---|---|---|---|---|
| 3,145,713 A | * | 8/1964 | Latham, Jr. ......... | A61M 1/3693 422/534 |
| 3,409,213 A | * | 11/1968 | Latham, Jr. .............. | F16J 15/36 494/67 |
| 3,565,330 A | * | 2/1971 | Latham, Jr. ........... | B04B 5/0442 494/67 |
| 3,785,549 A | * | 1/1974 | Latham, Jr. ............... | B04B 7/00 494/85 |
| 4,140,268 A | * | 2/1979 | Lacour ..................... | B04B 7/08 494/81 |
| 4,300,717 A | * | 11/1981 | Latham, Jr. ......... | A61M 1/3693 494/41 |
| 4,668,214 A | * | 5/1987 | Reeder ................ | A61M 1/3693 494/37 |
| 4,684,361 A | * | 8/1987 | Feldman .................. | B04B 7/08 277/358 |
| 4,692,136 A | * | 9/1987 | Feldman ............... | B04B 5/0442 277/358 |
| 4,767,396 A | * | 8/1988 | Powers .................... | B04B 9/12 494/60 |
| 4,795,419 A | * | 1/1989 | Yawn ....................... | B04B 7/08 494/84 |
| 4,859,333 A | * | 8/1989 | Panzani .............. | A61M 1/3696 210/360.2 |
| 4,879,031 A | * | 11/1989 | Panzani ................ | B04B 5/0442 210/360.2 |
| 4,889,524 A | * | 12/1989 | Fell ....................... | G01L 9/0004 494/12 |
| 4,943,273 A | * | 7/1990 | Pages ....................... | B04B 7/08 494/64 |
| 4,983,158 A | * | 1/1991 | Headley ................ | B04B 5/0442 494/64 |

(Continued)

FOREIGN PATENT DOCUMENTS

| | | | | |
|---|---|---|---|---|
| CA | 2890542 A1 | * | 5/2014 | ......... A61M 1/3693 |
| CN | 112074307 B | * | 1/2024 | ......... A61M 1/3403 |

(Continued)

*Primary Examiner* — Charles Cooley

(74) *Attorney, Agent, or Firm* — Ralph E. Jocke; Walker & Jocke

(57) ABSTRACT

An apparatus for separating cell suspension material into centrate and concentrate, includes a single use structure (178, 240, 250) releasably positioned in a cavity in a solid wall rotatable centrifuge bowl (172). The bowl and portions of single use structure rotate about an axis (174). A stationary inlet feed tube (184), a centrate discharge tube (212) and a concentrate discharge tube (230) extend along the axis of the rotating single use structure. A centrate centripetal pump (208) is in fluid connection with the centrate discharge tube. A concentrate centripetal pump (216) is in fluid connection with the concentrate discharge tube. A controller (274) operates responsive to sensors (264, 270) in respective centrate and concentrate discharge lines (262, 268), to control flow rates of a concentrate pump (272) and a centrate pump (266) to produce output flows of cell concentrate and generally cell free centrate.

28 Claims, 31 Drawing Sheets

(56) References Cited

U.S. PATENT DOCUMENTS

| | | | | |
|---|---|---|---|---|
| 5,045,048 A * | 9/1991 | Kaleskas | B04B 5/0442 | 277/393 |
| 5,100,372 A * | 3/1992 | Headley | B04B 7/12 | 494/64 |
| 5,141,486 A * | 8/1992 | Antwiler | A61M 1/3696 | 494/35 |
| 5,312,319 A * | 5/1994 | Salter | B04B 9/12 | 269/45 |
| 5,405,308 A * | 4/1995 | Headley | B04B 5/0407 | 494/67 |
| 5,478,479 A * | 12/1995 | Herrig | A61M 1/3696 | 210/94 |
| 5,494,592 A * | 2/1996 | Latham, Jr. | A61M 1/30 | 494/37 |
| 5,505,683 A * | 4/1996 | Geringer | B04B 7/00 | 494/12 |
| 5,514,070 A * | 5/1996 | Pages | A61M 1/3696 | 494/64 |
| 5,643,193 A * | 7/1997 | Papillon | A61M 1/3696 | 604/6.07 |
| 5,733,253 A * | 3/1998 | Headley | A61M 1/3693 | 494/23 |
| 5,882,289 A * | 3/1999 | Sakota | B04B 7/08 | 494/67 |
| 5,919,125 A * | 7/1999 | Berch | B04B 7/08 | 494/67 |
| 6,241,649 B1 * | 6/2001 | Zanella | B04B 11/04 | 494/10 |
| 6,352,499 B1 * | 3/2002 | Geigle | B04B 5/0442 | 494/37 |
| 6,716,151 B2 * | 4/2004 | Panzani | A61M 1/3696 | 494/10 |
| 6,743,192 B1 * | 6/2004 | Sakota | A61M 1/3696 | 604/4.01 |
| 7,211,037 B2 * | 5/2007 | Briggs | A61M 1/3693 | 494/67 |
| 7,332,125 B2 * | 2/2008 | Cianci | B04B 5/0442 | 604/4.01 |
| 8,454,548 B2 * | 6/2013 | Ohashi | A61M 1/0209 | 604/4.01 |
| 8,647,289 B2 * | 2/2014 | Pages | A61M 1/3607 | 604/4.01 |
| 8,808,978 B2 * | 8/2014 | Pages | B04B 15/06 | 435/283.1 |
| 8,834,402 B2 * | 9/2014 | Pages | A61M 1/3693 | 604/4.01 |
| 9,302,042 B2 * | 4/2016 | Pagès | B01D 33/56 | |
| 9,370,615 B2 * | 6/2016 | Ragusa | B04B 5/0442 | |
| 9,669,152 B2 * | 6/2017 | Kimura | A61M 1/3696 | |
| 10,040,077 B1 * | 8/2018 | Sutton | B04B 15/08 | |
| 10,384,216 B1 * | 8/2019 | Sutton | C12M 25/06 | |
| 10,668,207 B2 * | 6/2020 | Kasper | A61M 1/38 | |
| 10,683,478 B1 * | 6/2020 | Ma | C12M 23/14 | |
| 11,033,911 B2 * | 6/2021 | Kessler | B04B 11/082 | |
| 11,065,629 B2 * | 7/2021 | Kessler | B04B 5/0442 | |
| 11,878,311 B2 * | 1/2024 | Kessler | C12M 23/28 | |
| 11,878,312 B2 * | 1/2024 | Kessler | B04B 11/02 | |
| 11,957,998 B2 * | 4/2024 | Kessler | B04B 7/08 | |
| 2001/0027156 A1 * | 10/2001 | Egozy | B04B 5/0442 | 494/67 |
| 2002/0032112 A1 * | 3/2002 | Pages | B04B 7/08 | 494/36 |
| 2002/0099319 A1 * | 7/2002 | Saito | A61M 1/362266 | 604/6.04 |
| 2002/0142909 A1 * | 10/2002 | Sakota | A61M 1/3696 | 494/67 |
| 2003/0125182 A1 * | 7/2003 | Headley | B04B 5/0428 | 494/45 |
| 2003/0181305 A1 * | 9/2003 | Briggs | A61M 1/3696 | 494/67 |
| 2004/0112808 A1 * | 6/2004 | Takagi | A61M 1/3696 | 210/97 |
| 2005/0054508 A1 * | 3/2005 | Panzani | A61M 1/367 | 210/745 |
| 2006/0199720 A1 * | 9/2006 | Juan | B04B 5/0442 | 494/64 |
| 2006/0287628 A1 * | 12/2006 | Hirabuki | A61M 1/308 | 604/6.01 |
| 2007/0213191 A1 * | 9/2007 | Chammas | B04B 7/00 | 494/67 |
| 2008/0124700 A1 * | 5/2008 | Fortini | A61M 1/3693 | 435/2 |
| 2008/0128367 A1 * | 6/2008 | Rochat | B04B 11/082 | 210/782 |
| 2008/0132397 A1 * | 6/2008 | Rochat | B04B 5/0442 | 494/45 |
| 2008/0153686 A1 * | 6/2008 | Rochat | B04B 5/0442 | 494/45 |
| 2008/0264841 A1 * | 10/2008 | Rochat | B04B 11/082 | 210/120 |
| 2009/0050579 A1 * | 2/2009 | Rochat | B04B 15/12 | 210/772 |
| 2009/0065424 A1 * | 3/2009 | Rochat | B04B 11/06 | 210/512.3 |
| 2009/0259163 A1 * | 10/2009 | Pages | A61M 1/3621 | 604/6.02 |
| 2010/0048373 A1 * | 2/2010 | Rochat | A61M 1/3693 | 494/41 |
| 2010/0167388 A1 * | 7/2010 | Kessler | C12M 33/10 | 435/308.1 |
| 2013/0012371 A1 * | 1/2013 | Marro | B04B 13/00 | 494/6 |
| 2013/0089917 A1 * | 4/2013 | Kessler | B04B 11/04 | 435/308.1 |
| 2013/0331252 A1 * | 12/2013 | Brunner | B04B 7/08 | 494/38 |
| 2014/0045672 A1 * | 2/2014 | Galavotti | B04B 11/06 | 494/44 |
| 2015/0231315 A1 * | 8/2015 | Kimura | A61M 1/3696 | 604/6.02 |
| 2015/0284671 A1 * | 10/2015 | Kessler | C12M 33/10 | 435/308.1 |
| 2017/0296718 A1 * | 10/2017 | Kimura | B04B 5/0442 | |
| 2019/0283044 A1 * | 9/2019 | Kessler | B04B 11/082 | |
| 2019/0283045 A1 * | 9/2019 | Kessler | B04B 11/082 | |
| 2021/0205734 A1 * | 7/2021 | Kessler | B04B 7/08 | |
| 2021/0268519 A1 * | 9/2021 | Kessler | B04B 11/02 | |
| 2022/0143627 A1 * | 5/2022 | Kessler | C12M 33/10 | |
| 2022/0152632 A1 * | 5/2022 | Kessler | C12M 23/28 | |
| 2022/0212207 A9 * | 7/2022 | Kessler | C12M 47/02 | |
| 2024/0131529 A1 * | 4/2024 | Kessler | C12M 47/02 | |
| 2024/0149280 A1 * | 5/2024 | Kessler | B04B 5/0442 | |
| 2024/0261708 A1 * | 8/2024 | Kessler | B04B 5/0442 | |
| 2025/0108386 A1 * | 4/2025 | Zhang | B04B 1/04 | |

FOREIGN PATENT DOCUMENTS

| | | | | |
|---|---|---|---|---|
| DE | 2712328 A | * | 10/1977 | B04B 5/0442 |
| EP | 257755 A | * | 3/1988 | A61M 1/3496 |
| EP | 608519 A2 | * | 8/1994 | A61M 1/3692 |
| EP | 657221 A1 | * | 6/1995 | B04B 7/00 |
| EP | 664159 A1 | * | 7/1995 | A61M 1/3693 |
| EP | 799645 A1 | * | 10/1997 | A61M 1/3693 |
| EP | 1057534 A1 | * | 12/2000 | B04B 5/0442 |
| EP | 1138392 A2 | * | 10/2001 | A61M 1/3693 |
| EP | 1683578 A1 | * | 7/2006 | A61M 1/3693 |
| EP | 1683579 A1 | * | 7/2006 | B04B 11/082 |
| EP | 1688183 A1 | * | 8/2006 | B04B 11/082 |
| EP | 1800754 A1 | * | 6/2007 | B04B 11/082 |
| EP | 1825874 A1 | * | 8/2007 | A61M 1/3692 |
| EP | 1825918 A1 | * | 8/2007 | B04B 1/00 |
| EP | 1911520 A1 | * | 4/2008 | A61M 1/3693 |
| EP | 2821144 A1 | * | 1/2015 | B04B 1/00 |
| EP | 3974009 A1 | * | 3/2022 | A61M 1/3693 |
| GB | 2181371 A | * | 4/1987 | B04B 5/0442 |
| JP | 59069166 A | * | 4/1984 | |
| JP | 07000857 A | * | 1/1995 | A61M 1/3692 |

(56) References Cited

FOREIGN PATENT DOCUMENTS

| JP | 09192215 A | * | 7/1997 | .......... A61M 1/3693 |
| JP | 2005081087 A | * | 3/2005 | ............... B04B 7/02 |
| WO | WO-9007383 A | * | 7/1990 | .......... A61M 1/3692 |
| WO | WO-9408721 A1 | * | 4/1994 | .......... A61M 1/3692 |
| WO | WO-9611747 A2 | * | 4/1996 | .......... A61M 1/3692 |
| WO | WO-9902269 A1 | * | 1/1999 | .......... B04B 5/0442 |
| WO | WO-03075983 A2 | * | 9/2003 | ......... A61K 41/0066 |
| WO | WO-2006079238 A1 | * | 8/2006 | .......... B04B 11/082 |
| WO | WO-2006081699 A1 | * | 8/2006 | .......... B04B 11/082 |
| WO | WO-2007071086 A1 | * | 6/2007 | .......... B04B 11/082 |
| WO | WO-2007098623 A1 | * | 9/2007 | .......... A61M 1/3692 |
| WO | WO-2009131659 A1 | * | 10/2009 | .......... B01D 21/262 |
| WO | WO-2011123371 A1 | * | 10/2011 | ............. B04B 11/02 |
| WO | WO-2014071365 A1 | * | 5/2014 | .......... A61M 1/3693 |
| WO | WO-2014112794 A1 | * | 7/2014 | ............. C12M 45/02 |
| WO | WO-2019236895 A1 | * | 12/2019 | .......... B01D 21/262 |
| WO | WO-2021188655 A1 | * | 9/2021 | .......... B01D 21/262 |

* cited by examiner

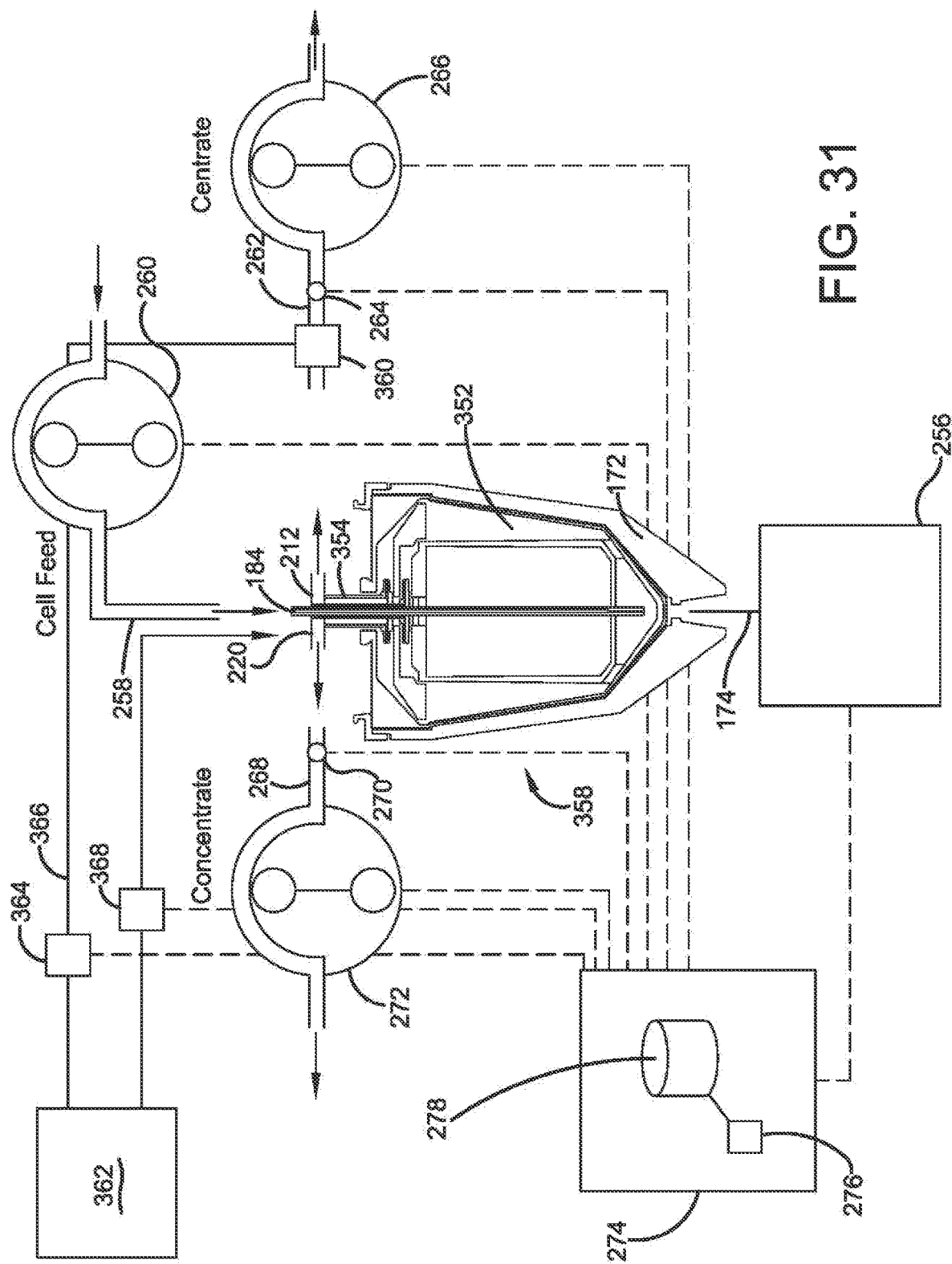

CENTRIFUGE SYSTEM FOR SEPARATING CELLS IN SUSPENSION

TECHNICAL FIELD

This disclosure relates to centrifugal processing of materials. Exemplary arrangements relate to devices for separating cells in suspension through centrifugal processing.

BACKGROUND

Devices and methods for centrifugal separation of cells in suspension are useful in many technological environments. Such systems may benefit from improvements.

SUMMARY

The exemplary arrangements described herein include apparatus and methods for centrifugal separation of cells in large-scale cell culture with a high cell concentration using pre-sterilized, single-use fluid path components. The exemplary centrifuges discussed herein may be solid wall centrifuges that use pre-sterilized, single-use components, and may be capable of processing cell suspensions, with high cell concentrations.

The exemplary arrangements use rotationally fixed feed and discharge components. Single use components include a flexible membrane mounted on a rigid frame including a core with an enlarged diameter. The single use components may further include at least one centripetal pump. The single use structures may be supported within a multiple use rigid bowl having an internal truncated cone shape. These structures permit the exemplary systems to maintain a sufficiently high angular velocity to create a settling velocity suited to efficiently processing highly concentrated cell culture streams. Features which minimize feed turbidity, and others which permit the continuous or semi-continuous discharge of cell concentrate, increase the overall production rate over the rate which can be achieved. Exemplary structures and methods provide for effective operation and reduce risks of contamination.

BRIEF DESCRIPTION OF THE DRAWINGS

FIG. 31 is a schematic view of an exemplary system for controlling a centrifuge system including centrate flow back pressure control.

DETAILED DESCRIPTION

Figure 1:
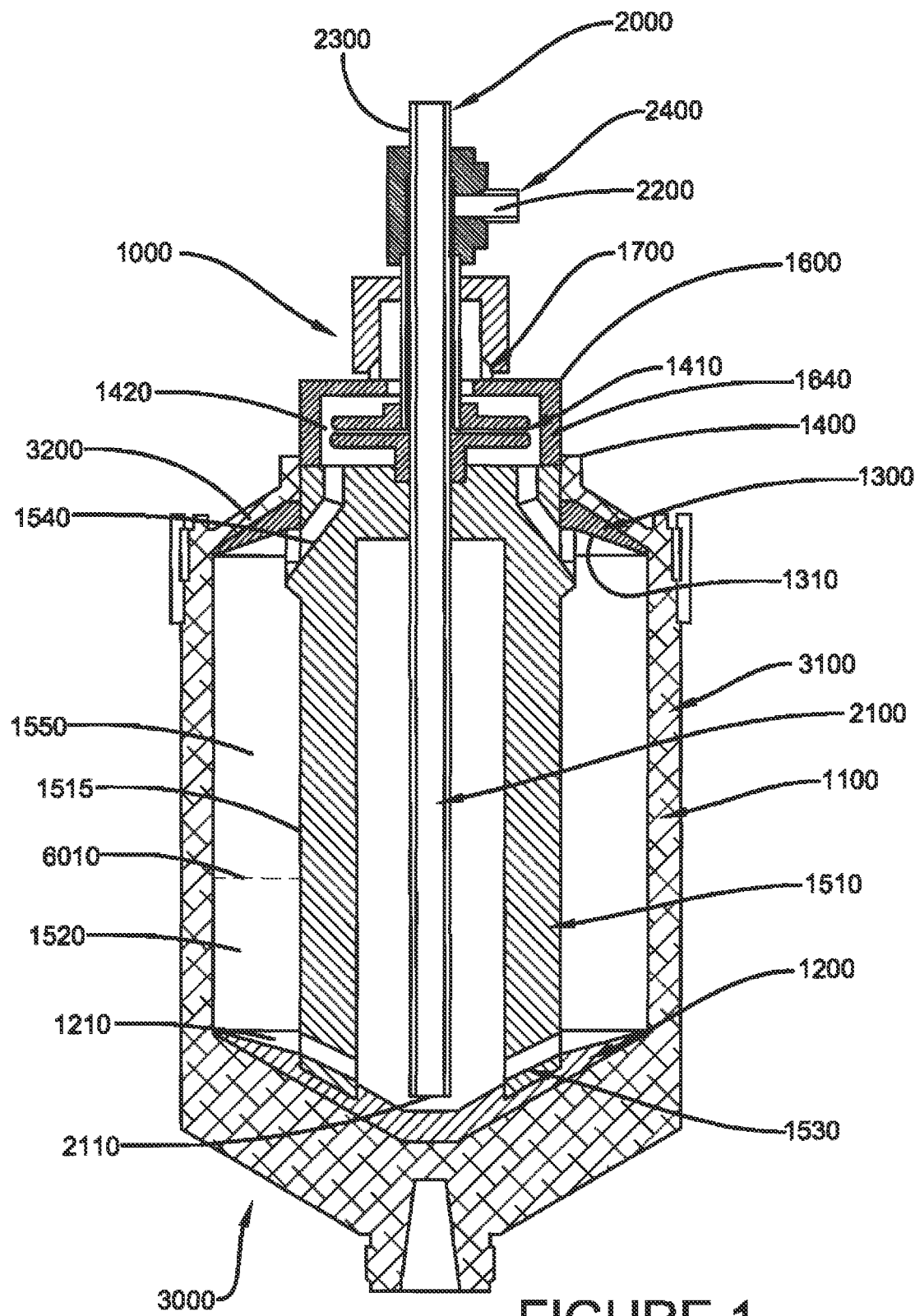
FIG. 1 is a schematic view of an exemplary arrangement of a centrifuge system including single use and multiple use components.

In the field of cell culture as applied to bio-pharmaceutical processes there exists a need to separate cells from fluid media such as fluid in which cells are grown. The desired product from the cell culture may be a molecular species that the cell excretes into the media, a molecular species that remains within the cell, or it may be the cell itself. At production scale, the initial stages of cell culture process typically take place in bioreactors, which may be operated in either batch or continuous mode. Variations such as repeated batch processes may be practiced as well. The desired product often must eventually be separated from other process components prior to final purification and product formulation. Cell harvest is a general term applied to these cell separations from other process components. Clarification is a term denoting cell separations in which a cell-free supernatant (or centrate) is the objective. Cell recovery is a term often applied to separations wherein a cell concentrate is the objective. The exemplary arrangements herein are directed to cell harvest separations in large-scale cell culture systems.

Methods for cell harvest separations include batch, intermittent, continuous and semi-continuous centrifugation, tangential flow filtration (TFF) and depth filtration. Historically, centrifuges for cell harvest of large volumes of cell culture at production scale are complex multiple use systems that require clean-in-place (CIP) and steam-in-place (SIP) technology to provide an aseptic environment to prevent contamination by microorganisms. At lab scale and for continuous cell harvest processes, smaller systems may be used. The UniFuge® which is a centrifuge system, manufactured by Pneumatic Scale Corporation, described in published application US 2010/0167388, the entire disclosure of which is incorporated herein by reference, successfully processes culture batches for cell harvest in the range of 3-30 liters/minute in quantities of up to about 2000 liters using intermittent processing. Also incorporated herein in their entirety are U.S. patent application Ser. No. 15/886,382 filed Feb. 1, 2018; and U.S. Pat. No. 9,222,067, which are also owned by Pneumatic Scale Corporation, the assignee of the present application. Intermittent processing generally requires periodically stopping both rotation of the centrifuge bowl and the feed flow in order to discharge concentrate. This approach usually works well with lower concentration, high viability cultures, in which large batches can be processed, and the cell concentrate discharged relatively quickly and completely.

There is sometimes a requirement to harvest cells from highly concentrated and/or low viability cell cultures, which contain a high concentration of cells and cell debris in the material feed, which are sometimes referred to as "high turbidity feeds." Such high turbidity feeds can slow down the processing rate in some centrifugal separation systems, because:

1. a slower feed flow rate is required to provide increased residence time in the centrifuge in order to separate small cell debris particles, and
2. the higher concentrations of both cells and cell debris may result in the bowl filling rapidly with cell concentrate, which requires the bowl to be stopped to discharge concentrate.

These combined factors may result in a reduced net throughput rate, and unacceptably long cell harvest processing times. In addition to the increased costs which may be associated with a longer processing time, increased time in the centrifuge may also result in a higher degree of product contamination and loss in the harvesting low viability cell cultures.

A high concentration of cell and cell debris in a material feed may also result in a cell concentrate with a very high viscosity. This may make it more difficult to completely discharge the cell concentrate from the centrifuge, even with a prolonged discharge cycle. In some cases, an additional buffer rinse cycle may be added to obtain a sufficiently complete discharge of concentrate. The need to make either or both of these adjustments to the discharge cycle further increases the processing time, which can make the challenges of processing a large volume of cell culture more complex and costly.

Scaling up the size of systems, by increasing the bowl size to increase the length of the feeding portion of the intermittent processing cycle is sometimes not practical because it also results in a proportionately longer discharge cycle for the cell concentrate. Another limitation that may preclude simple geometric scale-up is variation in scaling of the pertinent fluid dynamic factors. The maximum processing rate of any centrifuge depends on the settling velocity of the particles being separated. The settling velocity is given by a modification of Stokes' law defined by Equation 1:

$$v = \frac{\Delta p \cdot r \cdot d^2 \cdot \omega^2}{18 \cdot \mu} \quad \text{Equation 1}$$

where v=settling velocity, Δρ is solid-liquid density difference, d is particle diameter, r is radial position of the particle, ω is angular velocity, and μ is liquid viscosity. With respect to scale-up geometry, changing the radius of the bowl changes the maximum radial position r that particles can occupy. Therefore, if the other parameters in Equation 1 are held constant, an increase in bowl radius leads to an increase in average settling velocity and a gain in throughput for a given separation efficiency. However, as the radius increases it becomes more difficult to maintain the angular velocity of the bowl because of the increased material strength that may be required, and other engineering limitations. If a decrease in angular velocity is larger than the square root of the proportional increase in radius, then the average settling velocity and the gain in throughput (which is proportional to radius) both decline.

One of the engineering limitations that must be considered is that the angular velocity needed to rotate the larger bowl may not be practical to achieve because of the more massive and costly centrifuge drive platform that would be needed.

In addition if the angular velocity is held constant as the radius increases, the forces urging the cells toward the walls of the centrifuge also increase. When the bowl is rotated at sufficiently high angular velocity to create the desired processing efficiency, the walls of the container and the cells which accumulate there, experience added stress. As to the cells, this can cause cell damage by packing the cells to excessively high concentrations. Cell damage is a drawback in applications wherein cell viability needs to be maintained and can lead to contamination of products that are present in solution in the centrate. The higher viscosity resulting from excessively high cell concentrations is also sometimes a drawback for complete discharge of the cell concentrate.

Exemplary arrangements include apparatus and methods for continuous or semi-continuous centrifugal separation of low viability cell suspension cultures containing a high concentration of cells and cell debris, at a rate suitable for processing large volumes of cell suspensions on a commercial scale. Some exemplary centrifuges are of pre-sterilized, single-use designs and are capable of processing such cell suspensions at flow rates exceeding 20 liters per minute. This flow capacity enables total run times in the range of 2 to 3 hours for a 2000 liter bioreactor. Exemplary arrangements of the single-use centrifuge systems may be capable of processing about 300 to 2,000 liters of fluid while operating at a rate of about 2 to 40 liters per minute.

FIG. 1 discloses a single use centrifuge structure 1000. The centrifuge structure 1000 includes a core structure 1500 (best shown in FIG. 3) comprising a core 1510, upper flanges 1300, lower flanges 1200, and a flexible liner 1100 sealed to both an upper flange 1300 and a lower flange 1200. The centrifuge structure 1000 also includes a centripetal pump 1400, comprising a pair of stationary paring disks 1410 in a rotating pump chamber 1420, and a rotating mechanical seal 1700.

Centrifuge structure 1000 also includes a feed/discharge assembly 2000. The assembly 2000 comprises a plurality of concentric tubes about the rotational axis 1525 (labeled in FIG. 12) of the centrifuge 1000. The innermost portion of feed/discharge assembly 2000 includes a feed tube 2100. A plurality of additional tubes concentrically surround the feed tube 2100, and may include tubes or fluid pathways to permit centrate discharge 2200, concentrate discharge 2500 (see, for example, FIG. 12), or diluent feed 5000 (see, for example, FIG. 12). Each portion of the feed/discharge connection may be in fluid connection with a portion of the interior of the centrifuge 1000, and a collection or feed chamber (not shown) via appropriate fluid connections, and may include further tubes which are in fluid connection with the concentric tubes to remove or add the centrate, concentrate, or diluents from or to the system.

The upper and lower flanges 1300, 1200, as illustrated in FIG. 1, comprise conical bowls, axially aligned with and concave toward the core 1510. Core 1510 comprises a generally cylindrical body with a hollow cylindrical center large enough to accept feed tube 2100 having an axis 1525 (labeled in FIG. 12). The upper flange 1300, the core 1510 and the lower flange 1200 may be a unitary structure to provide a stronger support structure for flexible liner 1100 which is alternatively referred to herein as a membrane. In other arrangements, the core structure 1500 may be formed from a plurality of component parts. In further arrangements, the core 1510 and upper flange 1300 may comprise a single component, with a lower flange 1200 comprising a separate component, or the core 1510 and lower flange 1200 may comprise a single component with the upper flange 1300 comprising a separate component.

Figure 3:
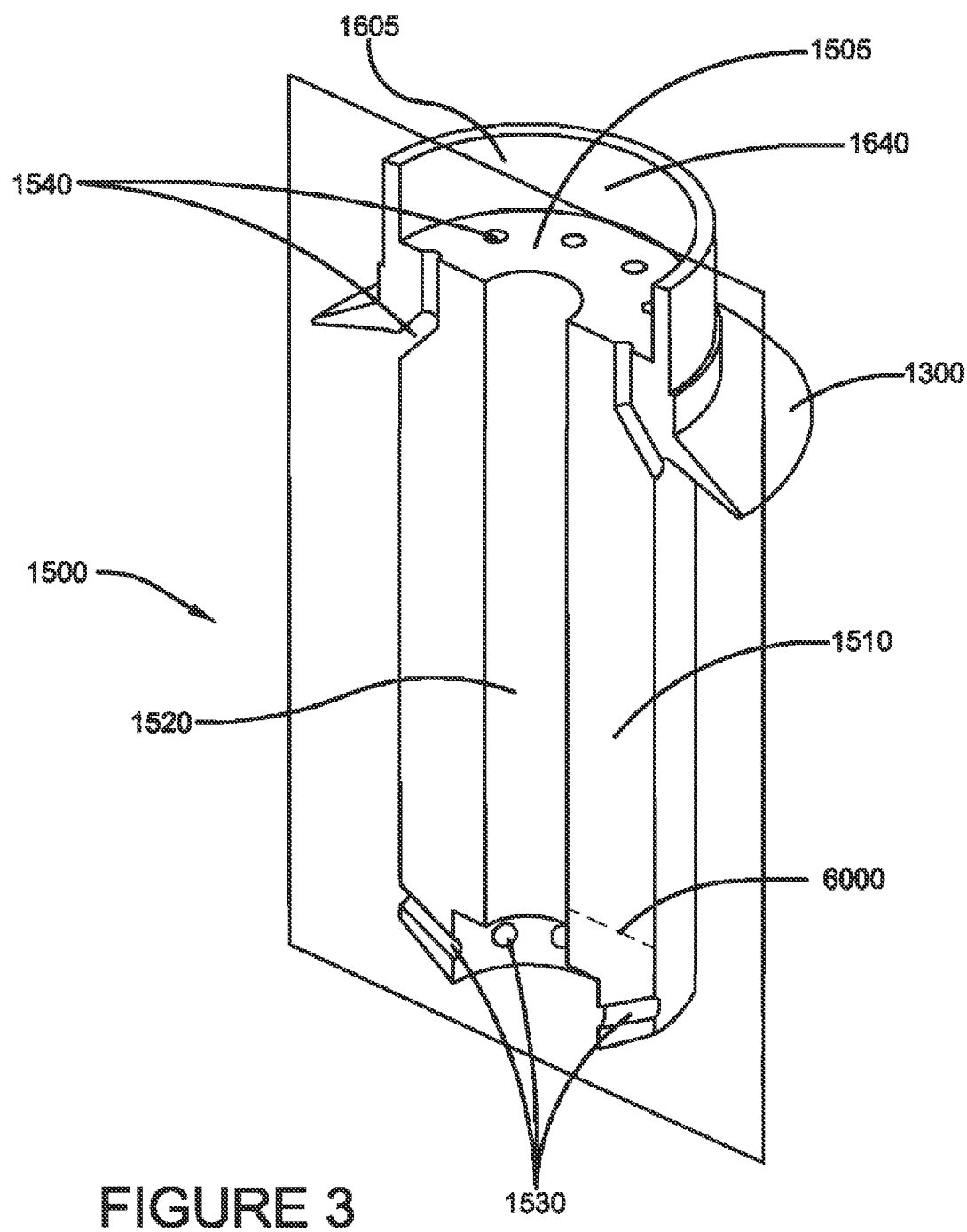
FIG. 3 is an isometric cutaway view of the core and upper flanges of the single use component of the arrangement the centrifuge system of FIG. 1.

An arrangement of a unitary core 1510 and upper flange 1300 is illustrated in FIG. 3. This unitary component would be joined to lower flange 1200 to create the internal supporting structure 1500 of the single use components of centrifuge 1000. This structure anchors the flexible liner 1100 around a fixed internal rigid or semi-rigid support structure 1500 at both the top and bottom. When the centrifuge system is in use, the flexible liner 1100 is also supported externally by the walls and cover of the multiple use structure 3000.

Figure 12:
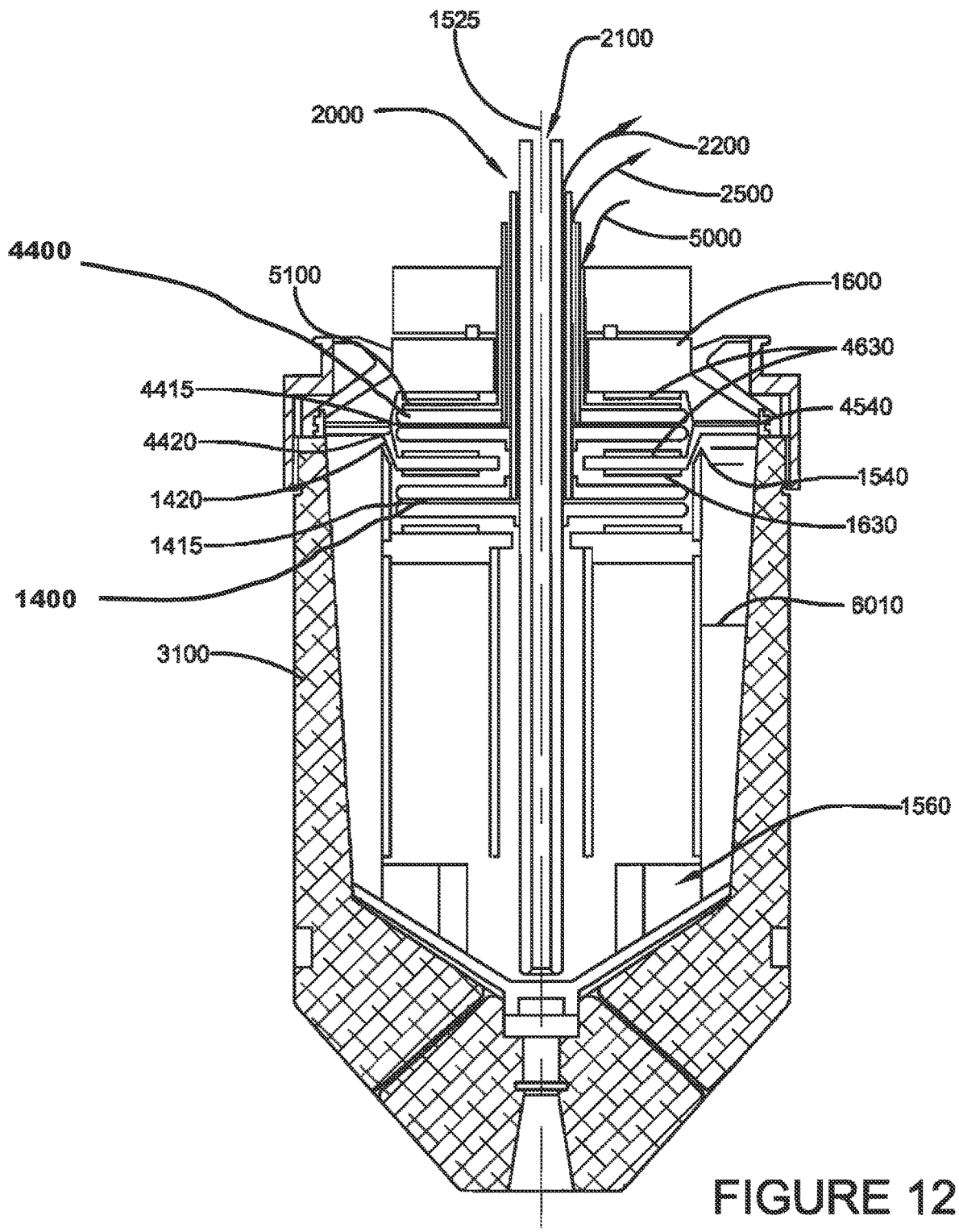
FIG. 12 is a schematic view of a continuous concentrate discharge centrifuge system with diluent injection.

The exemplary separation chamber 1550 is an open chamber which is roughly cylindrical in shape, bounded roughly by the exterior surface 1515 of the core 1510 and the flexible liner 1100, and by the upper surface 1210 of the lower flanges 1200 and the lower surface 1310 of the upper flanges 1300. The separation chamber 1550 is in fluid connection with the feed tube 2100 via holes 1530 extending from the central cavity 1520 of the core 1510 to the exterior surface 1515 of the core 1510. The separation chamber 1550 is also in fluid connection with the pump chamber 1420 via similar holes 1540 through the core structure 1500. In this example, holes 1540 angle upward, toward the pump chamber 1420, opening into the separation chamber 1550 just below the junction between the core 1510 and upper flanges 1300. As shown in FIG. 12, holes 1420 or 4420 may enter pump chambers at an angle other than upward, including horizontally or at a downward angle. In addition, in some arrangements holes 1420, 4420 may be replaced by slits, or gaps between accelerator fins.

FIG. 1 also shows a feed/discharge assembly 2000 which includes a feed tube carrier 2300, through which feed tube 2100 extends into the position shown in FIG. 3, close to the bottom of centrifuge structure 1000. In this position the feed tube 2100 can perform both feed and discharge functions without being moved. Shearing forces during the feeding process may be minimized by careful design of the gap between the nozzle 2110 of the feed tube 2100 and the upper surface 1210 of the lower flanges 1200, the diameter of the nozzle 2110 of the feed tube 2100, and the angular velocity of the centrifuge. U.S. Pat. No. 6,616,590, the disclosure of which is incorporated herein by reference in its entirety, describes how to select appropriate relationships to minimize the shearing forces. Other suitable feed tube designs which minimize the shearing forces associated with feeding a liquid cell culture into a rotating centrifuge which are known to those skilled in the art may also be used.

FIG. 1 further includes a centripetal pump 1400 for discharging centrate through a centrate discharge path 2200. In the exemplary arrangement shown in FIG. 1, the centrate pump 1400 is located above the upper flange 1300 in a pump chamber 1420. Pump chamber 1420 is a chamber defined by the upper surface 1505 of the core 1510 and the inner surfaces 1605, 1620 of a centrifuge cover 1600. The centrifuge cover 1600 may include cylindrical walls 1640 and a mating cap portion 1610 shaped like a generally circular disk (shown in FIG. 5). The centrifuge cover 1600 may be formed as a unitary body, or from separate components.

As discussed in more detail below, in other arrangements, the shape and position of the centrate pump chamber 1420 may vary. Chamber 1420 will generally be an axially symmetric chamber near the upper end of the core structure 1500 which is in fluid connection with the separation chamber 1550 via holes or slits 1530 which extend from adjacent the exterior of the core 1515 into the centrate pump chamber 1420. In some arrangements, as shown most clearly in FIGS. 11 and 12, centrate pump chamber 1420 may be located in a recess within chamber 1550.

Exemplary centrate pump 1400 comprises a pair of paring disks 1410. Paring disks 1410 are two thin circular disks (plates), which are axially aligned with the axis 1525 of core structure 1500. In the arrangement illustrated in FIGS. 1-5, paring disks 1410 are held stationary relative to the centrifuge structure 1000, and are separated from each other by a fixed gap 1415 (labeled 1415 in FIG. 10). The gap 1415 between the paring disks 1410 forms part of a fluid connection for removing centrate from the centrifuge 1000, which permits centrate to flow between the paring disks 1410 into a hollow cylindrical centrate discharge path 2200 concentric with and surrounding the feed tube carrier 2300, terminating in centrate outlet 2400.

The exemplary single use centrifuge structure 1000 is contained within a multiple use centrifuge structure 3000. The structure 3000 comprises a bowl 3100 with an axially centered cavity and a cover 3200. The walls of the cavity of the centrifuge bowl 3100 engagingly support the flexible liner 1100 of centrifuge structure 1000 during rotation of the centrifuge 1000. In order to do so, the external structure of the single use structure 1000 and the internal structure of the multiple use structure conform to each other. Similarly, the upper surface of upper flanges 1200, the exterior of an upper portion of core 1510, and a lower portion of the walls 1640 of the centrifuge cover 1600 conform to the inner surface of the multiple use bowl cover 3200, which is also adapted to provide support during rotation. Features of the multiple use bowl 3100 and bowl cover 3200, discussed in more detail below, are designed to ensure that shear forces do not tear the liner 1100 free from the single use centrifuge structure 1000. In some instances, an existing multiple use structure 3000 may be retrofitted for single use processing by selecting a conforming single use structure 1000. In other instances, the multiple use structure 3000 may be specially designed for use with single use structure inserts 1000.

Figure 2:
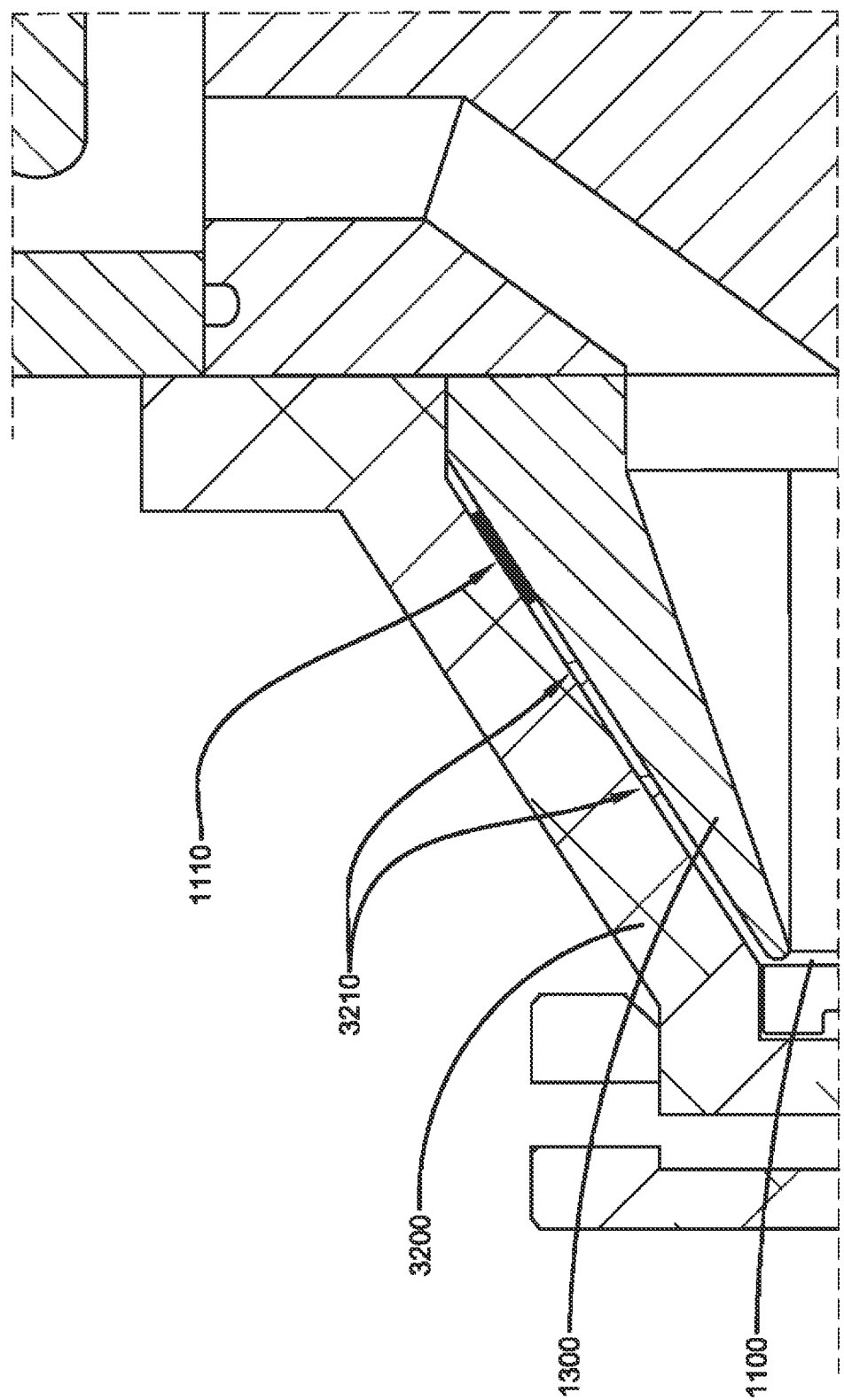
FIG. 2 is a close-up view of the upper flange area of the centrifuge of FIG. 1, which shows a method of sealing the flexible chamber material to the surface of the flange.

FIG. 2 shows a portion of an exemplary structure for upper flanges 1300, plastic liner 1100, and the cover 3200 of a multiple use centrifuge structure 3000 to illustrate sealing the flexible liner 1100 to the upper flanges 1300. The flexible liner 1100 may be a thermoplastic elastomer such as a polyurethane (TPU) or other stretchable, tough, non-tearing, bio-compatible polymer, while the upper and lower flanges 1300, 1200 may be fabricated from a rigid polymer such as polyetherimide, polycarbonate, or polysulfone. The flexible liner 1100 may comprise a thin sleeve, or envelope, which extends between and is sealed to the upper and lower flanges 1300, 1200, and forms the outer wall of separation chamber 1550. The composition of the liner 1100 and of the upper and lower flanges 1300, 1200, and core 1510 described herein are exemplary only. Those skilled in the art may substitute suitable materials with properties similar to those suggested which are, or may become, known.

A thermal bonding attachment process may be used to bond the dissimilar materials in the area shown in FIG. 2. The exemplary thermal bond 1110 is formed by preheating the flange material, placing the elastomeric polymer atop the heated flange, and applying heat and pressure to the elastomeric film liner 1100 at a temperature above the film's softening point. The plastic liner 1100 may be bonded to lower flange 1200 in the same manner. Although a thermal bond 1110 is described herein, it is merely exemplary. Other means of creating a similarly strong relatively permanent bond between the flexible film and the flange material may be substituted, such as by temperature, chemical, adhesive, or other bonding means.

The exemplary single-use components are pre-sterilized. During the removal of these components from their protective packaging and installation into a centrifuge, the thermal bonds 1110 maintain sterility within the single-use chamber. The stretchable flexible liner 1100 conforms to and engages the walls of the cavity of reusable bowl 3100 when in use. Reusable bowl 3100 provides sufficient support, and the flexible liner 1100 is sufficiently elastic, in an exemplary arrangement to permit the single use structure 1000 to withstand the increased rotational forces which are generated when the larger radius centrifuge 1000 is filled with a liquid cell culture or other cell suspension and is rotated with a sufficient angular velocity to reach a settling velocity that permits processing at a rate of about 2-40 liters a minute.

In addition to the thermal bond 1110, sealing ridges or "nubbins" 3210 may be present on bowl cover 3200 to compress the thermoplastic elastomeric film against the rigid upper flanges 1300, forming an additional seal. The same compression seals may also be used at the bottom of the bowl 3100 to seal the thermoplastic elastomeric film against the rigid lower flanges 1200. These compression seals support the thermal bonded areas 1110, by isolating them from shearing forces created by the hydrostatic pressure that develops during centrifugation when the chamber is filled with liquid. The combination of the thermal bond 1110 and the compression nubbin 3210 seals has been tested at 3000×g, which corresponds to a hydrostatic pressure of 97 psi at the bowl wall. In some exemplary arrangements, the lining is sufficiently thick and compressible to permit the nubbins 3210 to compress and grip the flexible liner 1100 yet minimize the risk of tearing near the thermal bond 1110 or compression nubbins 3210. In one example arrangement, a flexible TPU liner 0.010 inch thick sealed without tearing or leaking.

An exemplary arrangement corresponding to the illustrations of FIGS. 1-2 has been tested within a bowl that was 5.5 inches in diameter. At 2000×g it had a hydraulic capacity >7 liters/min and successfully separated mammalian cells to 99% efficiency at a rate of 3 liter/min.

Figure 10:
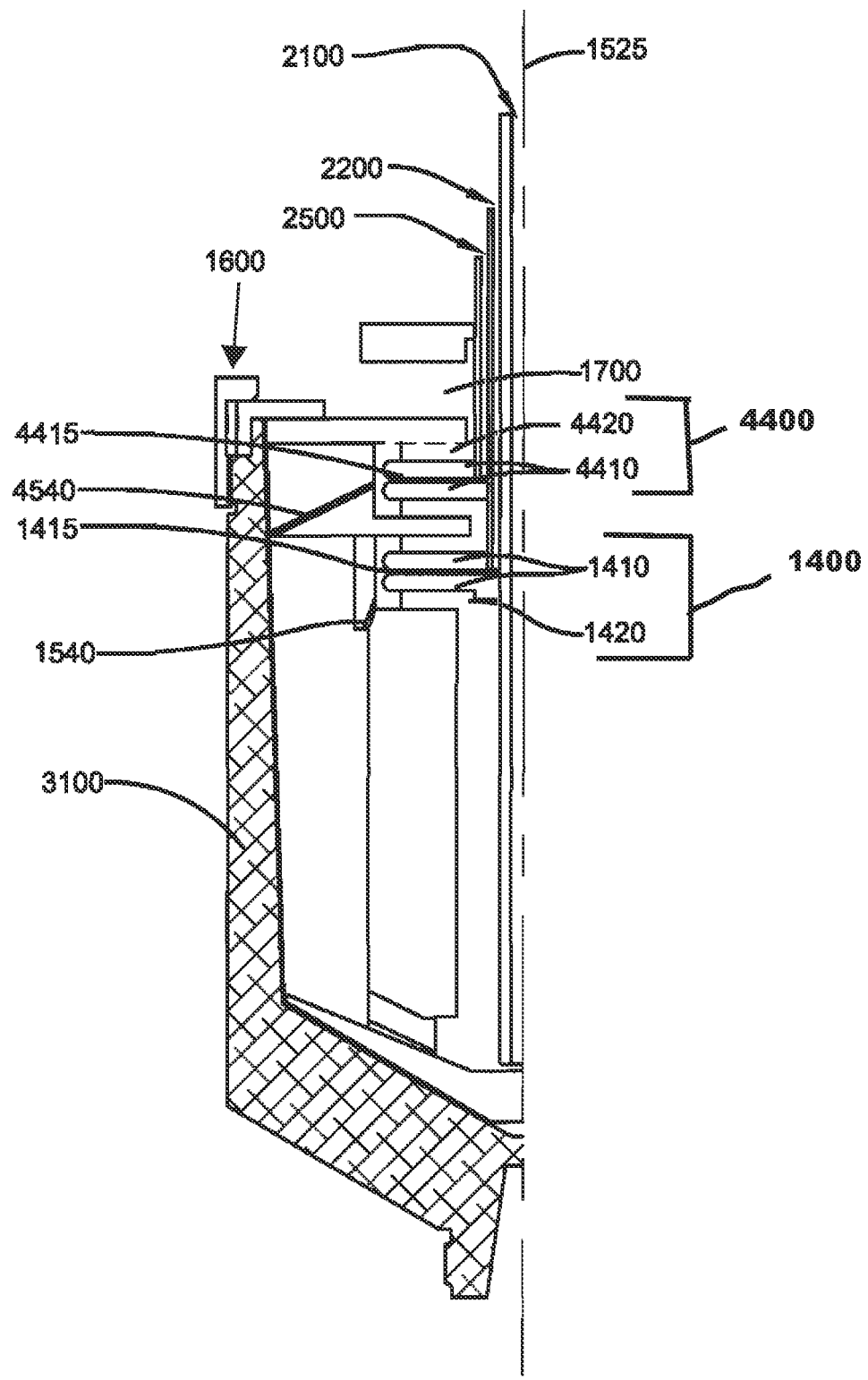
FIG. 10 is a schematic view of a portion of a continuous concentrate discharge centrifuge system.
Figure 11:
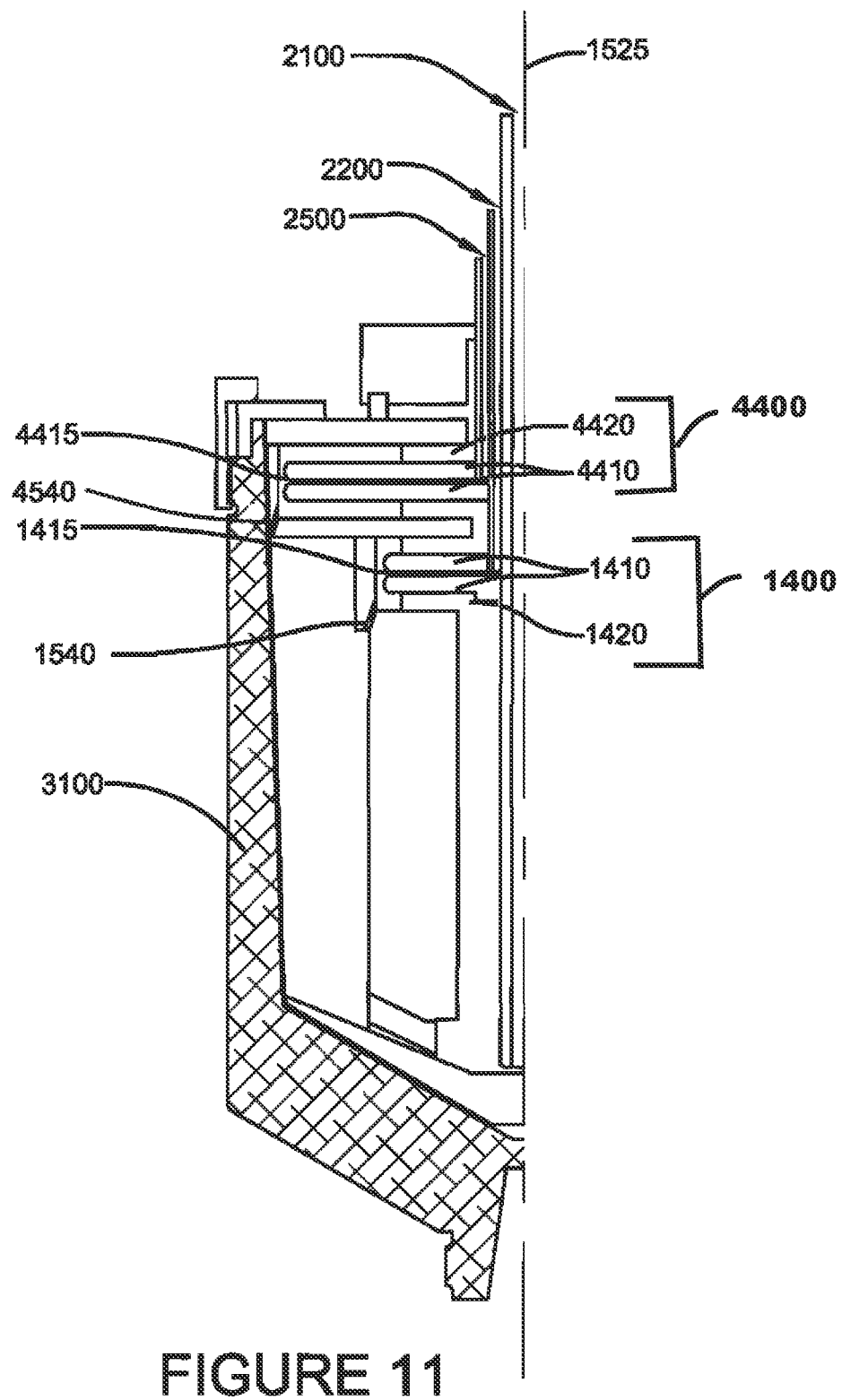
FIG. 11 is a schematic view of a portion of an arrangement which includes a continuous concentrate discharge centrifuge system.

In some exemplary arrangements, the upper and lower flanges 1300, 1200 may have a shape similar to that illustrated FIG. 1, but in some instances the upper surface of the single use centrifuge structure may have a different shape, as is illustrated in FIGS. 10 and 11. In the arrangements illustrated in FIGS. 10 and 11, rather than having a generally conical bowl cover 3200, to conform to generally conical upper flanges 1300, both the upper flanges and the bowl cover are relatively disk-shaped. The terms disc and disk are used interchangeably herein. Those skilled in the art will be able to adapt the sealing techniques described herein for use with differently shaped sealing surfaces.

Figure 4:
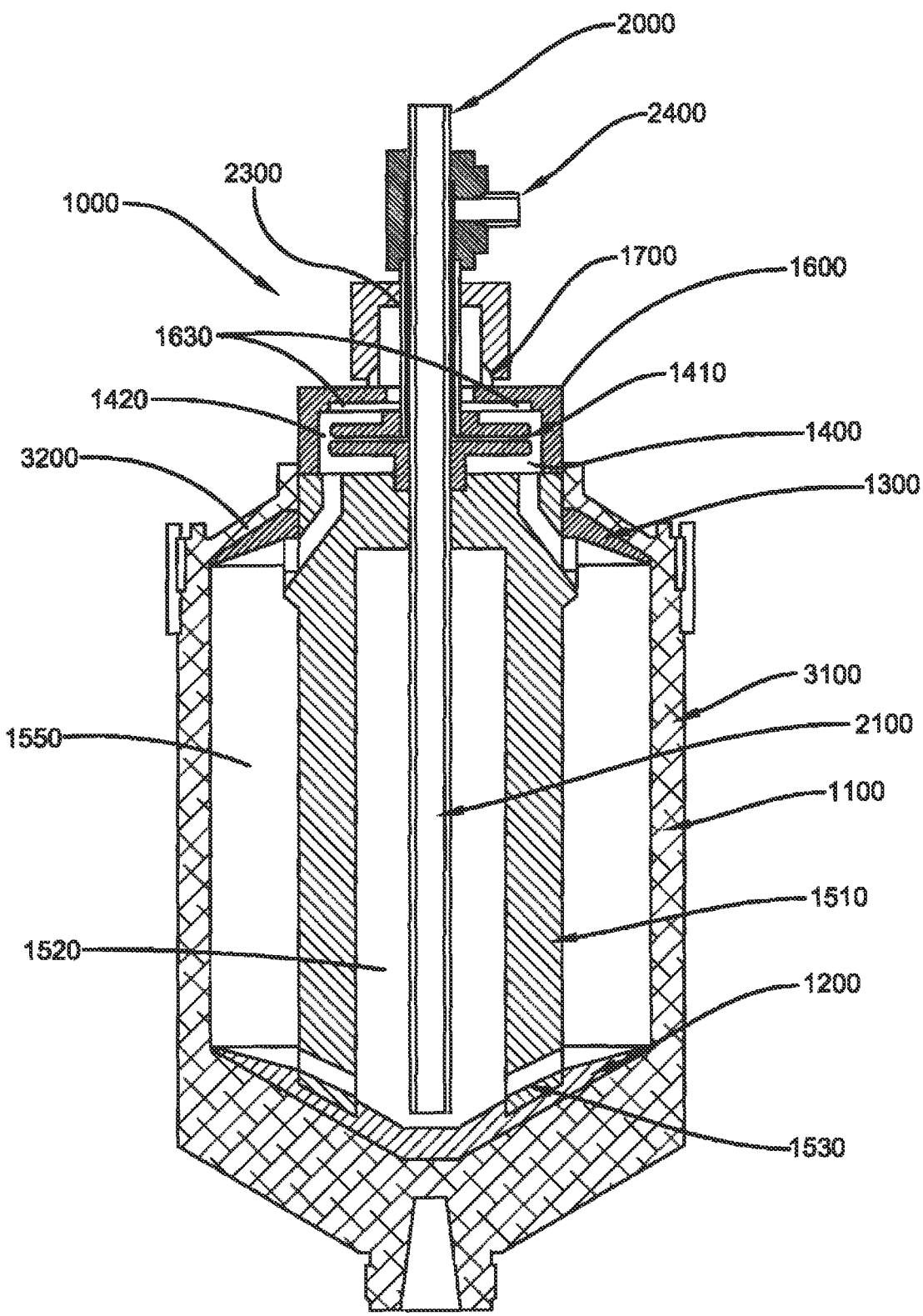
FIG. 4 is a schematic view of the arrangement illustrated in FIG. 1, in which the pump chamber of the centrifuge system includes accelerator fins.
Figure 5:
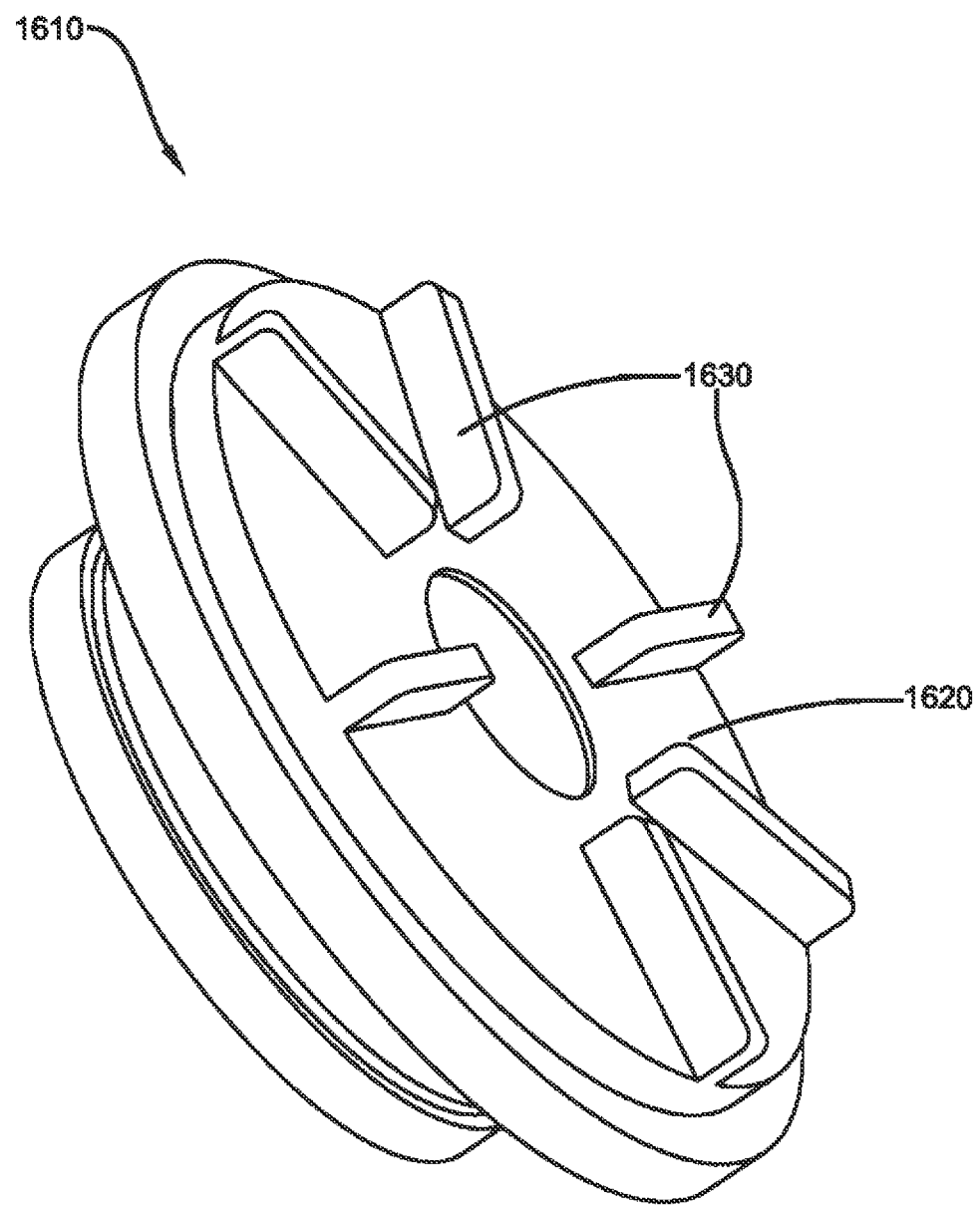
FIG. 5 is an isometric view of the top of the pump chamber of the example arrangement of the centrifuge system illustrated in FIG. 4.

FIGS. 4-5 illustrate an example arrangement with features to improve the efficiency of the centripetal pump 1400. As shown in detail in FIG. 5, this arrangement of an internal structure for single use components similar to that illustrated in FIGS. 1 and 2 includes a plurality of radial fins 1630 on the inner face 1620 of a cap portion 1610 of the pump chamber 1420. FIG. 5 shows the inner face 1620 of the cap portion 1610 of centrifuge cover 1600. The radial fins 1630, which may be alternatively referred to as vanes, may be thin, generally rectangular, radial plates, extending perpendicularly from the inner surface 1620 of the cap portion 1610. In the exemplary arrangement, six (6) fins 1630 are illustrated, but other arrangements may include fewer or more fins 1630. In this arrangement, fins 1630 form part of the inner face of cap 1620, but in other arrangements may comprise the upper surface 1620 of pump chamber 1420, which may take a form other than cap 1610. When the centrifuge system 1000 is in use, fins 1630 are located above the paring disks 1410 of the centripetal pump 1400 in the chamber 1420. These fins 1630 transmit the angular rotation of the centrifuge 1000 to the centrate within in the pump chamber 1420.

This increases the efficiency of the centripetal pump 1400, stabilizing the gas to liquid interface in the pump chamber 1420 above the paring disks 1410, and increasing the size of the gas barrier. The gas barrier is a generally cylindrical column of gas extending from the exterior of the feed/discharge mechanism 2000 outward into the pump chamber 1420 to the inner surface of the rotating centrate. This increase in the size of the barrier occurs because the resulting increase in angular velocity of the centrate forces the centrate toward the wall of the centrifuge. When rotating centrate within the pump chamber 1420 comes into contact with the stationary paring disks 1410 the resulting friction may decrease the efficiency of the pump 1400. The addition of a plurality of radial fins 1630, which rotate with the same angular velocity as the centrate, overcomes any reduction in velocity that might otherwise result from the encounter between the rotating centrate and the stationary paring disks 1410.

Figure 6:
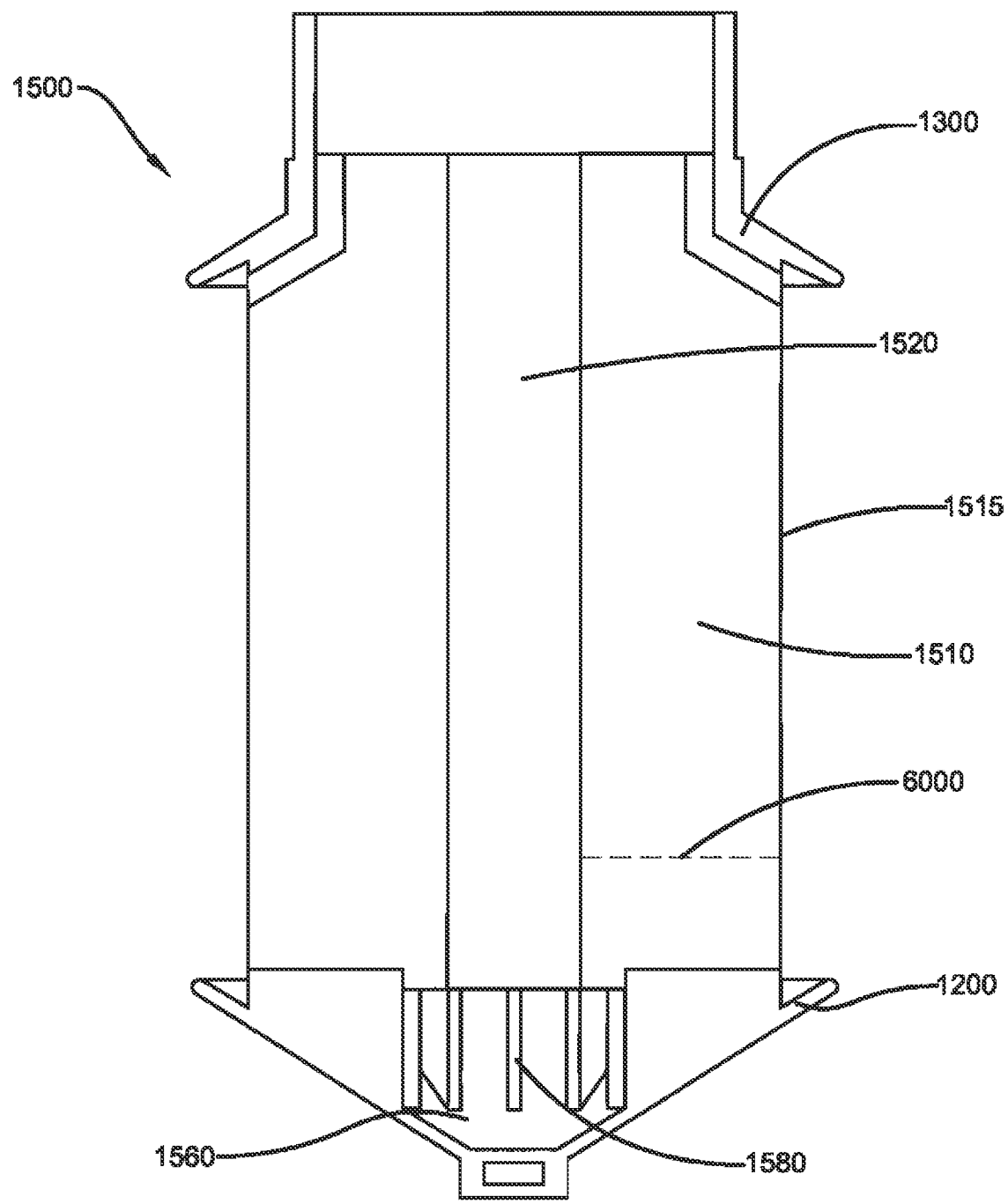
FIG. 6 is an isometric cutaway view of the core, upper flanges and lower flanges, of a single use centrifuge system with an enlarged core diameter (to create a shallow pool centrifuge), and a feed accelerator.

FIG. 6 shows an exemplary arrangement of an improved core structure 1500 for use in high turbidity feeds. Core structure 1500 includes a core 1510, upper flange 1300, and lower flange 1200. Core 1510 has a cylindrical central cavity 1520 adapted to permit feed tube 2100 to be inserted into the central cavity 1520. The distance from the central axis 1525 to the exterior of core 1515 (the core width, represented by dashed line 6000 in FIG. 6) is larger than the corresponding distance in the arrangement illustrated in FIG. 3. The larger diameter core 1510 decreases the depth (represented by dashed line 6010) of the separation chamber 1550, making centrifuge 1000 operate as a shallow pool centrifuge. The depth 6010 of a separation chamber 1550 is generally the distance between the exterior of the core 1510 and the flexible liner 1100, labeled in FIGS. 1 and 12. A shallow pool centrifuge is one which has a depth 6010 which is small, relative to the diameter of the centrifuge. As can be seen in the exemplary arrangement illustrated in FIG. 12, in order to facilitate removal of the cell concentrate, the shallow pool depth 6010 may vary from shallower at the bottom of separation chamber 1550 to somewhat deeper the top of the separation chamber 1550. In some arrangements illustrated herein, the ratio of the average separation pool depth 6010 to the core width is 1:1 or lower. An example of a shallow pool centrifuge is offered as an optional model of the ViaFuge® which is a centrifuge system, manufactured by Pneumatic Scale Corporation. The advantage of a shallow pool centrifuge is that it enables separation at higher feed flow rates. This is accomplished by virtue of a higher average g-force for a given inner bowl diameter, which creates a higher sedimentation velocity at a given angular velocity. The resulting enhanced separation performance is beneficial when separating highly turbid feeds containing a high concentration of cell debris.

The example arrangement of the core structure 1500 which is illustrated in FIG. 6 also includes accelerator vanes 1560 as part of the lower flange 1200. Accelerator vanes 1560 (as shown in FIG. 12), rather than holes 1530 through a solid core 1510 (as shown in FIG. 10-11), comprise an alternate arrangement of a fluid connection between the central cavity 1520 of the core 1510 and the separation chamber 1550.

Figure 7:
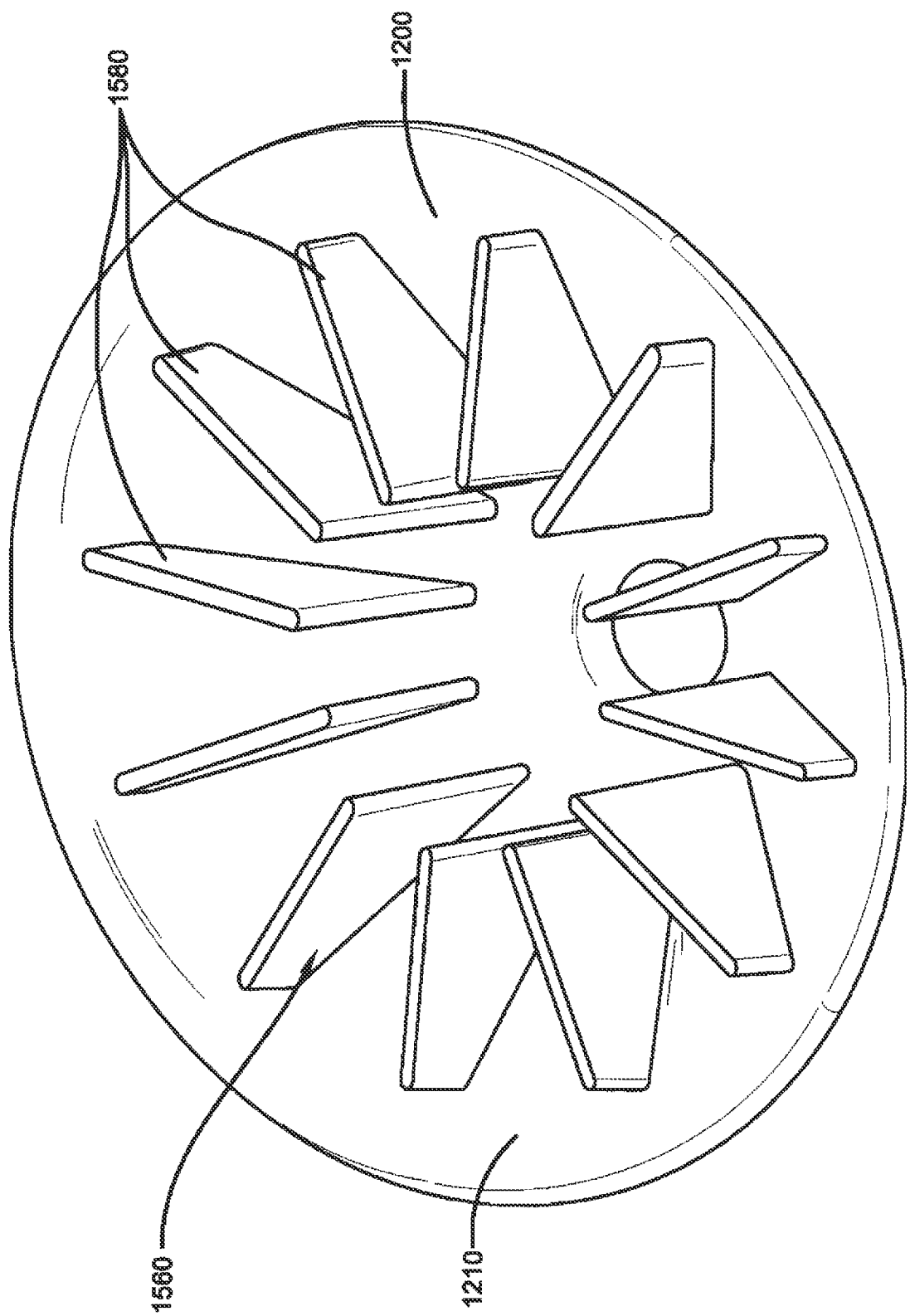
FIG. 7 is an isometric view of the feed accelerator of FIG. 6.
Figure 8:
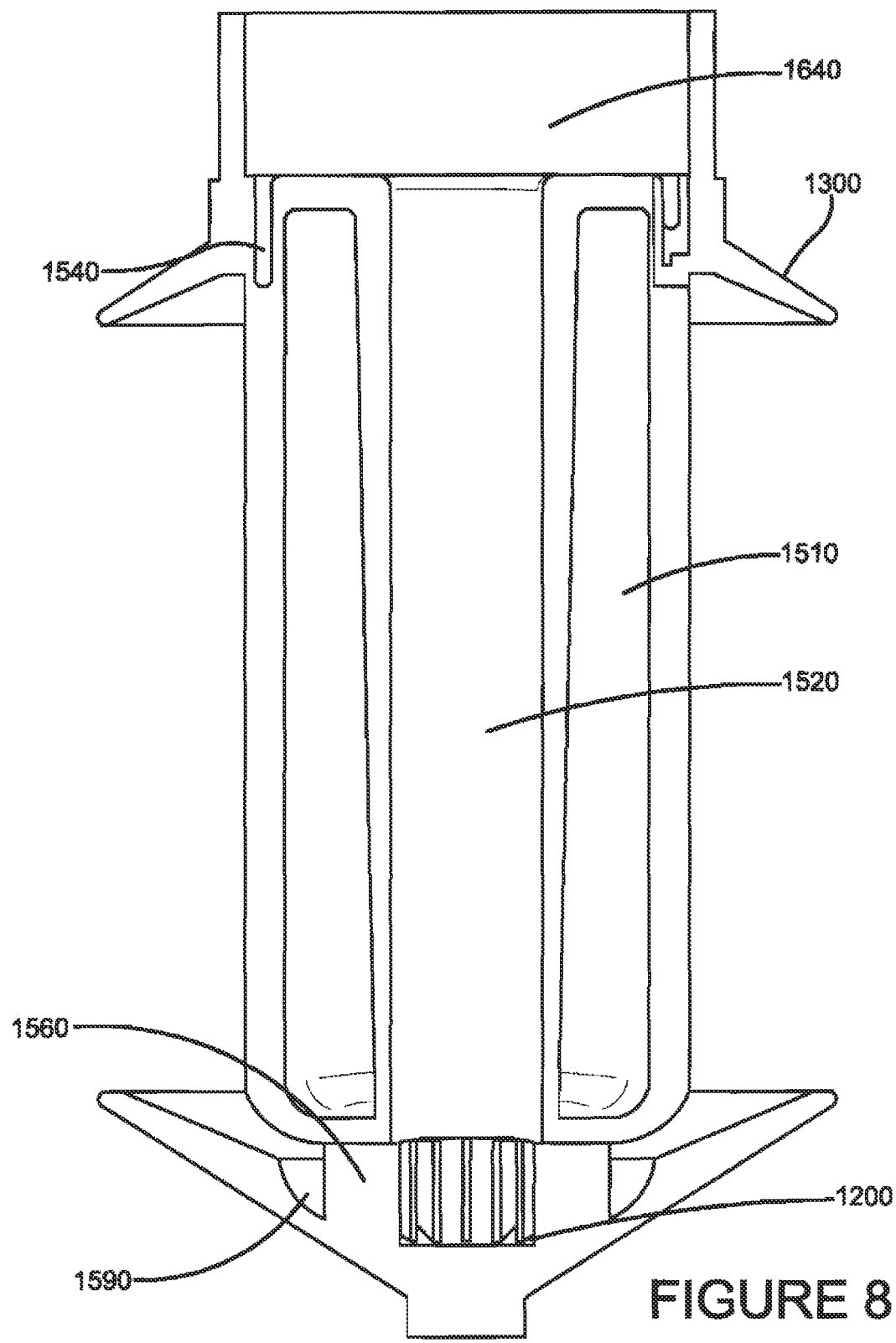
FIG. 8 is an isometric cutaway view of the core and upper flanges of a single use centrifuge system with a standard core diameter, and a feed accelerator with curved vanes and an elliptical bowl.
Figure 9:
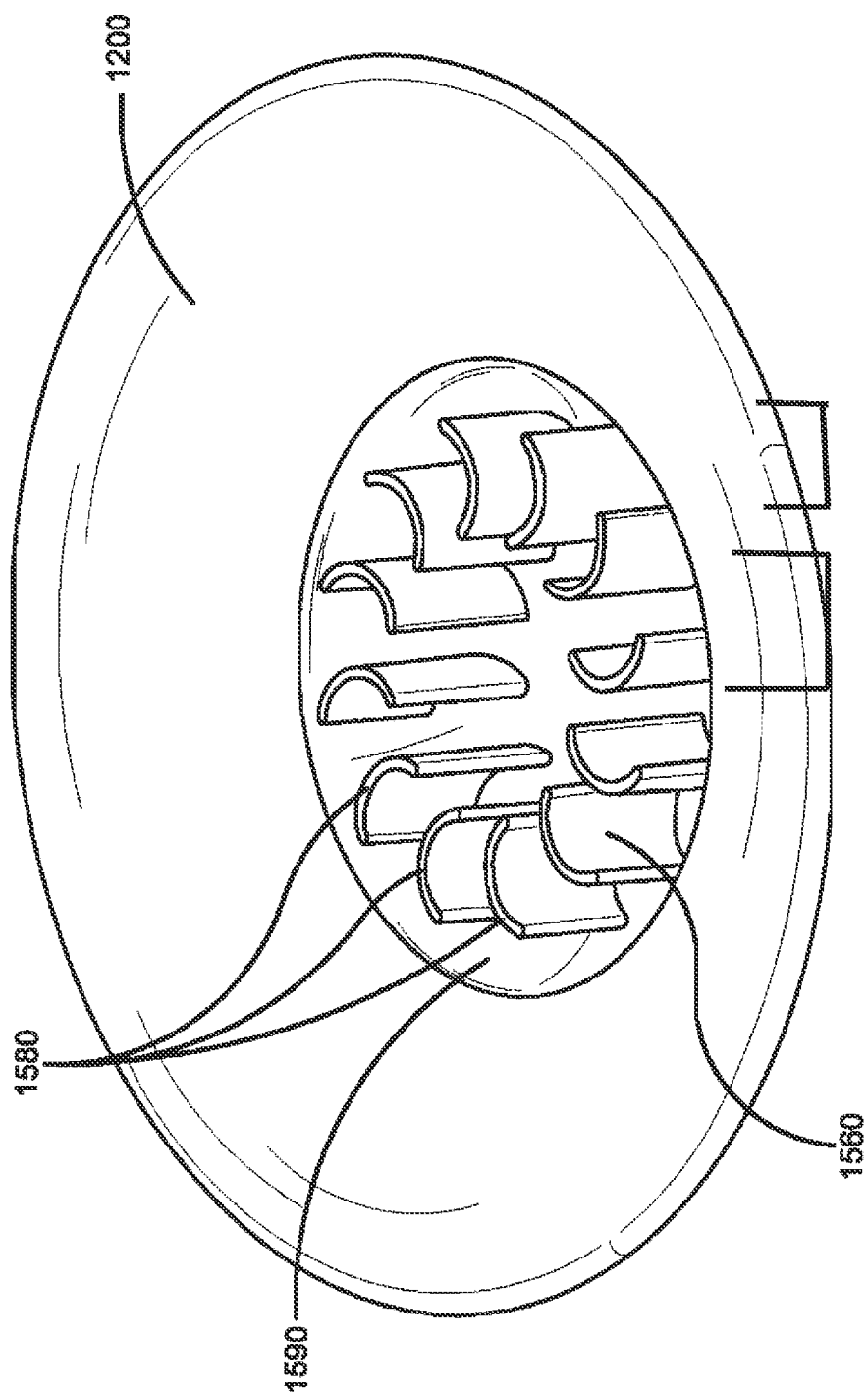
FIG. 9 is an isometric view of the feed accelerator of FIG. 8.

In the exemplary arrangement of a core structure 1500 shown in FIG. 6, accelerator vanes 1560 comprise a plurality of radially, generally rectangular, spaced thin plates 1580 extending upward from the upper conical surface of the lower flange 1200. Plates 1580 extend upward orthogonal to the base of the core 1510. Plates 1580 generally extend radially outward from near the axis 1525 of the core 1510. In the exemplary arrangement, there are 12 plates 1580, as shown most clearly in FIG. 7. In other arrangements there may be fewer or more than 12 plates 1580. In addition, in other arrangements the plates 1580 may be curved in the direction of rotation of the centrifuge 1000, as shown in an exemplary arrangement in FIG. 9. The interior surface of lower flange 1200 may be modified to form an elliptical accelerator bowl 1590, with the curved plates extending upward therefrom. These arrangements are intended to be exemplary, and those skilled in the art may combine them in different ways or may modify these arrangements to further benefit from the turbidity reduction these plates and the shape of the lower flange 1200 and/or an embedded accelerator bowl create.

Further features of an example arrangement of a single use centrifuge 1000 which is designed to operate continuously or semi-continuously are illustrated in FIGS. 10-12. The exemplary arrangement illustrated in FIG. 10 includes a second centripetal pump arrangement 4400 for removal of cell concentrate. Centripetal pump arrangement 4400 for the removal of cell concentrate is located above the centripetal pump 1400 for removal of centrate. Centripetal pump arrangement 4400 includes a pump chamber 4420 and paring disks 4410. A plurality of holes or continuous slits 4540 extend from the upper outer circumference of the separation chamber 1550 into pump chamber 4420, providing fluid connection from outer portion of the separation chamber 1550 to the second pump chamber 4420. As with pump chamber 1400, pump chamber 4400 may have a different shape than that illustrated in FIGS. 10-12, but will generally be an axially symmetric chamber near the upper end of the core structure 1500 which is in fluid connection with the separation chamber 1550. As with pump chamber 1400, the pump chamber may be partially or entirely recessed within core structure 1500. If a centrate pump chamber 1400 is present near the upper end of the core structure 1500, the cell concentrate pump chamber 4400 will generally be located above it. A pump chamber 4400, for the removal of cell concentrate, will be in fluid connection with separation chamber 1550 via holes or slits 4540 which extend from adjacent the radially outer upper wall of separation chamber 1550, in order to collect the heavier cell concentrate which is urged there by centrifugal forces.

In the arrangement illustrated in FIG. 10, the paring disks 4410 used in the concentrate discharge pump arrangement 4400 are approximately the same radius as those used in the centrate discharge pump 1400, and are rotationally fixed. In other arrangements, such as the one shown in FIG. 11, the paring disks 4410 in the concentrate discharge pump 4400 may have a larger radius than those in the centrate discharge pump 1400, with a correspondingly larger pump chamber 4420. Paring disks of various intermediate diameters may be used as well. The optimum diameter will depend on the properties of the cell concentrate that is to be discharged. Larger diameter paring disks have a higher pumping capacity, but create greater shear.

In the arrangements illustrated in FIGS. 1, 4, and 10, the paring disks 4410 in the concentrate discharge pump arrangement 4400 are rotationally fixed. In other arrangements, such as the one shown in FIG. 11, paring disks in 4410 may be adapted to rotate with an angular velocity between zero and the angular velocity of the centrifuge 1000. The desired angular velocity can be controlled by a number of mechanisms that are known to those skilled in the art. An example of a means of control is an external slip clutch that allows the paring disks 4410 to rotate at an angular velocity that is a fraction of that of the centrifuge 1000. Other means of controlling the angular velocity of the paring disks will be apparent to those skilled in the art.

In the exemplary arrangements illustrated in FIGS. 1, 4, 10-12, the gaps 1415, 4415 between paring disks 1410 and 4410 are fixed. In other exemplary arrangements, such as the arrangement in FIG. 13, the gaps 1415, 4415 between paring disks 1410 and 4410 may be adjustable, in order to control the flow rate at which centrate or concentrate are removed from the centrifuge 1000. One of each pair of paring disks 1410 and 4410 is attached to a vertically moveable throttle tube 6100. Throttle tube 6100 may be moved up or down in order to narrow or widen the gap 1415, 4415 between each pair of the paring disks 1410, 4410. In addition, an external peristaltic pump 2510 (not shown) may be added to the concentrate removal line 2500 (not shown) to aid in removal of concentrate. This pump 2510 may be controlled by a sensor 4430 in the pump chamber 4420. The sensor 4430 (not shown) may also be used to control a diluent pump 5150 in order to synchronize concentrate removal with the addition of diluents.

Figure 13:
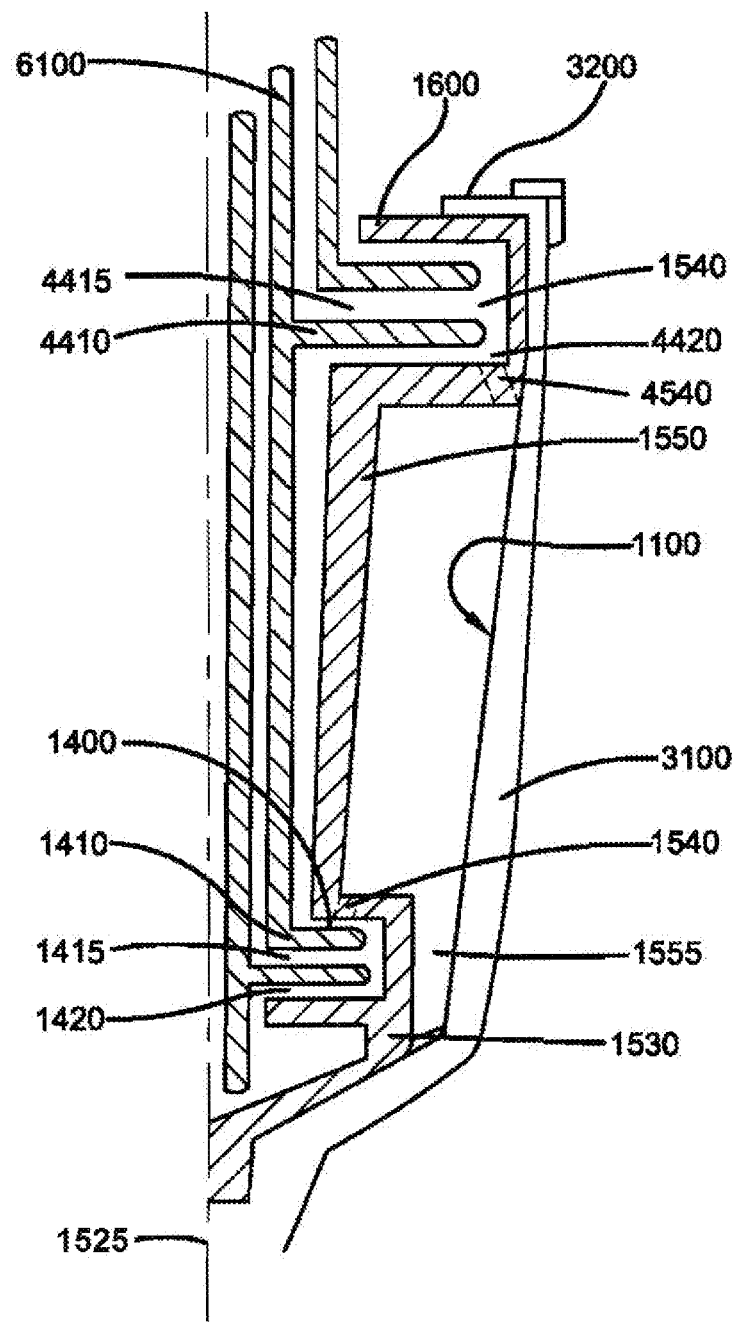
FIG. 13 is schematic view of a portion of another example arrangement of a continuous concentrate discharge system, with a throttle mechanism for the centripetal pumps.
Figure 14:
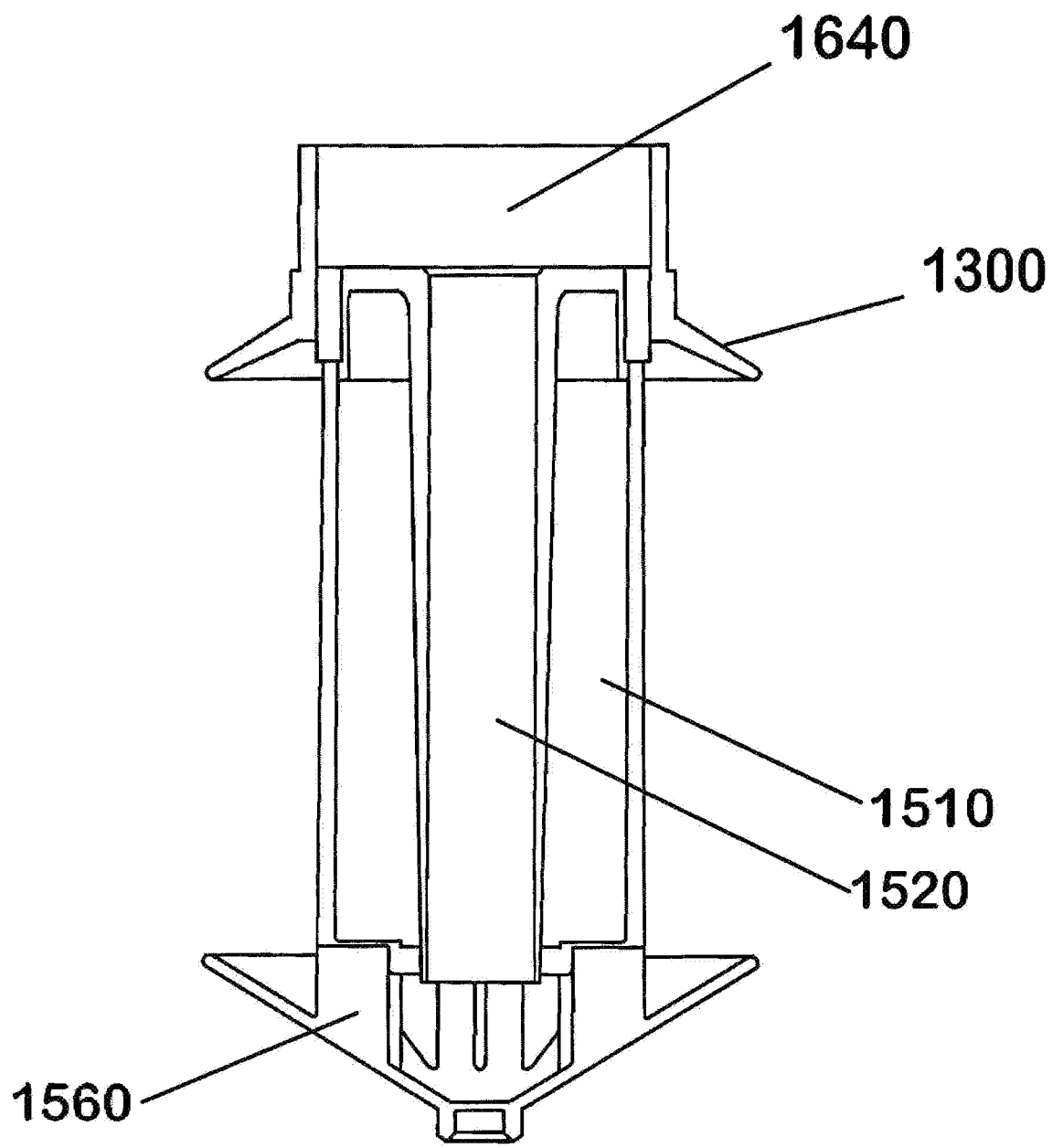
FIG. 14 is an isometric cutaway view of the core and upper flanges of a single use centrifuge system with a core, and a feed accelerator with straight vanes.
Figure 15:
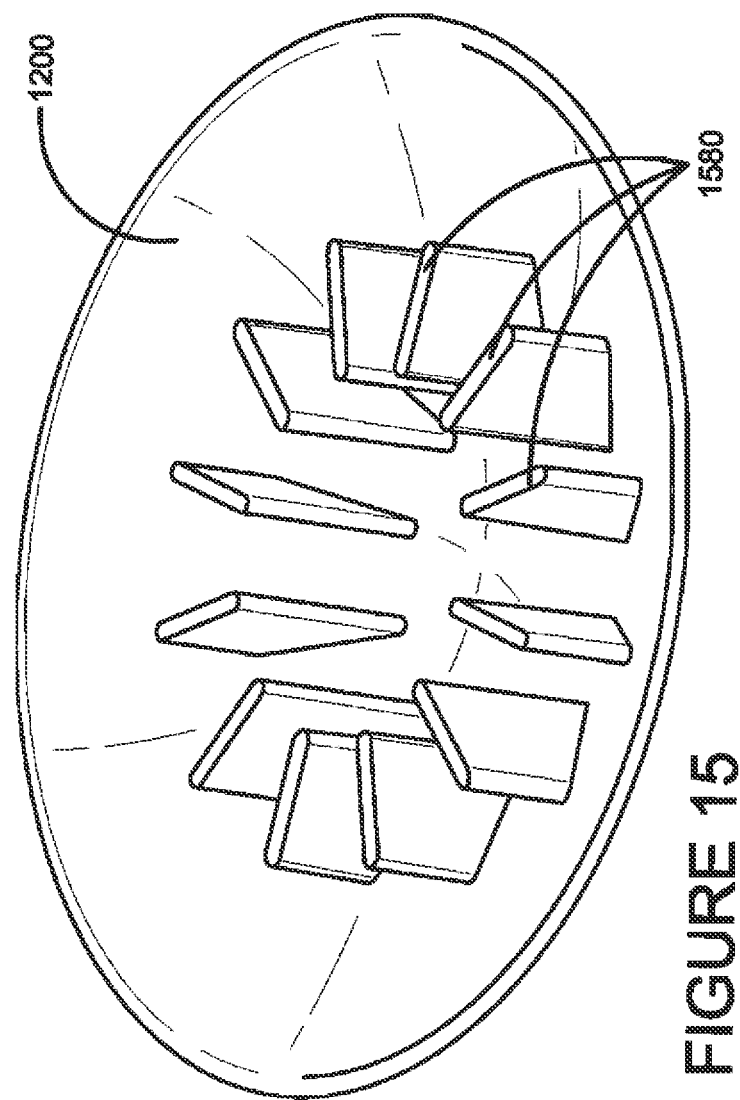
FIG. 15 is an isometric view of the feed accelerator of FIG. 14.

Also illustrated in FIG. 13 is an arrangement in which the centrate pump 1400 is located at the base of the centrifuge 1000. In the arrangement illustrated in FIG. 13, a centrate well 1555 is created between the pump chamber 1420 and the flexible liner 1100. Holes 1530 extend from the core 1510, below the pump chamber 1420, into the centrate well 1555. In addition, in the exemplary arrangement illustrated, holes 1540 extend from the separation chamber 1550, adjacent the exterior surface 1515 of the core 1510, into the pump chamber 1420 to permit the centrate to be removed using centrate pump 1400. Holes 4540 may also extend between the separation chamber 1550, adjacent its outer upper surface, into pump chamber 4420 to permit cell concentrate to flow into pump chamber 4420 to be removed using centripetal pump 4400.

As noted above, in the exemplary arrangement illustrated, the gaps 1415, 4415 between the paring disks 4410 and 1410 may be adjustable by use of a throttle tube 6100 connected to one of each pair of paring disks 4410, 1410. Throttle tube 6100, and the attached one of each paring disk pair 4410, 1410, may be moved up or down to narrow or widen gaps 1415, 4415. In the exemplary arrangement illustrated, the throttle tube 6100 is attached to the lower and upper paring disk of paring disk pairs 4410, 1410, respectively. In other arrangements the attachment may be reversed, may be used to throttle a single centripetal pump, or may be used to throttle both in parallel (rather than opposition as illustrated in FIG. 13).

As can be seen in the arrangements illustrated in FIGS. 10-12, the wall of the solid multiple use bowl 3100 is thicker at the base than it is in the upper portion, in order to create a cavity with an internal truncated cone shape to support single use centrifuge structure 1000 which has a smaller radius at the lower end than at the upper end. This larger radius at the upper end of the separation chamber 1550 moves the denser cell concentrate toward the upper outer portion of the separation chamber 1550 and into centripetal pump chamber 4420. In the arrangement illustrated, the truncated cone shape is created by a multiple use bowl 3100 with a wall which is thicker at the base than it is in the upper portion. Those skilled in the art will recognize that a multiple use bowl 3100 with a cavity having an internal truncated cone shape may also include walls of uniform thickness, and that there may be other variations which create the desired internal shape for the multiple use bowl 3100.

In the example arrangements illustrated in FIGS. 10-12, feed mechanism 2000 also includes an additional pathway for the removal of cells, or cell concentrate. In the arrangement illustrated in FIG. 1, the cylindrical pathway 2200 around the feed tube 2100 is used to remove centrate. The arrangements illustrated in FIGS. 10-12 also include, a concentric cylindrical pathway for the removal of cells or cell concentrate, referred to as a cell discharge tube 2500. Cell discharge tube 2500 surrounds the centrate removal pathway 2200. If the centrifuge is designed to be used with a concentrate that is expected to be very viscous, an additional concentric cylindrical fluid pathway 5000 may be added around the feed tube 2100 to permit the diluents to be introduced into the cell concentrate pump chamber 4420 in order to decrease the viscosity of the concentrate. The diluent pathway 5000, in the exemplary arrangement illustrated in FIG. 12, comprises a concentric tube surrounding the cell discharge pathway, and opens at the lower end into a thin disk-shaped fluid pathway 5100 above paring disks 4410, discharging near the outer edge of the paring disks 4410 to provide fluid communication with the pump chamber 4420. Injecting the diluent by this means, and in this location, limits the diluent to mixing with, and being discharged with, the concentrate rather than being introduced into the centrate, which may be undesirable in some applications. In alternative arrangements, the diluents may be introduced directly onto the upper surface of the paring disks and allowed to spread radially outward, or onto a separate disk located above the paring disks.

The choice of diluent will depend on the objectives of the separation process and the nature of the cell concentrate that is to be diluted. In some cases a simple isotonic buffer or deionized water can serve as the diluent. In other cases, diluents that are specific to the properties of a cell concentrate may be advantageous. For example, in production scale batch cell culture operated at low cell viability, flocculants are commonly added to the culture as it is being fed to a centrifuge to cause cells and cell debris to flocculate or agglomerate into larger particles, which facilitates their separation by increasing their rate of sedimentation. Since both cells and cell debris carry negative surface charges, the compounds used as flocculants are typically cationic polymers, which carry multiple positive charges, such as polyethyleneimine. By virtue of their multiple positive charges, such flocculants can link negatively charged cells and cells debris into large agglomerates. An undesirable consequence of the use of such flocculants is that they further increase the viscosity of cell concentrates. Therefore, a particularly useful diluent in this application is a deflocculant that will disrupt the bonds that increase the viscosity of the cell concentrate. Examples of deflocculants include high salt buffers such as sodium chloride solutions ranging in concentration from 0.1 M to 1.0 M. Other deflocculants that may be useful in reducing the viscosity of cell concentrate are anionic polymers such as polymers of acrylic acid.

In the case of a cell concentrate wherein cell viability is to be maintained, a diluent can be chosen that is a shear protectant, such as dextran or Pluronic F-68. The use of a shear protectant, in combination with an isotonic buffer, will enhance the survival and viability of cells as they are being discharged from the centrifuge.

The exemplary centrifuge illustrated in FIG. 4 operates as described below. During a feed cycle, a feed suspension flows into the rotating bowl assembly through feed tube 2100. As the feed suspension enters the central cavity 1520 of core 1510 near lower flange 1200, it is urged outward along the upper surface of lower flange 1200 by centrifugal forces, passing into the separation chamber 1550 through holes 1530 in core 1510.

Centrate collects in the separation chamber 1550, a hollow, roughly cylindrical space below the upper flange 1300 surrounding core 1510. The centrate flows upward from its entrance into the separation chamber through holes 1530 until it encounters holes 1540 between the separation chamber 1550 and the pump chamber 1420 in the upper portion of the separation chamber 1550, adjacent the core 1410. Particles of density higher than that of the liquid are moved toward the outer wall of the separation chamber 1550 by sedimentation (particle concentrate), away from holes 1530. When the rotation of the centrifuge 1000 is stopped, the particle concentrate moves downward under the influence of gravity to the nozzle 2110 of the feed tube 2100 for removal via the combined feed/discharge mechanism 2000.

During rotation, the centrate enters the centrate pump chamber 1420 through holes 1540. Within the pump chamber 1420, the rotating centrate encounters stationary paring disks 1410, which convert the kinetic energy of the rotating liquid into pressure which urges the centrate being discharged upward through the centrate discharge path 2200 within the feed/discharge mechanism 2000 and out through the centrate discharge tube 2400.

The efficiency of the centripetal pump 1400 is increased by adding radial fins 1630 on the inner surface 1620 of the cap portion 1610 of the rotating pump 1400. These fins 1630 impart the angular momentum of the rotating assembly to the centrate in the pump chamber 1420, which might otherwise slow because of friction when the rotating centrate encounters the stationary paring disks 1410. The centripetal pump 1400 provides an improved means of centrate discharge, over mechanical seals, because of the gas liquid interface within the pump chamber 1420. The gas within the pump chamber 1420 is isolated from contamination by the external environment by the rotating seal 1700. Because the centrate being discharged between the paring disks 1410 does not come into contact with air, either during the feed or discharge process, it avoids the excessive foaming that often occurs when the discharge process introduces air into the cell culture.

In the exemplary centrifuge 1000 illustrated in FIGS. 4-5, cell concentrate is discharged by periodically stopping bowl rotation and the feed flow and then pumping out the cell concentrate that has been collected along the outer walls of the separation chamber 1550. This process is known as intermittent processing. When the volumetric capacity of the separation chamber 1550 is reached, centrifuge rotation is stopped. The cell concentrate moves downward toward nozzle 2110 of feed tube 2100, where the concentrate is withdrawn by pumping it out through the feed tube 2100. Appropriate valving (not shown) external to the centrifuge 1000 is used to direct the concentrate into a collection vessel (not shown). If the entire bioreactor batch has not yet been completely processed, then bowl rotation and feed flow are resumed, and is followed by additional feed and discharge cycles until the full batch has been processed.

As noted above, when the cell culture is concentrated or contains significant cell debris, the process described above slows down because residence time must be increased to capture small debris particles, which necessitates a slower feed flow rate and the separation chamber 1550 fills rapidly and rotation must be halted frequently and repeatedly for each culture batch. In addition, the cell concentrate tends to be more viscous so gravity does not work as efficiently to drain the cell concentrate to the bottom of the centrifuge 1000 so it takes longer and, in some instances, may require a wash to remove the remaining cells.

The single use centrifuge, as modified in the exemplary arrangements illustrated in FIGS. 6-13, creates a higher average settling velocity without an increase in angular velocity, permits the centrifuge 1000 to run continuously or semi-continuously, and allows a diluent to be added to the cell concentrate during the cell removal process so that the removal of cells is more easily and more completely accomplished.

Exemplary arrangements of a single use centrifuge structure 1000 shown in FIGS. 6-12 operate as discussed herein. Feed suspension enters the single use centrifuge structure 1000 via feed tube 2100. As the feed suspension encounters accelerator vanes 1560, the vanes 1560 impart an angular velocity to the feed suspension which approaches the angular velocity of the single use centrifuge 1000. The use of vanes 1560, rather than holes 1530, provides for a greater volume of feed suspension to enter the separation chamber 1550 at a slower radial velocity, avoiding the jetting which occurs when the feed suspension is forced through holes 1530 having smaller cross sectional openings than the openings between the vanes 1560. This reduction in velocity of the feed stream as it enters the separation zone, or pool, minimizes disruption of the liquid contents of the pool, which allows for more efficient sedimentation.

As the centrifuge 1000 rotates, the particles which are denser than the centrate are urged toward the outside of the separation chamber 1550, leaving the particle free centrate near the core 1510. The cavity in the centrifuge bowl 3100 has the shape of an inverted truncated cone, with a wider radius at the upper end than the lower end. The centrifugal force causes the particles to collect in the upper and outer portion of the chamber. The centrifuge 1000 may operate with semi-continuous discharge of concentrate. The centrate discharge works, generally, as described with respect to FIG. 4. The cell concentrate discharge works similarly, with the cell concentrate collecting near the upper radially outer portion of the separation chamber 1550 and entering the concentrate discharge pump chamber 4400 via holes 4540 adjacent the upper outer wall of the separation chamber 1550.

The rate of feed of suspension, as well as the angular velocity of rotation, may be monitored using a vibration sensor system such as the one described in U.S. Pat. No. 9,427,748, incorporated by reference herein in its entirety. Such a sensor system may permit the centrifuge to be filled at a lower rate until the vibrations indicate the centrifuge is nearly full, then to adjust the feed rate and angular velocity appropriately in response to this information. Typically, the feed rate will be decreased or stopped once the centrifuge is nearly full and the angular velocity will be increased in order to increase the settling velocity and once the settling and discharge is essentially complete, the cycle will be repeated. If the system is optimized using the additional features described herein to diminish the need to interrupt the process, it may be possible to operate the system continuously, or nearly continuously, at the angular velocity needed for settling.

With semi-continuous concentrate discharge, the suspension continues to be fed into the centrifuge 1000, using concentrate pump 4400 operating intermittently to remove concentrate. The operation of concentrate pump 4400 may be controlled by an optical sensor in the concentrate discharge line that indicates the presence or absence of concentrate being discharged. In lieu of a concentrate pump 4400, the discharge cycle may be managed electronically using a controller and sensors which determine when to open and shut a valve for the most efficient processing of the fluid suspension.

The average rate of discharge may further be controlled by using a centrifuge 1000 with an adjustable gap between the paring disks 4410, 1410. It should be noted that it may only be desired or necessary for one set of paring disks 4410, 1410 to be adjustable. The gap between paring disks 4410, 1410 (which forms a part of the fluid pathway out of the centrifuge 1000) may be opened to permit flow, or closed to shut the flow off, acting as an internal valve. Depending on the desired product, or the characteristics of the product, it may also be useful to widen or narrow the gap 4415, 1415 between paring disks 4410, 1410. Changing the gap affects both pumping and shear rates associated with the paring disks.

The rate of removal of concentrate and centrate from the centrifuge 1000, and the viability of the concentrate removed, may be further controlled using a number of features of exemplary arrangements shown in FIGS. 4-13. Accelerator fins 4630, similar to those in the centrate pump chamber 1420, may be added to concentrate pump chamber 4420. The addition of accelerator fins 4630 increases the rate at which the concentrate may be removed, by overcoming some of the slow down due to friction between the moving concentrate and the paring disks 4410. In addition to accelerator fins 4630 in the upper surface of the pump chamber 4420, such fins 4630 may also be added to a lower surface in the pump chamber 4420 to increase their effectiveness. A further feature may be the substitution of slits for holes 1540, 4540, which minimizes the shear on material entering the pump chambers 1420, 4420.

If viability of the concentrate is a concern, in some arrangements rotatable paring disks 4410 may be included in pump chamber 4420, which reduce the shear imparted to the concentrate as it contacts the surfaces of the paring disks 4410. The rotation rate of paring disks 4410 may be adjusted to a rate somewhat between stationary and the rate of rotation of the separation chamber 1550 to balance concentrate viability against the rate of discharge. The desired angular velocity can be controlled by a number of mechanisms that are known to those skilled in the art. An example of a means of control is an external slip clutch that allows the paring disks to rotate at an angular velocity that is a fraction of that of the centrifuge. The use of slip clutches is well known to those skilled in the art. In addition, there may be means other than slip clutches to adjust the angular velocity that will be apparent to those skilled in the art.

A peristaltic pump 2510 may be also used in some arrangements to make removal of the concentrate more efficient and reliable, particularly with very concentrated feed suspensions. Using a peristaltic pump 2510 permits the user to more precisely control the rate of flow of the concentrate from the centrifuge 1000 than is possible relying on centripetal pumps 4400, alone, because the rate of centripetal pumps are not as easily adjustable as the rate of a peristaltic pump 2510.

In addition, a diluent, such as sterile water or a buffer, may be pumped into the concentrate pump chamber 4420 through the diluent pathway 5000 using a diluent pump 5150 in order to cut the viscosity of the concentration. A more complete discussion of useful exemplary diluents can be found above. The rate at which either or both of the peristaltic pump 2510 or the diluent pump 5150 operates may be controlled by an automated controller (not shown) responsive to a concentration sensor 4430 located in the concentrate discharge connection 2500. The controller may be programmed to start, stop, or modify the pump rate for both diluent addition and concentrate removal responsive to the particle concentration in the concentrate, either independently, responsive to a concentration sensor 4430, in conjunction with a standard feed/discharge cycle, or as a combination.

Figure 16:
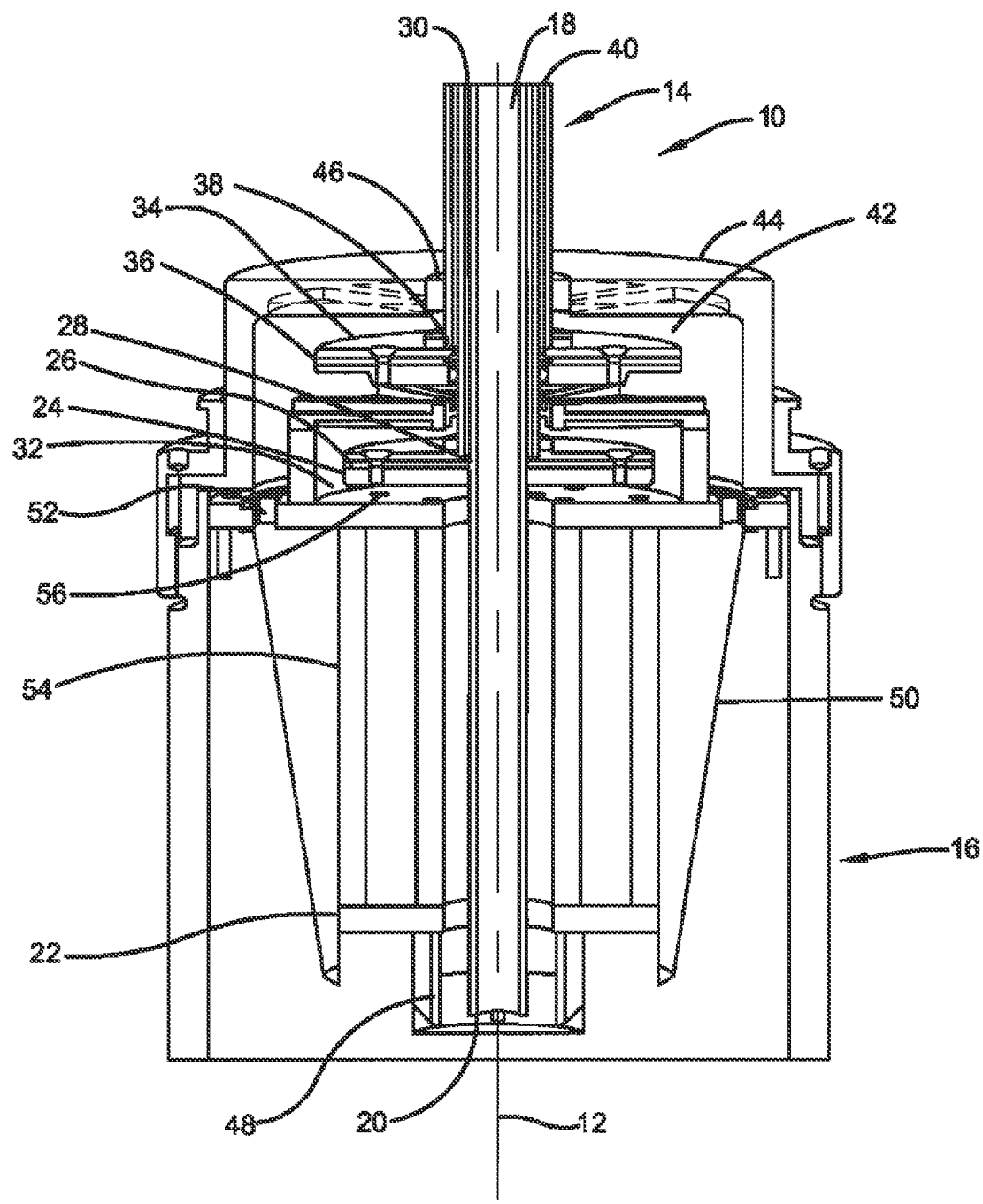
FIG. 16 is an isometric cutaway view of an alternative continuous concentrate discharge centrifuge system.

FIG. 16 shows an alternative example arrangement of a structure used in connection with a centrifuge that provides continuous separation processing to produce continuous concentrate and centrate feeds. The module core 10 is similar to those previously discussed that is configured to be removably positioned in the rotatable bowl of a centrifuge. The centrifuge bowl and the core rotate about an axis 12 during processing. The apparatus includes a stationary assembly 14 and a rotatable assembly 16.

As with the previously described arrangements, the stationary assembly 14 includes a feed tube 18. The feed tube 18 is coaxial with the axis 12 and terminates in an opening 20 adjacent the bottom of the separation chamber or cavity 22 of the core. The stationary assembly further includes a centrate centripetal pump 24. The exemplary embodiment of the centrate centripetal pump 24, which is described in greater detail hereafter, includes inlet opening 26 and an annular outlet opening 28. The annular outlet opening is in fluid connection with a centrate tube 30. The centrate tube extends in coaxial surrounding relation with the feed tube 18.

In this exemplary arrangement, the centrate centripetal pump 24 is positioned in a centrate pump chamber 32. The centrate pump chamber is defined by walls which are part of the rotatable assembly, and which during operation provide for the inlet openings 26 of the centrate centripetal pump to be exposed to a pool of liquid centrate.

The exemplary arrangement further includes a concentrate centripetal pump 34. The concentrate centripetal pump 34 of the exemplary arrangement may also be of a construction like that later discussed in detail. In the exemplary arrangement the concentrate centripetal pump 34 includes inlet openings 36 positioned in a wall that bounds the annular periphery of the centripetal pump. It should be noted that the concentrate centripetal pump 34 has a greater peripheral diameter than the peripheral diameter of the centrate pump. The concentrate pump further includes an annular outlet opening 38. The annular outlet opening 38 is in fluid connection with a concentrate outlet tube 40. The concentrate outlet tube extends in coaxial surrounding relation with the centrate tube 30.

In the exemplary arrangement the inlet openings 36 of the concentrate centripetal pump are positioned in a concentrate pump chamber 42. The concentrate pump chamber is defined by walls of the rotatable assembly 16. During operation, the inlet openings 36 of the concentrate centripetal pump are exposed to concentrate in the concentrate pump chamber 42. The concentrate pump chamber 42 is bounded vertically by a disk shape top portion 44. At least one fluid seal 46 extends between the outer circumference of the outlet tube 40 and the top portion 44. The exemplary seal 46 is configured to reduce the risk of fluid escaping from the interior of the separation chamber and to prevent introduction of contaminants from the exterior area of the core therein.

During operation of the centrifuge, the bowl and the structure including the cavity or separation chamber is rotated about the axis 12 in a rotational direction. Rotation in the rotational direction is operative to separate cell suspension that is introduced through the feed tube 18, into centrate which is discharged through the centrate tube 30 and concentrate which is discharged through the concentrate outlet tube 40.

Cell suspension enters the separation chamber 22 through the tube opening 20 at the bottom of the separation chamber. The cell suspension is moved outwardly via centrifugal force and a plurality of accelerator vanes 48. As the suspension is moved outwardly by the accelerator vanes, the cell suspension material is acted upon by the centrifugal force such that the cell material is caused to be moved outwardly toward the annular tapered wall 50 that bounds the outer side of the separation chamber. The concentrated cellular material is urged to move outwardly and upwardly as shown against the tapered wall 50 and through a plurality of concentrate slots 52. The concentrate material moves upwardly beyond the concentrate slots and into the concentrate pump chamber 42 from which the concentrate is discharged by the concentrate centripetal pump 34.

In the exemplary arrangement, during operation the cell free centrate is positioned in proximity to a vertical annular wall 54 which bounds the inside of the separation chamber 22. The centrate material moves upwardly through centrate holes 56 in the annular base structure that bounds the centrate pump chamber 32. The centrate moves upwardly through the centrate holes 56 and forms a pool of liquid centrate in the centrate chamber. From the centrate chamber, the centrate is moved through operation of the centrate centripetal pump 24 and delivered from the core through the centrate tube 30.

Figure 17:
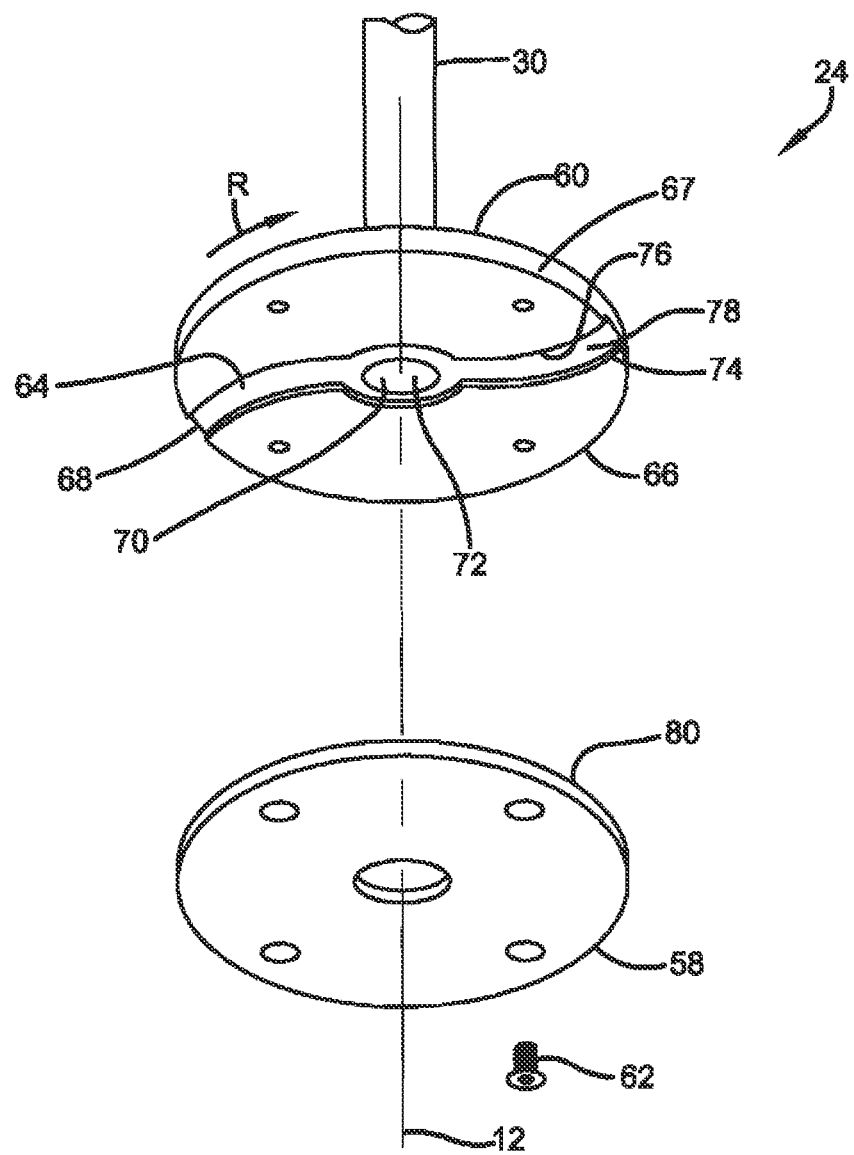
FIG. 17 is an isometric exploded view of an alternative centripetal pump.
Figure 18:
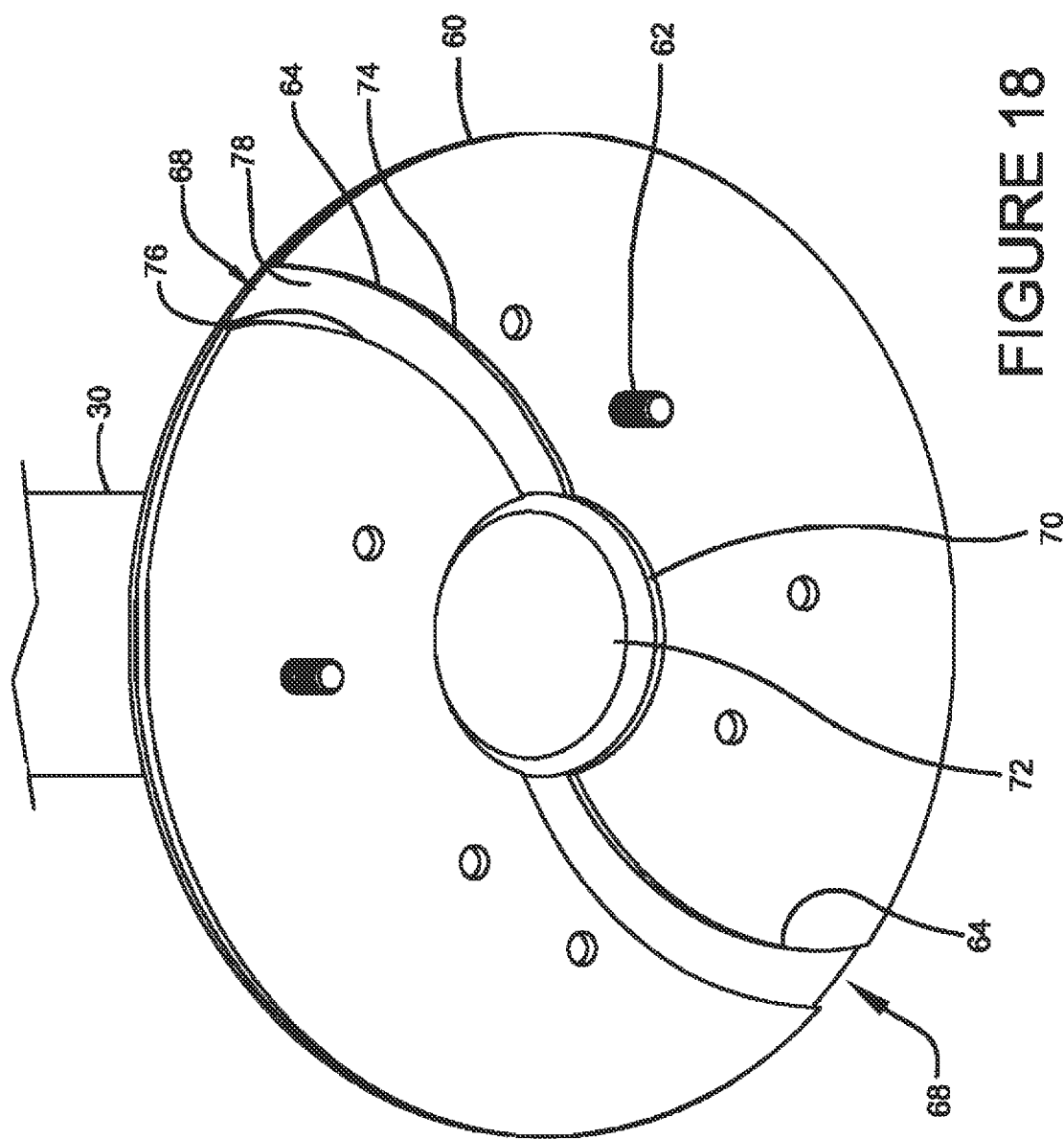
FIG. 18 is an isometric view of a plate of the alternative centripetal pump including the volute passages therein.

In the exemplary arrangement of FIG. 16, the concentrate and centrate pumps may have a configuration generally like that shown in FIG. 17. In FIG. 17, the centrate centripetal pump 24 is represented in an isometric exploded view. As shown in FIG. 17, the exemplary centripetal pump has a disk-shaped body that is comprised of a first plate 58 and a second plate 60. During operation, the first plate and the second plate are held in releasable engaged relation via fasteners which are represented by screws 62. Of course it should be understood that in other arrangements, other configurations and fastening methods may be used.

In the exemplary arrangement, the second plate 60 includes walls that bound three sides of curved volute passages 64. It should be understood that while in the exemplary arrangement, the centripetal pump includes a pair of generally opposed volute passages 64. In other arrangements, other numbers and configurations of volute passages may be used.

In the exemplary arrangement, the first and second plates make up the disk-shaped body of the centripetal pump which has a annular vertically extending wall 67 which defines an annular periphery 66. Inlet openings 68 to the volute passages 64 extend in the annular periphery. An annular collection chamber 70 extends in the body radially outwardly from the axis 12 and is fluidly connected to the volute passages. The annular collection chamber 70 receives the material that enters the inlet openings 68. The annular collection chamber 70 is in fluid connection with an annular outlet opening that is coaxial with the axis 12. In the exemplary arrangement for the centrate centripetal pump, the annular outlet opening is an annular space which extends between the outer wall of feed tube 18 and the inner wall of second plate 60 which outlet is fluidly connected to the centrate outlet tube 30.

In the exemplary arrangement each of the volute passages 64 is configured such that the volute passages are curved toward the rotational direction of the bowl and separation chamber, the rotational direction is represented by Arrow R in FIG. 17. In the exemplary arrangement, the vertically extending walls 74 which bound the volute passages and which face the rotational direction, are each curved toward the rotational direction. The curved configuration of the walls 74 which bound the volute passages horizontally, provide for the enhanced pumping properties of the exemplary arrangement. Further, the opposed bounding wall 76 of each volute passage in the exemplary arrangement has a similar curved configuration. The curved configuration of the vertically extending walls that bound the volute passages horizontally provide for a constant cross-sectional area of each volute passage from the respective inlet to the collection chamber. This consistent cross-sectional area is further achieved through the use of a generally flat wall 78 which extends between walls 74 and 76 and which bounds the volute passage vertically on one side. Further in the exemplary arrangement the first plate 58 includes a generally planar circular face 80 on its side which faces inwardly when the plates are assembled to form the disk-shaped body of the centripetal pump. In this exemplary arrangement, the face 80 serves to vertically bound the sides of both volute passages 64 of the centripetal pump.

Of course it should be understood that this exemplary arrangement which includes a pair of plates, one of which includes a recess with walls which bound three of the four sides of the curved volute passages and the other of which includes a surface that bounds the remaining side of the volute passages is exemplary. It should be understood that in other arrangements, other configurations and structures may be used.

In the exemplary centripetal pump structure shown in FIG. 16, the centripetal pump structures are utilized and have the capability for moving more liquid than comparably sized paring disk-type centripetal pumps. Further, the exemplary configuration produces less heating of the liquid than comparable paring disks.

Further in the exemplary arrangement as previously discussed, the annular periphery of the centrate centripetal pump 24 has a smaller outer diameter than the periphery of the concentrate centripetal pump 34. This configuration is used in the exemplary arrangement to avoid the centrate centripetal pump removing too much liquid from the pool of liquid centrate which forms in the centrate pump chamber 32. Assuring that there is sufficient liquid centrate within the centrate pump chamber, helps to assure that waves do not form in the centrate adjacent to the inlets of the centrate centripetal pump. The formation of waves which could result from less than sufficient liquid centrate, may cause vibration and other undesirable properties of the centrifuge and core.

The larger annular periphery of the concentrate pump of the exemplary arrangement causes material to preferentially flow out of the structure via the concentrate centripetal pump. In exemplary arrangements, the flow of concentrate downstream of the concentrate output tube 40 can be controlled to control the ratio of centrate flow to concentrate flow from the structure.

Further in exemplary arrangements, utilizing centripetal pumps having the configurations described, the properties and flow characteristics of the centrifuge may be tailored to the particular materials and requirements of the separation processing being performed. Specifically the diameters of the annular periphery of the centripetal pumps may be sized so as to achieve optimum properties for the particular processing activity. For example, the larger the diameter of the periphery of the centripetal pump, the greater flow and pressure at the outlet that can be achieved. Further the larger diameter tends to produce greater mixing than a relatively smaller diameter. However, the larger diameter also results in greater heating than a smaller peripheral diameter of a centripetal pump. Thus to achieve less heating, a smaller diameter periphery may be used. Further it should be understood that different sizes, areas and numbers of inlet openings and different volute passage configurations may be utilized to vary flow and pressure properties as desired for purposes of the particular separation process.

Figure 19:
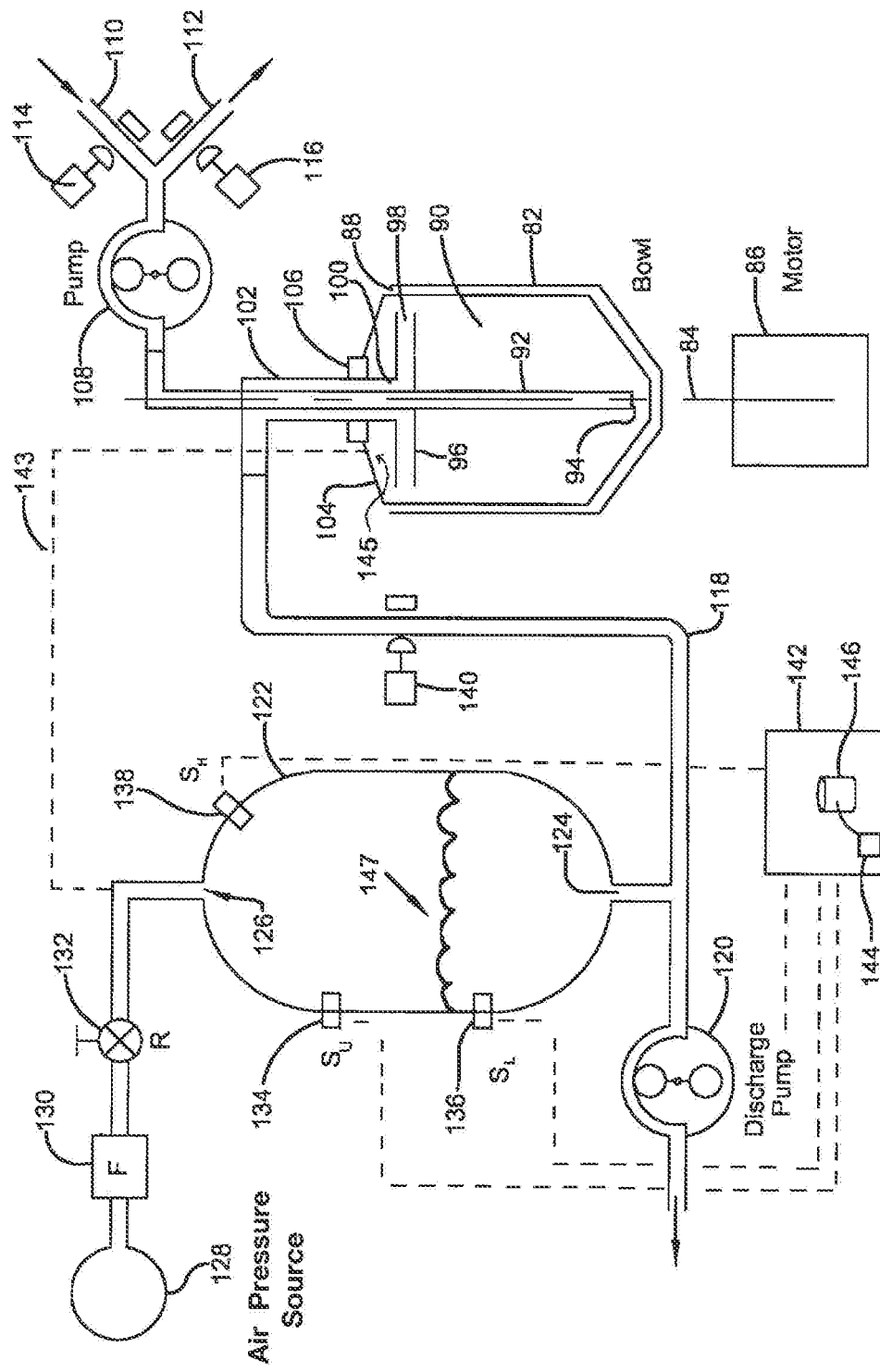
FIG. 19 is a schematic view of a centrifuge system which operates to assure that positive pressure is maintained in the centrifuge core cavity.

FIG. 19 shows schematically an exemplary system which is utilized to help assure positive pressure within a separation chamber which is alternatively referred to herein as a cavity, during cell suspension processing. As discussed in connection with previous exemplary arrangements, it is generally desirable to assure positive pressure above atmospheric pressure at all times within the separation chamber. Doing so reduces the risk that contaminants are introduced into the separation chamber by infiltrating past the one or more fluid seals which operatively extend between the stationary assembly and the rotatable assembly of the core. Further as previously discussed, it is also generally desirable to maintain air at positive pressure within the separation chamber in contact with the interior face of the fluid seal. The presence of an air pocket adjacent the seal avoids the seal coming into contact with the material being processed and further helps to reduce the risk of contaminant introduction into the processed material as well as the escape of any material from the separation chamber.

The exemplary system described in connection with FIG. 19 serves to maintain a consistent positive pressure in the separation chamber and reduces the risk of the introduction of contaminants and the escape of processed material.

As schematically shown in FIG. 19, the centrifuge includes a rotatable bowl 82. The centrifuge bowl is rotatable about an axis 84 by a motor 86 or other suitable rotating device.

The exemplary centrifuge structure shown includes a rotatable single use structure 88 which bounds a cavity 90 which is alternatively referred to herein as a separation chamber.

Like other previously described arrangements, the exemplary structure includes a stationary assembly which includes a suspension inlet feed tube 92 which has an inlet opening 94 positioned adjacent to the bottom area of the cavity. The stationary assembly further includes at least one centripetal pump 96. The centripetal pump of the exemplary arrangement includes a disk-shaped body with at least one pump inlet 98 adjacent the periphery thereof and a pump outlet 100 adjacent the center of the centripetal pump. The pump outlet is in fluid connection with a centrate outlet tube 102. The centrate outlet tube extends in coaxial surrounding relation of the suspension inlet tube in a manner similar to that previously discussed. The rotatable top portion 104 of the fluid containing separation chamber is in operative connection with at least one seal 106 which operates to fluidly seal the cavity of the core with respect to the inlet tube and the outlet tube. The at least one seal 106 extends operatively in sealing relation between the outer annular surface of the centrate outlet tube 102 which is stationary, and the rotatable top portion 104 of the core which has an upper internal wall which internally bounds the cavity 90 as shown.

In the exemplary arrangement the inlet tube 92 is fluidly connected to a pump 108. Pump 108 in an exemplary arrangement is a peristaltic pump which is effective to pump cell suspension without causing damage thereto. Of course it should be understood that this type of pump is exemplary and in other arrangements, other types of pumps may be used. Further in the exemplary arrangement the pump 108 is reversible. This enables the pump 108 to act as a feed pump so as to be able to pump cell suspension from an inlet line 110 and into the inlet tube at a controlled rate. Further in the exemplary arrangement, the pump 108 may operate as a concentrate removal or discharge pump after the cell concentrate has been separated by centrifugal action. In performing this function, the pump 108 operates to pump cell concentrate out of the separation chamber by reversing the flow of material in the inlet tube 92 from that when cell suspension is fed into the separation chamber. The cell concentrate is then pumped to a concentrate line 112. As represented in FIG. 19, the inlet line 110 and concentrate line 112 can be selectively opened and closed by valves 114 and 116 respectively. In the exemplary arrangement, valves 114 and 116 comprise pinch valves which open and close off flow through flexible lines or tubing. Of course it should be understood that this approach is exemplary and in other arrangements, other approaches may be used.

In the exemplary system, the centrate outlet tube 102 is fluidly connected to a centrate discharge line 118. The centrate discharge line is fluidly connected to a centrate discharge pump 120. In the exemplary arrangement, the centrate discharge pump 120 is a variable flow rate pump which can have the flow rate thereof selectively adjusted. For example in some exemplary arrangements, the pump 120 may include a peristaltic pump which includes a motor, the speed of which may be controlled so as to selectively increase or decrease the flow rate through the pump. The outlet of the centrate discharge pump delivers the processed centrate to a suitable collection chamber or other processing device.

In the exemplary arrangement schematically represented in FIG. 19, a pressure damping reservoir 122 is fluidly connected to the centrate discharge line 118 fluidly intermediate of the centrate outlet tube 102 and the pump 120. In the exemplary arrangement, the pressure damping reservoir includes a generally vertically extending vessel with an interior area configured for holding liquid centrate in fluid tight relation. The pressure damping reservoir includes a bottom port 124 which is fluidly connected to the centrate discharge line 118.

On an opposed side of the reservoir 122 is a top port 126. The top port is exposed to air pressure. In the exemplary arrangement, the top port is exposed to air pressure from a source of elevated air pressure schematically indicated 128. In exemplary arrangements, the source of elevated pressure may include a compressor, an air storage tank or other suitable device for providing a source of elevated air pressure above atmospheric pressure within the range needed for operation of the system. Air from the source of elevated pressure 128 is passed through a sterile filter 130 to remove impurities therefrom. A regulator 132 is operative to maintain a generally constant air pressure level above atmospheric at the top port of the pressure damping reservoir. In exemplary arrangements, the air pressure regulator comprises an electronic fast acting regulator to help assure that the generally constant air pressure at the desired level is maintained. The exemplary fast acting regulator 132 operates to rapidly increase the pressure acting at the top port 126 when the pressure falls below the desired level, and relieves pressure rapidly through the regulator in the event that the pressure acting at the top port is above the set value of the regulator.

In some arrangements the regulator outlet may also be in operative fluid connection with the interior of the top portion 104 of the separation chamber through an air line 143 shown schematically in phantom. In such exemplary arrangements the outlet pressure of the regulator that acts on the top port 126 of the reservoir also acts through the air line 143 on the air pocket inside of the separation chamber which extends downward to a level in the cavity above the centripetal pump inlet and on the interior of the at least one seal 106 and radially from a region proximate to the axis 84 to the upper internal wall on the inside of the top portion 104. In the exemplary arrangement the line 143 applies the positive pressure to the area within the separation chamber below the at least one seal through at least one segregated passage that extends through the stationary structures of the assembly which includes the centrate outlet tube 102 and the inlet feed tube 92. The at least one exemplary segregated passage of the air line 143 applies the air pressure to the interior of the top portion 104 through at least one air opening 145 to the separation chamber. The exemplary at least one opening 145 is positioned outside the exterior surface of the outlet tube 102, above the inlet 98 to the centripetal pump and below the at least one seal 106. Of course it should be understood that this described structure for the exemplary air line that provides positive air pressure to the air pocket in the separation chamber and on the inner side of the at least one seal is exemplary, and in other arrangements, other structures and approaches may be used.

In the exemplary arrangement of the pressure damping reservoir 122, an upper liquid level sensor 134 is configured to sense liquid centrate within the interior of the pressure damping reservoir. The upper liquid level sensor is operative to sense liquid at an upper liquid level. A lower liquid level sensor 136 is positioned to sense liquid in the reservoir at a lower liquid level. A high liquid level sensor 138 is positioned to detect a high liquid level in the reservoir above the upper liquid level. The high liquid level sensor is positioned so as to sense a liquid level at an unacceptably high level so as to indicate an abnormal condition which may require shutting down the system or taking other appropriate safety actions. In the exemplary arrangement, the liquid level sensors 134, 136 and 138 comprise capacitive proximity sensors which are suitable for sensing the level of the liquid centrate adjacent thereto within the pressure damping reservoir. Of course it should be understood that these types of sensors are exemplary and in other arrangements, other sensors and approaches may be used.

The exemplary arrangement further includes other components as may be appropriate for the operation of the system. This may include other valves, lines, pressure connections or other suitable components for purposes of carrying out the processing and handling of the suspension, centrate and concentrate as appropriate for the particular system. This may include additional valves such as valve 140 shown schematically for controlling the open and closed condition of the centrate discharge line 118. The additional lines, valves, connections or other items included may vary depending on the nature of the system.

The exemplary system of FIG. 19 further includes at least one control circuit 142 which may be alternatively referred to as a controller. The exemplary at least one control circuit 142 includes one or more processors 144. The processor is in operative connection with one or more data stores schematically indicated 146. As used herein, a processor refers to any electronic device that is configured to be operative via processor executable instructions to process data that is stored in the one or more data stores or received from external sources, to resolve information, and to provide outputs which can be used to control other devices or carry out other actions. The one or more control circuits may be implemented as hardware circuits, software, firmware or applications that are operative to enable the control circuitry to receive, store or process data and to carry out other actions. For example the control circuits may include one or more of a microprocessor, CPU, FPGA, ASIC or other integrated circuit or other type circuit that is capable of performing functions in the manner of an electronic computing device. Further it should be understood that data stores may correspond to one or more of volatile or nonvolatile memory devices such as RAM, flash memory, hard drives, solid state devices, CDs, DVDs, optical memory, magnetic memory or other circuit readable mediums or media upon which computer executable instructions and/or data may be stored.

Circuit executable instructions, may include instructions in any of a plurality of programming languages and formats including, without limitation, routines, subroutines, programs, threads of execution, objects, methodologies and functions which carry out the actions such as those described herein. Structures for the control circuits may include, correspond to and utilize the principles described in the textbook entitled Microprocessor Architecture, Programming, and Applications with the 8085 by Ramesh S. Gaonker (Prentice Hall, 2002), which is incorporated herein by reference in its entirety. Of course it should be understood that these control circuit structures are exemplary and in other arrangements, other circuit structures for storing, processing, resolving and outputting information may be used.

In the exemplary arrangement, the at least one control circuit 142 is in operative connection through suitable interfaces with at least one sensor such as sensors 134, 136 and 138. The at least one control circuit is also in operative connection with the variable flow rate discharge pump 120. Further in some exemplary arrangements, the at least one control circuit may also be in operative connection with other devices such as motor 86, pump 108, regulator 132, air pressure source 128, the fluid control valves and other devices.

The exemplary at least one control circuit is operative to receive data and control such devices in accordance with circuit executable instructions stored in the data store 146. In the exemplary arrangement, the fluid level 147 in the fluid damping reservoir is a property that corresponds to pressure in the centrate discharge tube 102. In one exemplary implementation which does not utilize air line 143, the fact that the pressure in the centrate discharge tube is indicative of the pressure in the top portion 104 of the structure and the nature of the pressure in the separation chamber adjacent to the seal 106 is utilized to control the operation of the discharge pump and other components. As previously discussed, it is desirable to maintain a positive pressure above atmospheric pressure and a pocket of air adjacent to the at least one seal within the separation chamber to avoid the introduction of contaminants into the separation chamber which could result from negative pressure. However, if the fluid level becomes too high within the separation chamber, the pressure and the suspension material being processed may overflow the seal which may result in potential contamination and undesirable exposure and loss of processed material. This may result from conditions where the back pressure on the centrate line which is in connection with the outlet from the centripetal pump is too high.

In the exemplary arrangement the bowl speed produces a corresponding pumping force and a pump output pressure level of the centripetal pump. This pump output pressure level of the centripetal pump varies with the rotational speed of the bowl and the core. The exemplary arrangement without the use of air line 143 provides for a back pressure to be controlled on the centrate outlet tube. Back pressure is provided by controlling the speed of a motor operating the pump 120 and the liquid level 147 in the pressure damping reservoir. The back pressure is maintained so as to be less than the pump output pressure level (so that the centripetal pump may deliver centrate out of the separation chamber) but is maintained at a positive pressure above atmospheric so as to assure that contaminants will not infiltrate into the separation chamber past the seal, and so that air at elevated pressure is maintained in the interior of the separation chamber adjacent to the seal so as to isolate the seal from the components of the suspension being processed.

In the exemplary arrangement the elevated pressure applied to the top port 126 of the pressure damping reservoir is maintained by the regulator 132. Further by the at least one control circuit 142 controlling the speed of pump 120 to maintain the liquid level 147 between the upper liquid level as sensed by the sensor 134 and the lower liquid level 136, centrate flow out of the separation chamber is controlled so that the pressure of the top area of the separation chamber is maintained at a desired constant value and the centrate does not contact or overflow the seal.

In an alternate arrangement with the use of air line 143, the positive pressure level of the regulator acts on both the fluid in the reservoir 122 and the area of the separation chamber above the centripetal pump inlet. Because the positive pressure level of air applied in both locations is the same, the back pressure on the centrate discharge line (which is the pressure applied above the fluid in the reservoir) is virtually always the same as the pressure in the air pocket at the top of the separation chamber. This enables the centripetal pump to operate without any net effect from either pressure.

In this exemplary arrangement the pump 120 and other system components are controlled responsive to the at least one control circuit 142 to assure that there is an adequate volume of air within the interior of the reservoir 122 at all times during centrate production. This assures that the reservoir provides the desired damping effect on changes in centrate discharge line pressure that might otherwise be caused by the pumping action of pump 120. This is done by maintaining the liquid in the reservoir 122 at no higher than the upper liquid level detected by sensor 134. Further, the liquid level in the reservoir is controlled to be maintained above the lower liquid level as sensed by sensor 136. This assures that the centripetal pump is not pumping air and aerating the centrate.

In the exemplary arrangement the centrate flow out of the separation chamber is controlled through operation of the at least one control circuit. The exemplary control circuitry may operate the system during processing conditions to maintain the incoming flow of cell suspension by pump 108 to the separation chamber 90 at a generally constant rate, while the separation process is occurring with the motor 86 operating to maintain the constant bowl speed to achieve the separation of the centrate and the cell concentrate. The exemplary arrangement further operates to maintain an ideally constant back pressure on the centrate discharge line from the centripetal pump while maintaining air in the separation chamber above the level of the lower side of the air pocket to isolate the at least one seal 106 from the centrate and concentrate material being processed.

In an exemplary arrangement, the pressure maintained through operation of the regulator in the pressure damping reservoir is set at approximately 2 kpa (0.29 psi) above atmospheric. In the exemplary system this pressure has been found to be suitable to assure that the seal integrity and isolation is maintained during all stages of cell suspension processing. Of course it should be understood that this value is exemplary and in other arrangements, other pressure values and pressure damping reservoir configurations, sensors and other features may be utilized.

Figure 20:
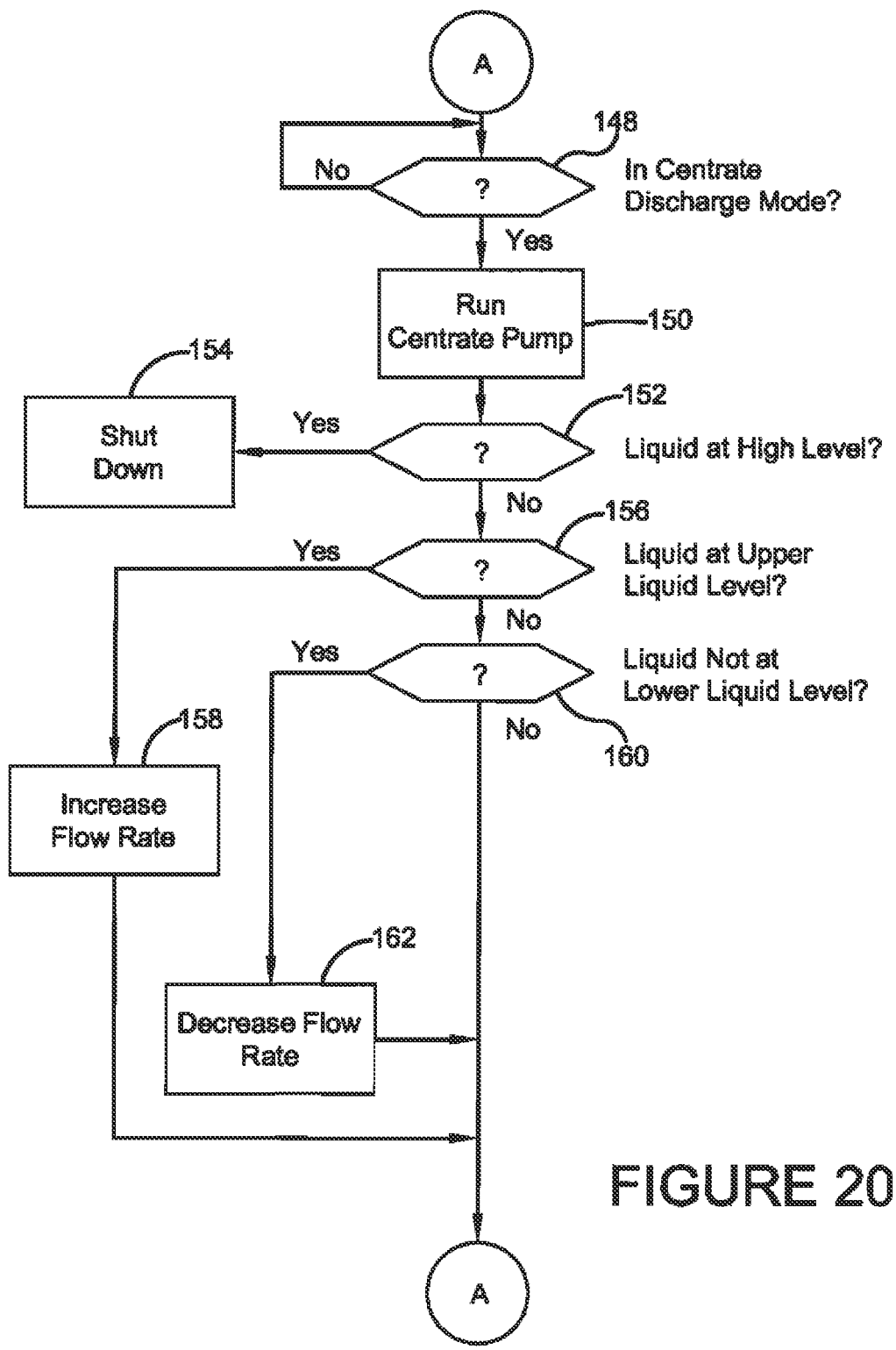
FIG. 20 is a schematic view showing simplified exemplary logic flow executed by at least one control circuit of the system shown in FIG. 19.

FIG. 20 shows schematically exemplary logic executed through operation of the at least one control circuit 142 in connection with maintaining the desired pressure level in the centrate discharge tube and within the top portion of the separation chamber. It should be understood that the control circuits in some exemplary arrangements may perform numerous additional or different functions other than those represented. These functions may include the overall control of the different processes and steps for operation of the centrifuge in addition to the described pressure control function. As represented in FIG. 20, in an initial subroutine step 148, the at least one control circuit 142 is operative to make a determination on whether the centrifuge operation is currently in a mode where centrate is being discharged from the separation chamber. If so, the at least one control circuit is operative to cause the centrate discharge pump 120 to operate to discharge centrate delivered through the centrate discharge line 118. This may be done by causing operation of a motor of the pump. In the exemplary arrangement, the flow rate of the pump 120 may be a set value initially or alternatively may be varied depending on particular operating conditions that are determined through control circuit operation during the process. The operation of the centrate discharge pump is represented by a step 150.

The at least one control circuit is then operative to determine in a step 152 whether liquid is sensed at the high level of the high liquid level sensor 138. If so, this represents an undesirable condition. If liquid is sensed at the level of the sensor 138, the control circuit then operates to take steps to address the condition. This may include operating the pump 120 to increase its flow rate and making subsequent determinations if the level drops within a period of time while the centrifuge continues to operate. Alternatively or in addition, the at least one control circuit may decrease the speed of pump 108 to reduce the flow of incoming material. If such action does not cause the level to drop within a set period of time, additional steps are taken. Such steps may also include slowing or stopping rotation of the bowl 182. Such actions may also include stopping the operation of pump 108 so as to avoid the introduction of more suspension material into the separation chamber. These steps which are generally referred to as shutting down normal operation of the system are represented by a step 154.

If liquid is not sensed at the level of the high level sensor 138, the at least one control circuit is next operative to determine if liquid is sensed at the upper liquid level of sensor 134. This is represented by step 156. If liquid is sensed at the upper liquid level sensor, the at least one circuit operates responsive to its stored instructions to increase the speed and therefore the flow rate of discharge pump 120. This is done in an exemplary arrangement by increasing the speed of the motor that is a part of the pump. This is represented by a step 158. Increasing the flow rate of the pump causes the liquid level 147 in the pressure damping reservoir to begin to drop as more liquid is moved by the pump 120.

If in step 156 liquid is not sensed at the upper liquid level of sensor 134, the at least one control circuit then operates to make a determination as to whether liquid is not sensed at the lower liquid level of sensor 136. This is represented by step 160. If the liquid level is not at the level of the sensor 136, the control circuitry operates in accordance with its programming to control the pump 120 to decrease its flow rate. This is done in an exemplary arrangement by slowing the speed of the motor. This is represented by a step 162. In the exemplary arrangement, slowing the flow rate of the pump 120 causes the liquid level 147 to begin rising in the pressure damping reservoir. In some exemplary arrangements if the level does not rise within the reservoir within a given time, the control circuitry may operate in accordance with its programming to cause additional actions, such as actions associated with shut down step 154 previously discussed. The control circuitry of exemplary arrangements may operate to change the pumping rate of pump 120 to maintain the level 147 within the pressure damping reservoir at a generally constant level between the levels of sensors 134 and 136 during centrate production.

In the exemplary arrangement, maintaining the generally constant elevated pressure of sterile air over the liquid in the pressure damping reservoir helps to assure that a similar elevated pressure is consistently maintained in the centrate outlet line and at the seal within the separation chamber. Further in the exemplary arrangements, the pressure is enabled to be controlled at the desired level during different operating conditions of the centrifuge during which the bowl rotates at different speeds. This includes, for example, conditions during which the separation chamber is initially filled at a relatively high rate through the introduction of cell suspension and during which the centrifuge rotates at a relatively lower speed. Pressure can also be maintained during the subsequent condition of final fill in which the flow rate of cell suspension into the separation chamber occurs at a slower rate and during which the rotational speed of the bowl is increased to a higher rotational speed. Further, positive pressure is maintained as previously discussed during the feeding of the suspension into the bowl and during discharge of the centrate from the separation chamber. Further in exemplary arrangements, the at least one control circuit may operate to also maintain the positive pressure during the time period that the concentrate is removed by having it pumped out of the separation chamber. Maintaining positive pressure within the separation chamber during all of these conditions reduces the risk of contamination and other undesirable conditions which otherwise might arise due to negative pressure (below atmospheric pressure) conditions.

Of course it should be understood that the features, components, structures and control methodologies are exemplary, and in other arrangements other approaches may be used. Further, although the exemplary arrangement includes a system which operates in a batch mode rather than a mode in which both centrate and concentrate are continuously processed, the principles hereof may also be applied to such other types of systems.

While the pressure damping reservoir is useful in exemplary arrangements to help assure that a desired pressure level is maintained in the outlet tube and the separation chamber, other approaches may also be utilized in other exemplary arrangements. For example, in some arrangements pressure may be directly sensed and/or applied in the outlet tube, the separation chamber or in other locations which correspond to the pressure in the separation chamber. In some arrangements, the flow rate of the discharge pump may be controlled so as to maintain the suitable pressure level. In still other arrangements, exemplary control circuits may be operative to control both the discharge pump and a pump that feeds suspension into the core and/or suitable valving or other flow control devices so as to maintain suitable pressure levels. Such alternative approaches may be desirable depending on the particular centrifuge device being utilized and the type of material being processed.

Figure 21:
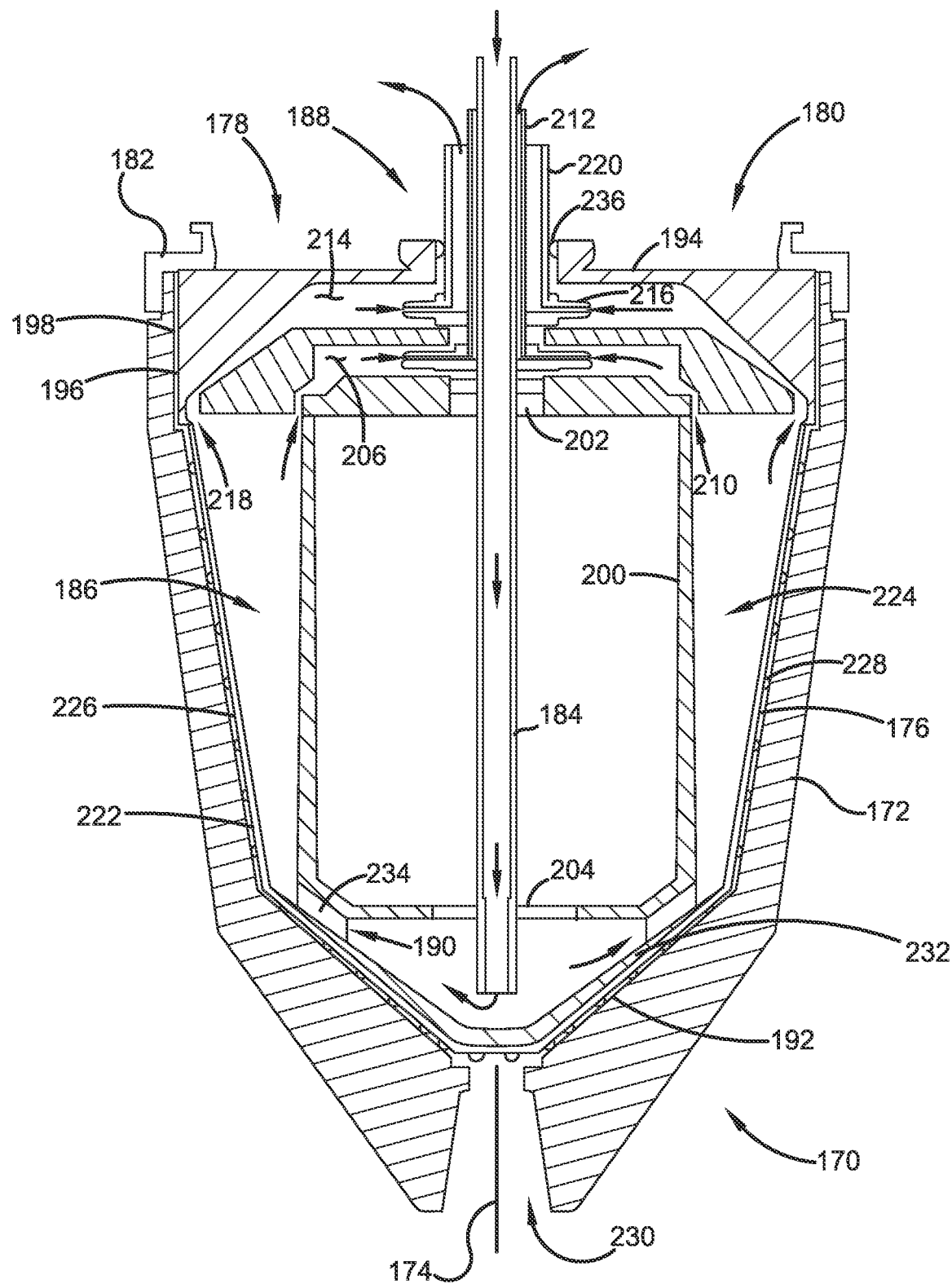
FIG. 21 is a cross-sectional schematic view of an alternative continuous centrate and concentrate discharge centrifuge system.

FIG. 21 shows schematically an alternative centrifuge system 170 particularly configured to separate cells in a cell culture into cell centrate and cell concentrate on a continuous or semi-continuous basis. The exemplary system shows a rigid centrifuge bowl 172 that is rotatable about an axis 174. The bowl includes a cavity 176 configured for releasably receiving a single use structure 178 therein. The rigid bowl includes an upper opening 180. An annular securing ring or other securing structure schematically represented 182 enables releasably securing the single use structure 178 within the bowl cavity.

The exemplary single use structure 178 of this example includes a central axially extending feed tube 184. As later discussed the feed tube is used to deliver the cell culture material into the interior area 186 of the single use structure 178. The feed tube 184 extends from an upper portion at a first axial end 188 of the single use device, to an opening 190 which is in the interior area at a lower portion at a second axial end 192. The single use structure 178 includes a substantially disc shape portion 194 adjacent the upper first axial end. Exemplary disc shape portion 194 is generally rigid which means that it is rigid or semi-rigid, and includes an annular outer periphery 196. The annular outer periphery is configured to engage the upper annular bounding wall 198 of the centrifuge bowl cavity 176. The annular outer periphery of the disc shape portion 194 is configured to engage the rigid bowl 172 so that the single use structure is rotated therewith.

The exemplary single use structure 178 further includes a hollow rigid or at least semi-rigid cylindrical core 200. Core 200 is operatively engaged with the disc shape portion 194 and is rotatable therewith. The core 200 is axially aligned with the disc shape portion and extends axially intermediate of the upper portion and the lower portion of the single use structure. The core 200 includes an upper opening 202 and a lower opening 204 through which the feed tube 184 extends.

Disc shape portion 194 includes a substantially circular centrate centripetal pump chamber 206. A centrate centripetal pump 208 is positioned in chamber 206. A substantially annular centrate opening 210 is in fluid connection with the centrate pump chamber 206. By substantially annular it is meant that the opening may be comprised of discrete openings in an annular arrangement as well as a continuous opening. Centrate centripetal pump 208 is in fluid connection with a centrate discharge tube 212. Centrate discharge tube 212 extends in coaxial surrounding relation of feed tube 184. The centrate discharged passes through the substantially annular opening at the periphery of the centrate centripetal pump and through the annular space in the centrate discharge tube 212 on the outside of the feed tube.

Disc shape portion 194 further includes a concentrate centripetal pump chamber 214. Concentrate centripetal pump chamber 214 is a substantially circular chamber that is positioned above centrate centripetal pump chamber 206. Concentrate centripetal pump chamber 214 has a concentrate centripetal pump 216 positioned therein. The concentrate centripetal pump is in fluid connection with a concentrate discharge tube 220. The concentrate discharge tube 220 extends in annular surrounding relation of the centrate discharge tube 212. Concentrate passes through the substantially annular opening at the periphery of the concentrate centripetal pump and through the annular space in the concentrate discharge tube 220 on the outside of the centrate discharge tube.

A substantially annular concentrate opening 218 is in fluid connection with the concentrate pump chamber 214. In the exemplary arrangement the substantially annular concentrate opening and the substantially annular centrate opening are concentric coaxial openings with the concentrate opening disposed radially outward of the centrate opening. Of course this arrangement is exemplary and in other arrangements other approaches and configurations may be used.

The exemplary single use structure 178 further includes a flexible outer wall 222. Flexible outer wall 222 is a continuous annular fluid tight wall that in the operative position of the exemplary single use structure 178 extends in operatively supported engagement with the wall bounding the rigid bowl cavity 176. In the exemplary arrangement the flexible outer wall 222 is operatively engaged in fluid tight connection with the disc shape portion 194. The flexible outer wall has an internal truncated cone shape with a smaller inside radius adjacent to the lower portion of the single use structure which is adjacent to the second axial end 192.

The exemplary flexible outer wall 222 extends in surrounding relation of at least a portion of the core 200. Wall 222 further bounds an annular separation chamber 224. The separation chamber 224 extends radially between the outer wall of core 200 and a radially inner surface of the flexible outer wall 222. The substantially annular concentrate opening 218 and the substantially annular centrate opening 210 are each in fluid communication with the separation chamber 224.

In the exemplary arrangement the flexible outer wall 222 has a textured outer surface 226. The textured outer surface is configured to enable air to pass out of the space between the surface bounding the cavity of the rigid bowl 172 and the flexible outer wall 222. In an exemplary arrangement the textured outer surface may include substantially the entire area of the flexible outer wall that contacts the rigid bowl. In exemplary arrangements the textured outer surface may include one or more patterns of outward extending projections or dimples 228 with spaces or recesses therebetween to facilitate the passage of air. Air may pass out of the bowl cavity 176 when the single use structure 178 is positioned therein either through the upper opening 180 or through a lower opening 230. In exemplary arrangements the projections may be comprised of resilient deformable material that can decrease in height responsive to force of the liner against the rigid wall of the bowl. The textured outer surface 226 of the flexible outer wall 222 reduces the risk that air pockets will be trapped between the rigid bowl of the centrifuge and the single use structure. Such air pockets may cause irregularities in wall contour which may create imbalances and/or change the contour of the separation chamber in a way that adversely impacts the separation processes. Of course it should be understood that the air release structures described are exemplary and other arrangements other air release structures may be used.

The exemplary single use structure shown in FIG. 21 further includes a lower rigid or semi-rigid disc shape portion 232. The rigid or semi-rigid material operates to maintain its shape during operation. In the exemplary arrangement lower disc shape portion 232 has a conical shape and is in operative attached connection with the lower end of core 200 by vertically extending wall portions or other structures. A plurality of angularly spaced fluid passages 234 extend between the upper surface of disc shape portion 232 and the radially outward lower portion of the core. Fluid passages 232 extend radially outward and upwardly relative to the bottom of the second axial end 192, and enable the cells in the cell culture batch material that enters the interior area 186 through the opening 190 in feed tube 184, to pass radially outwardly and upwardly into the separation chamber 224.

In the exemplary arrangement the flexible outer wall 222 extends below the lower disc shape portion 232 at the second axial end 192 of the single use structure. The flexible outer wall 222 extends intermediate of the lower disc shape portion 232 and the wall surface of the rigid bowl 172 which bounds the cavity in which the single use structure is position.

In the exemplary arrangement the feed tube 184, centrate discharge tube 212 and concentrate discharge tube 220, as well as with centrate centripetal pump 208 and concentrate centripetal pump 216 remain stationary while the centrifuge bowl 172 and the upper disc shape portion 194, lower disc shape portion 232 and flexible outer wall 222 rotate relative thereto with the bowl. At least one annular resilient seal 236 extends in sealing engagement operatively between the outer surface of the concentrate discharge tube 220 and the upper disc shape portion 194. The at least one seal 236 maintains an air tight seal in a manner like that previously discussed, so that an air pocket may be maintained in the interior area 186 during cell processing so as to isolate the seal from the cell culture material being processed. The air pocket maintained within the interior area of the single use structure is configured such that the centrate centripetal pump 208 and the concentrate centripetal pump 216 remain in fluid communication with the cell culture batch material. In a manner like that previously discussed, a positive pressure may be maintained within the interior area so as to assure that an air pocket is present to adequately isolate the at least one seal 236 from the cell culture batch material being processed. Alternatively, other approaches may be utilized for purposes of maintaining the isolation of the seal from the material being processed.

The exemplary system 170 operates in a manner like that previously discussed. Cells in a cell culture batch material are introduced to the interior area 186 of the single use structure 178 through the feed tube 184. The cells enter the interior area 186 through the feed tube opening 190 at the lower axial end of the single use structure. Centrifugal forces cause the cells to move outwardly through the openings 234 and into the separation chamber 224. The outwardly and upwardly tapered outer wall 222 causes the cells or cell material containing cell concentrate to collect adjacent to the radially outward and upper area of the separation chamber 224. The generally cell free centrate collects in the separation chamber radially inward adjacent to the outer wall of the core 200.

In the exemplary arrangement the cell centrate passes upwardly through the substantially annular centrate opening into the centrate pump chamber. The centrate passes inward through the substantially annular opening of the centrate centripetal pump and then upwardly through the centrate discharge tube 212. At the same time the cell concentrate passes through the substantially annular concentrate opening 218 and into the concentrate centripetal pump chamber 214. The cell concentrate passes inwardly through the substantially annular opening of the concentrate centripetal pump 216 and then upwardly through the concentrate discharge tube 220. This exemplary configuration enables the exemplary system 170 operate on a continuous or semi-continuous basis. The operation of the system 170 may be controlled in a manner like that later discussed so as to facilitate reliable extended operation of the system and delivery of the desired cell concentrate and generally cell free centrate in separate output fluid streams.

Figure 22:
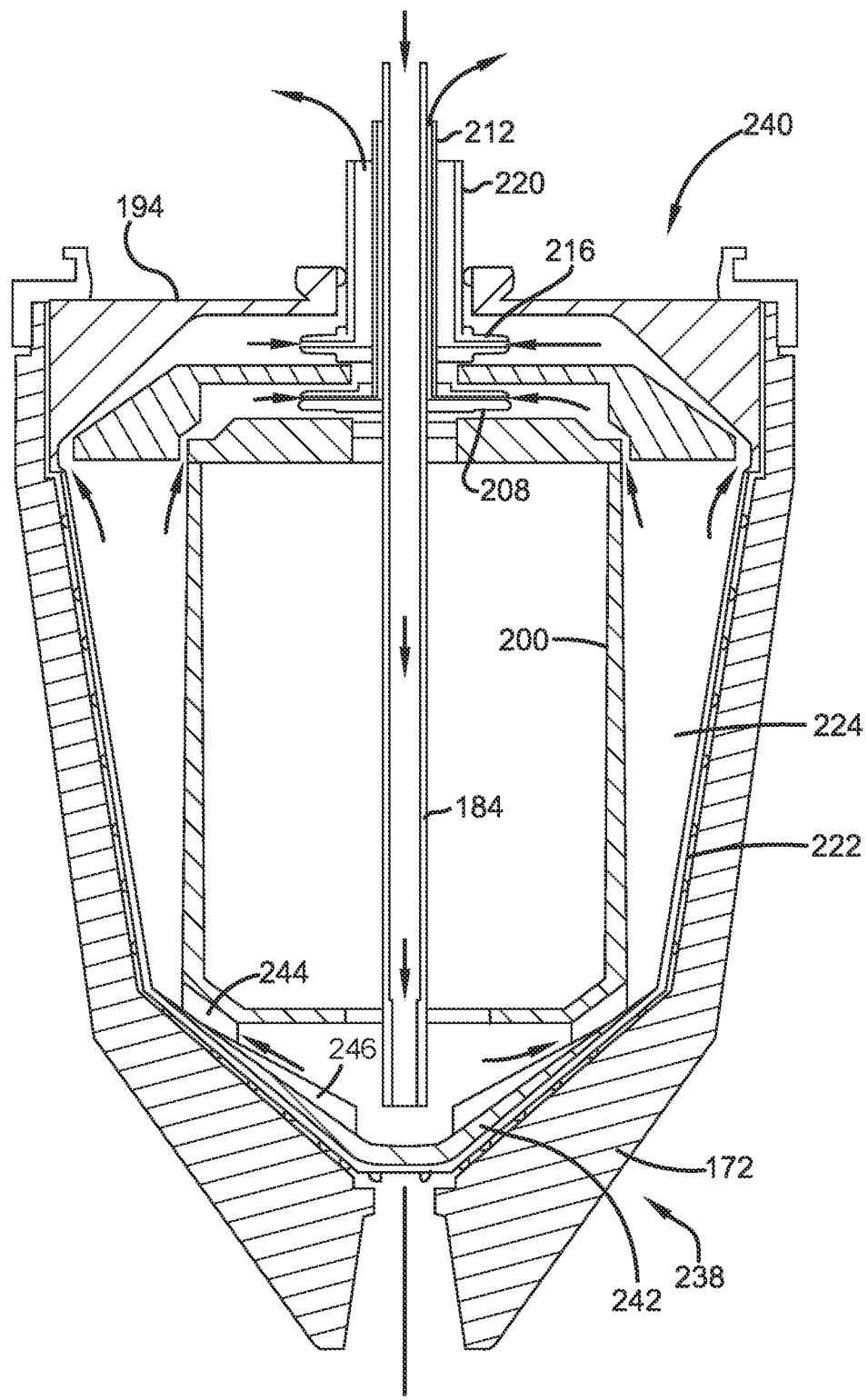
FIG. 22 is a cross-sectional schematic view of a further alternative continuous centrate and concentrate discharge centrifuge system.

FIG. 22 shows an alternative centrifuge system generally indicated 238. System 238 has a single use structure 240. Single use structure 240 is similar in most respects the single use structure 178 previously described. Some of the structures and features of single use structure 240 that are generally the same as those described in connection with single use structure 178 are labeled with the same reference numerals as those used to describe single use structure 178.

Single use structure 240 differs from single use structure 178 in that it includes a rigid or semi-rigid lower disc shape portion 242. Lower disc shape portion 242 is a generally cone shape structure that is in operative connection with the lower end of core 200. A plurality of radially outward and upward extending fluid passages 244 extend between the lower end of the core 200 and the lower disc shape portion 242. The exemplary lower disc shape portion 242 further includes a plurality of angularly spaced radially extending vanes 246. A fluid passage extends radially outward between each immediately angularly adjacent pair of vanes 246. In this exemplary arrangement the vanes 246 extend upwardly from a bottom portion of disc shape portion 242 and at least some are in operative engagement with the core at radially outer portions thereof. In the exemplary arrangement the vanes 246 accelerate the cell culture batch to facilitate movement and separation within the interior area of the single use structure.

Figure 23:
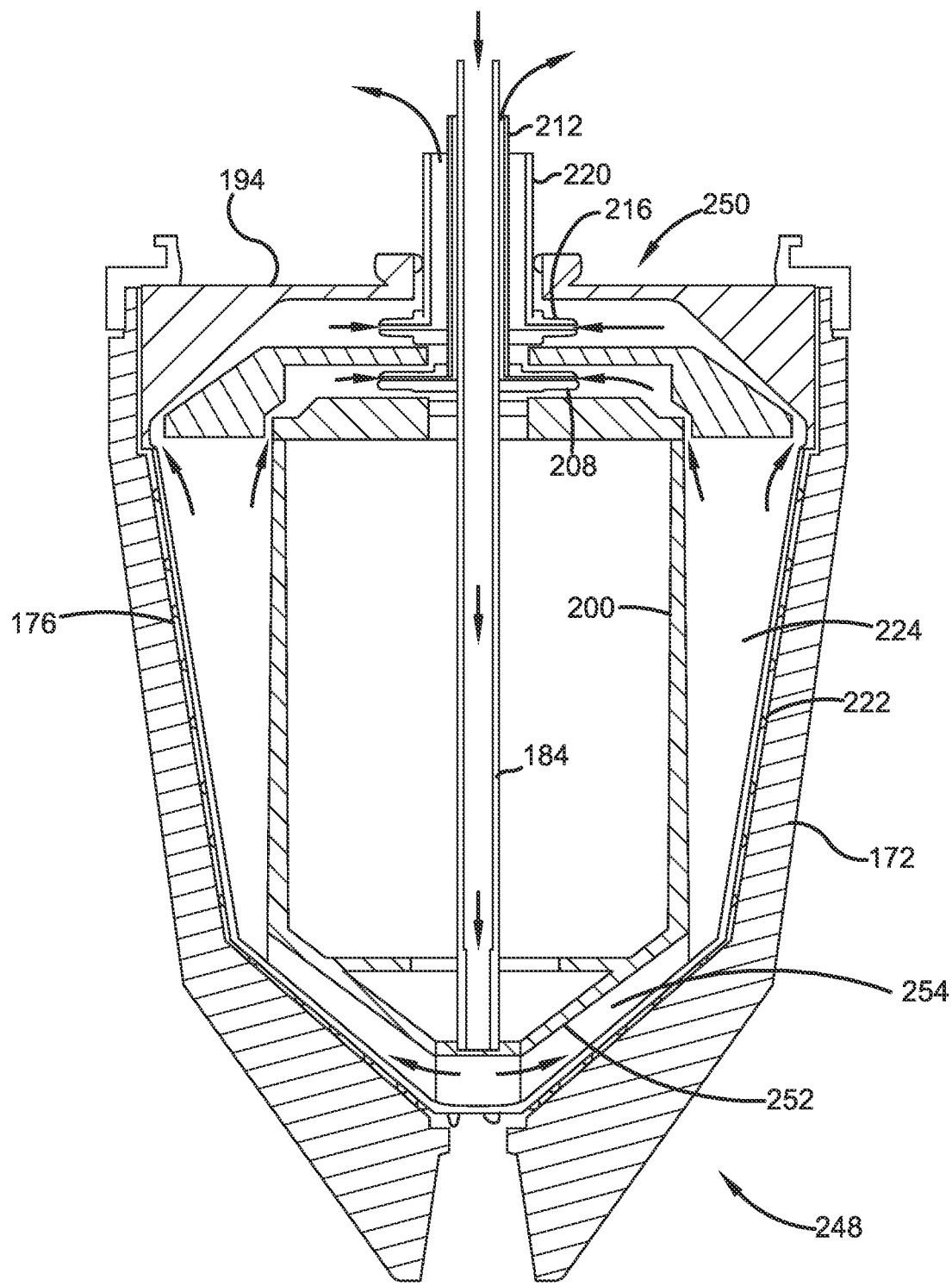
FIG. 23 is a cross-sectional schematic view of a further alternative continuous centrate and concentrate discharge centrifuge system.

An alternative exemplary arrangement of a centrifuge system 248 is shown in FIG. 23. This exemplary arrangement includes a single use structure 250. Single use structure 250 is similar in many respects to the previously described single use structure 178. Some of the structures and features that are like those in the previously described single use structure 178 are labeled on single use structure 250 with the same reference numbers.

The exemplary single use structure 250 differs from single use structure 178 in that it includes a lower disc shape portion 252. Lower disc shape portion 252 is a rigid or semi-rigid cone shape structure that is in operatively attached connection with the core 200 via wall portions or other suitable structures. Lower disc shape portion 252 includes a plurality of angularly spaced radially outward extending accelerator vanes 254. Accelerator vanes 254 extend downwardly from a lower conical side of disc shape portion 252. Each immediately angularly adjacent pair of vanes 254 has a fluid passage extending therebetween. In this exemplary arrangement the flexible outer wall 222 extends in intermediate relation between the lower ends of the vanes 254 and the wall of the rigid bowl 172 bounding the cavity 176. This exemplary configuration provides a submerged accelerator which is operative to accelerate the cell culture batch material so as to facilitate the separation thereof within the interior area of the single use structure. Of course it should be understood that the single use structural features described herein may be combined in different arrangements so as to facilitate the separation of different types of materials and substances with different properties and to achieve desired output fluid streams.

Figure 26:
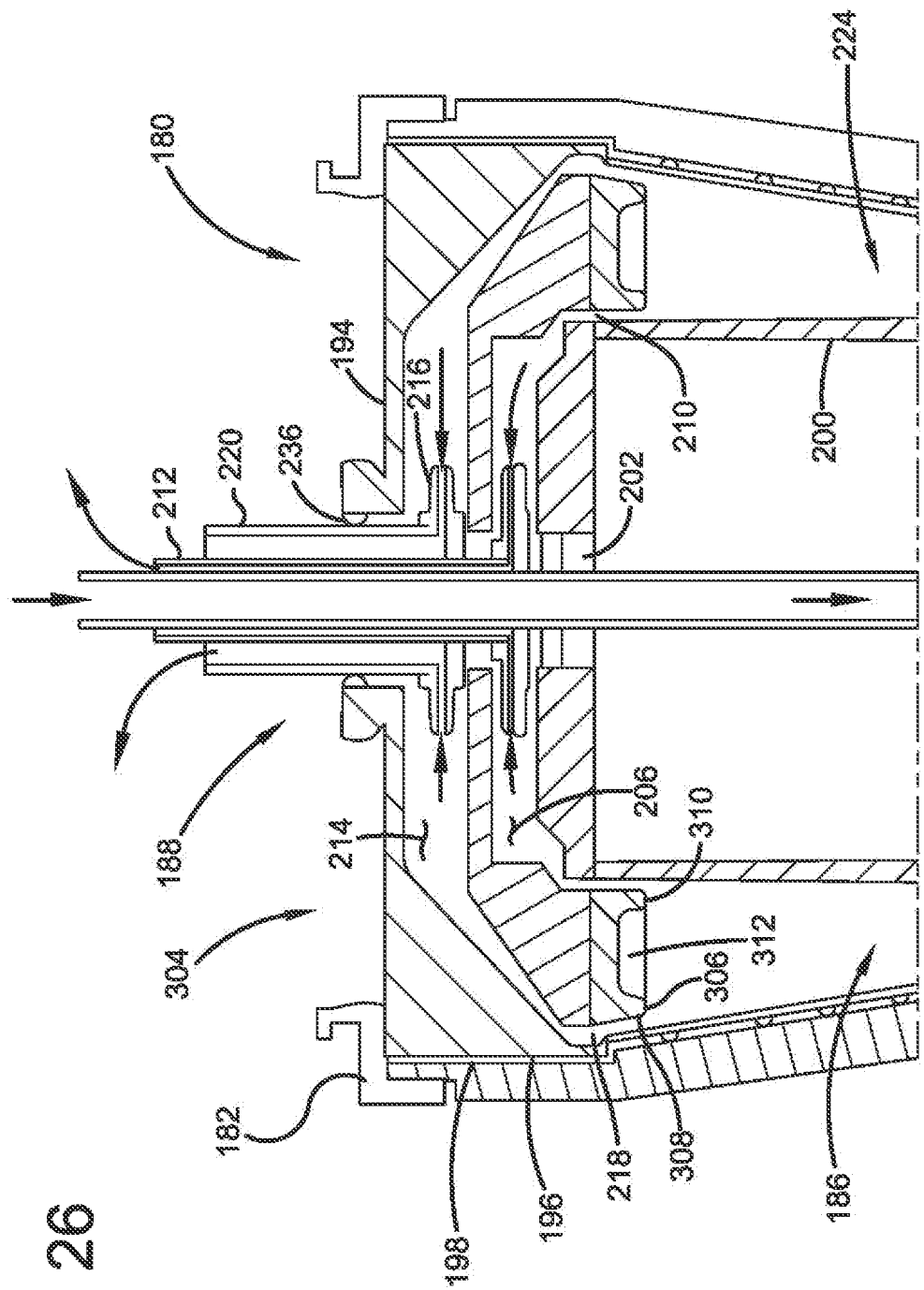
FIG. 26 is a cross-sectional view of an exemplary upper portion of a single use centrifuge structure that includes concentrate and centrate dams in the separation chamber.

FIG. 26 shows an alternative single use structure 304. Single use structure 304 is similar to single use structure 178 previously described except as otherwise mentioned herein. Elements that are the same as those in single use structure 178 have been designated using the same reference numbers in FIG. 26.

Single use structure 304 includes a continuous annular concentrate dam 306. Concentrate dam 306 extends downward in the separation chamber 224 and is disposed radially inward of the substantially annular concentrate opening 218. The exemplary annular concentrate dam shown in cross-section extends downward below the concentrate opening and in axial cross-section includes a tapered outward surface 308 that extends outwardly and toward opening 218.

Single use structure 304 further includes a continuous annular centrate dam 310. Centrate dam 310 extends downward in the separation chamber 224 below the substantially annular centrate opening 210. Centrate dam 310 is disposed radially outward from the centrate opening 210. In the exemplary arrangement the downward distance that the concentrate dam 306 and the centrate dam 310 extend in the separation chamber 224 is substantially the same. However in other exemplary arrangements other configurations may be used. Also in other example arrangements a centrifuge structure may include a concentrate dam or a centrate dam, but not both.

An annular recess 312 extends in the separation chamber radially between the centrate dam and the concentrate dam. The exemplary annular recess extends upward between the centrate and concentrate dams so as to form an annular pocket therebetween.

In exemplary arrangements the concentrate dam 306 helps to assure that primarily cellular material or other solid material to be separated can pass outwardly along the upper portion bounding the separation chamber 224 to reach the concentrate opening 218 and the concentrate centripetal pump chamber 214. The centrate dam 310 further helps to assure that primarily cell free centrate material is enabled to pass along the upper surface bounding the separation chamber 224 and into the substantially annular centrate opening 210 to reach the centrate pump chamber 206. It should be understood that numerous different configurations of concentrate and centrate dams may be utilized in different example arrangements depending on the nature of the material being processed and the requirements for handling such materials.

Figure 24:
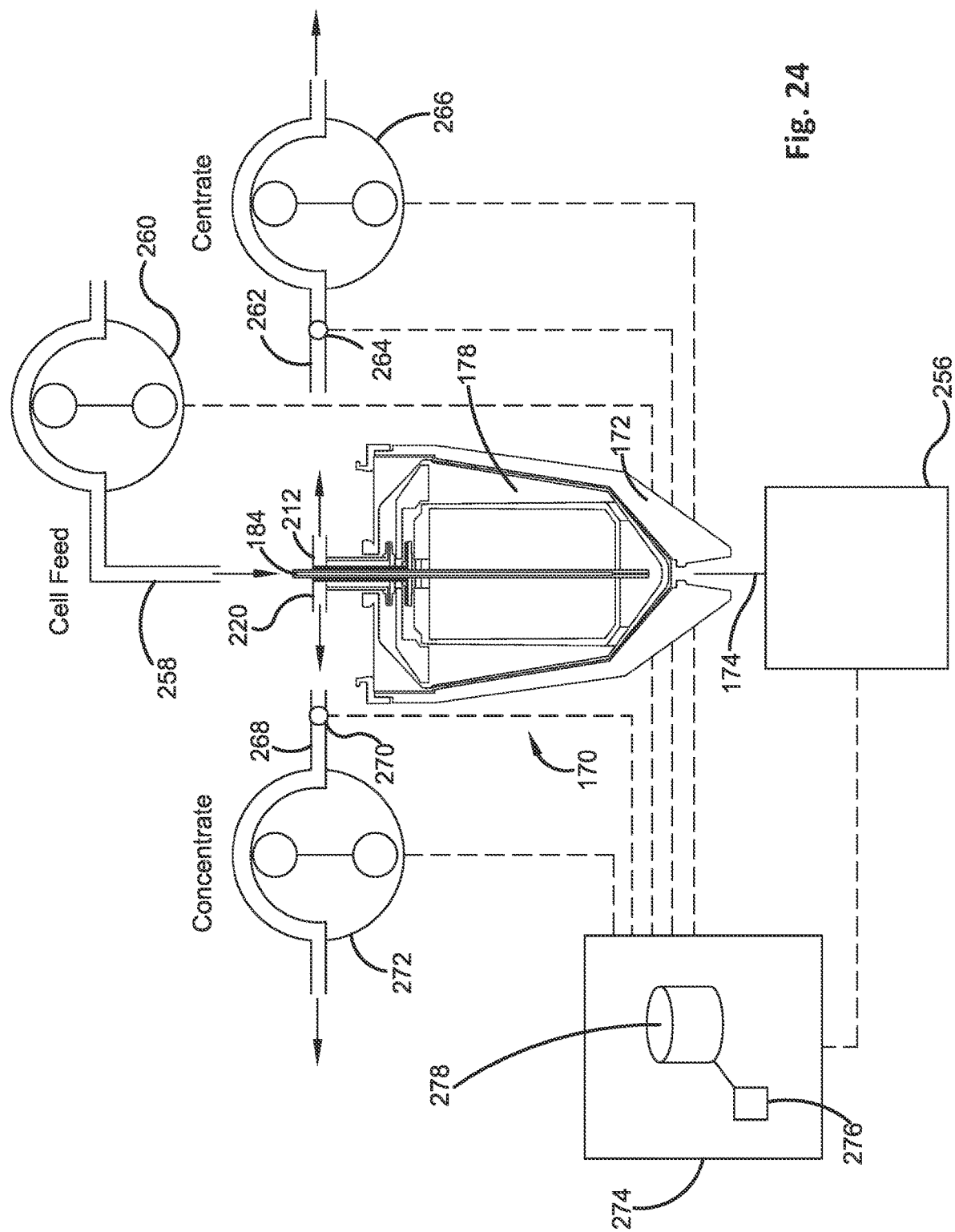
FIG. 24 is a schematic view of the control system for an exemplary continuous centrate and concentrate discharge centrifuge system.

FIG. 24 is a schematic view of an exemplary control system for providing generally continuous processing of a cell culture material to produce streams of generally cell free centrate and cell concentrate. In the exemplary arrangement the centrifuge system 170 previously discussed is shown. However it should be understood that the exemplary system features may be used with numerous different types of materials and centrifuge systems and structures such as those discussed herein.

In the exemplary arrangement shown, the centrifuge bowl 172 is rotated at a selected speed about axis 174 by a motor 256. The feed tube 184 is in operative connection with a cell culture feed line 258 through which the cell culture batch material is received. The feed line is in operative connection with a feed pump 260. In an exemplary arrangement feed pump 260 may be a peristaltic pump or other suitable pump for delivering cell culture into the single use structure at a selected flow rate.

The centrate discharge tube 212 is in fluid connection with a centrate discharge line 262. A centrate optical density sensor 264 is in operative connection with an interior area of the centrate discharge line 262. In the exemplary arrangement the centrate optical density sensor is an optical sensor that is operative to determine the density of cells currently in the centrate passing from the single use structure. This is accomplished in the exemplary arrangement by measuring the reduction in intensity of light output by an emitter that is received by a receiver disposed from the emitter and which has at least a portion of the centrate flow passing there-between. The amount of light from the emitter that is received by the receiver decreases with the increasing density of cells in the centrate. Of course this is only one example of a sensor that may be utilized for purposes of determining the density or amount of cells present in the centrate, and in other arrangements other types of sensors may be used. For example, the light may be near infrared or other visible or non-visible light. In other sensing arrangements other forms of electromagnetic, sonic or other types of signals may be used for sensing. The centrate discharge line is further in operative connection with a centrate pump 266. In the exemplary arrangement the centrate pump may comprise a peristaltic pump or other variable rate pump suitable for pumping the centrate material.

In the exemplary arrangement the concentrate discharge tube 220 is in operative connection with a concentrate discharge line 268. A concentrate optical density sensor 270 is in operative connection with at least a portion of the interior area of the concentrate discharge line 268. The exemplary concentrate optical density sensor may operate in a manner like the centrate optical density sensor previously discussed. Of course it should be understood that the concentrate optical density sensor may include different structures or properties, and that different types of cell density sensors may be used in other exemplary arrangements. The concentrate discharge line 268 is in operative connection with a concentrate pump 272. In the exemplary arrangement the concentrate pump 272 may include a peristaltic pump or other variable rate pump suitable for pumping the concentrate without causing damage thereto. Of course it should be understood that these structures and components are exemplary and alternative systems may include different or additional components.

The exemplary control system includes control circuitry 274 which is alternatively referred to herein as a controller. In exemplary arrangements the control circuitry may include one or more processors schematically indicated 276. The control circuitry may also include one or more data stores schematically indicated 278. The one or more data stores may include one or more types of tangible mediums which hold circuit executable instructions and data which when executed by the controller cause the controller to carry out operations such as those later discussed herein. Such mediums may include for example, solid-state memory, magnetic memory, optical memory or other suitable non-transitory medium for holding circuit executable instructions and/or data. The control circuitry may include structures like those previously discussed.

The operations carried out by the exemplary controller 274 will now be described in connection with the schematic representation of a logic flow shown in FIG. 25. In the exemplary arrangement the controller 274 is operative to control the operation of the components in the system so as to maintain the delivery of concurrent output flows of generally cell free centrate and cell concentrate. This is accomplished using the optical density sensors in the respective centrate and concentrate outlet lines to detect the cell density (or turbidity) of the output feeds and to adjust the operation of the system components so as to maintain the output within desired ranges.

In the use of the exemplary control system, the cell concentration of cells in the cell culture material to be processed is measured separately prior to initiating the operation of the system. The desired axial rotation speed of the centrifuge is determined as is a speed for operation of the feed pump 260. In the exemplary arrangement the rotational speed of the centrifuge and the feed rate of the cell material by the feed pump are generally maintained by the controller as constant set values. Of course in other arrangements and systems alternative approaches may be used in which the speeds and feed rates may be adjusted by the controller during cell processing.

In the exemplary arrangement, based on the determined cell concentration, the discharge rate (flow rate) of the external concentrate pump 272 is set at an initial value which is referred to herein as a "prime value." Also preset in the exemplary arrangement is a "prime duration" which corresponds to a time period during which the external concentrate pump 272 will operate initially at the prime value. This duration allows the single use structure 178 to partially fill. Also in the exemplary system a "base speed" is set for the concentrate pump based on the cell density as well as the feed rate from the feed pump 260. The base speed of the concentrate pump is a speed (which corresponds to flow rate) at which the concentrate pump will operate subsequent to the prime duration. In the exemplary arrangement the set base speed is generally expected to correspond to a concentrate pump speed which will produce centrate with the cell density below a desired set limit and cell concentrate with the cell density generally above a further desired set limit. The set values and limits are received by the controller in response to inputs through suitable input devices and stored in the at least one data store.

Figure 25:
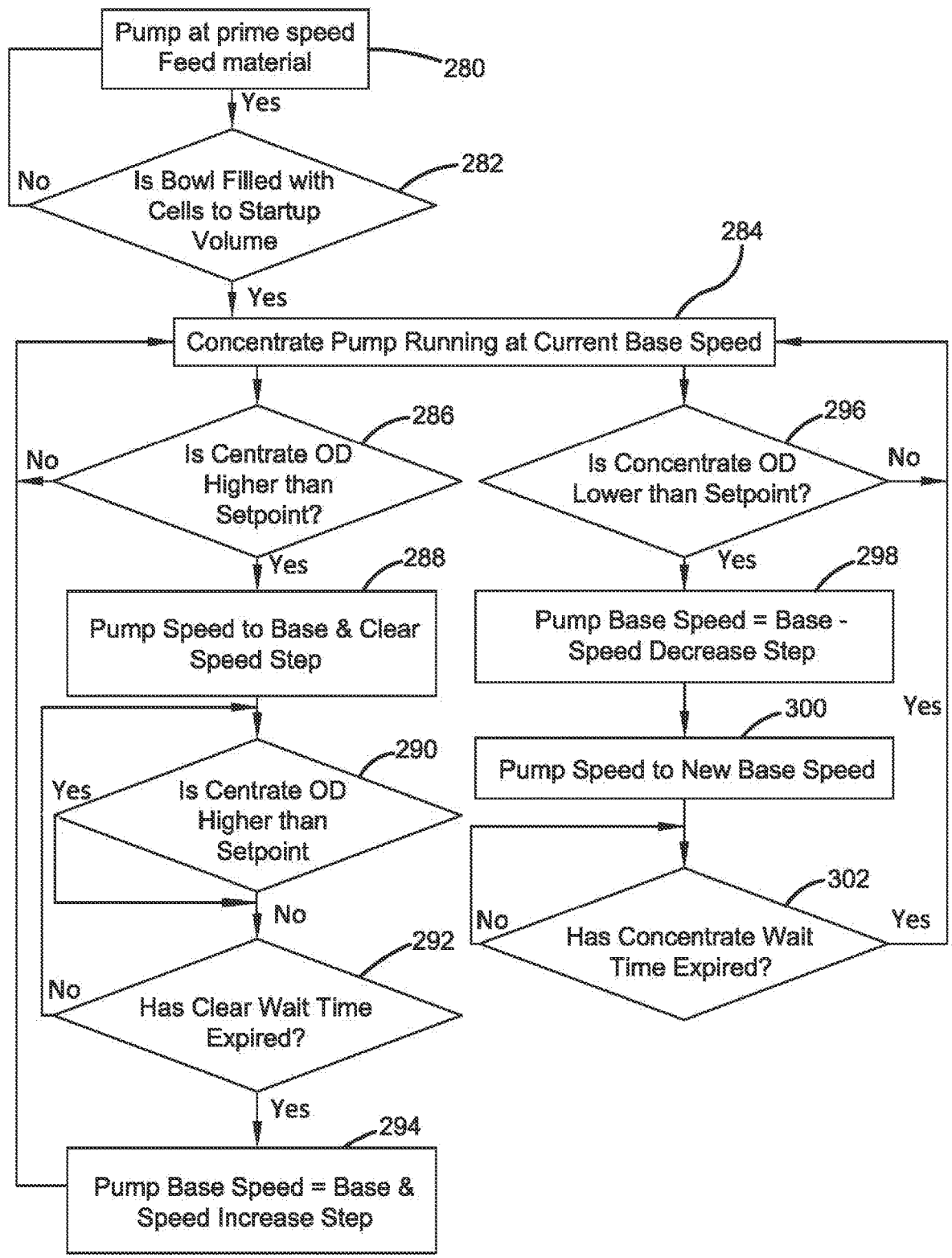
FIG. 25 is a schematic representation of logic flow associated with an exemplary control system of FIG. 24.

In the exemplary logic flow represented in FIG. 25, the operation of the concentrate pump 272 at the initial prime speed is represented by step 280. A determination is made at a step 282 by the controller as to whether the concentrate pump has operated at the prime speed for the time period corresponding to the prime duration which is operative to at least partially fill the single use structure 178.

Once the concentrate pump has operated at the prime speed for the prime duration, the controller causes the concentrate pump speed to then increase to the base speed as represented by a step 284. The controller 274 operates to monitor the cell density in the centrate as detected by sensor 264. The controller operates to determine if the optical density is higher than the desired set point as represented by step 286. If the optical density of the centrate is not higher than the set point, then the centrate is sufficiently clear of cells or cell material such that this measurement does not cause a change by the controller in the operating speed of the concentrate pump, and the logic returns to step 284.

If in step 286 the optical density of the centrate is determined to be higher than the set point, then the logic proceeds to a step 288. In step 288 the controller operates to increase the speed of the concentrate pump by a set incremental step amount. This speed step increase is intended to generally cause the optical density of the centrate to clear as a result of reducing the number of cells therein.

After the speed of the concentrate pump 272 is increased in step 288 the controller then operates responsive to the sensor 264 to determine in a step 290 if the optical density of the centrate is still above the set point a set time after the incremental increase in the speed (flow) of the concentrate pump. If it is, then the controller continues to monitor the optical density of the centrate until it is not higher than the set point. In the exemplary arrangement the instructions include a set time period during which the centrate optical density must not be higher than the set point before the concentrate pump speed controller determines that the adjustment to the base speed is sufficient to maintain the optical density of the centrate at a level that is at or below the desired set point. Step 292 is representative of the controller making a determination that the increased concentrate pump speed has maintained the optical density of the centrate at or below the set point for the stored set time period value which corresponds to consistently producing an outflow of sufficiently cell free centrate or reaching the programmed wait time. Responsive to producing the sufficiently cell free centrate for the desired duration or reaching the programmed wait time, the controller next operates in a step 294 to cause the base speed value of the concentrate pump to be adjusted to correspond to the increased base speed. The controller sets the new base speed and the logic returns to the step 284. It should be noted that if the centrate optical density is still above the set point as determined in step 286, the concentrate pump speed will again be adjusted.

The exemplary controller also concurrently monitors the optical density of the cells in the output concentrate flow. This is done by monitoring the optical density as detected by sensor 270. As represented by step 296 the controller operates to determine if the optical density in the concentrate is lower than a desired setpoint. If the concentrate optical density is detected at or above the desired set point value that is stored in the data store, then the concentration of cells in the concentrate output flow is at or above the desired level, and the logic returns to the step 284. However if the optical density of the concentrate is below the desired set point, meaning that the level of cells in the concentrate is less than desired, the controller moves to a step 298. In step 298 the speed of the concentrate pump is reduced by a predetermined incremental step amount. Reducing the speed of the concentrate pump will reduce output flow rate, generally increase the amount of cells in the concentrate output flow and therefore increase the optical density of the concentrate output flow.

The controller then operates the concentrate pump 272 at the new reduced speed as represented in a step 300. As represented in the step 302 the controller operates the concentrate pump at this reduced speed for a set time period corresponding to a set value stored in the data store so that the concentration of cells in the output concentrate flow may increase before a determination is made as to whether the speed decrease is sufficient. Once the time period is determined to have passed in the step 302, the controller returns to the step 284 from which the logic flow is then repeated to determine if further speed adjustments are needed.

Of course it should be understood that this schematic simplified logic flow is exemplary and in other arrangements a different logic flow and/or additional operating parameters of system components may be monitored and adjusted for purposes of achieving the desired output flow of centrate and concentrate. For example in other exemplary arrangements the speed of the centrate discharge pump, and thus the centrate discharge flow, may be varied by the controller responsive at least in part to the optical density as detected by the centrate optical density sensor which corresponds to the level of cells in the centrate. For example, the controller may operate to reduce the flow rate of the centrate pump if the level of cells in the centrate is detected as above a set limit. This may be done by the controller as an alternative to or in combination with controlling the concentrate discharge flow rate. The controller may vary the centrate flow as appropriate to assure that the level of cells in the centrate is maintained below set limits or within a set range.

Alternatively or in addition the controller may also control the flow rate of cell suspension entering the single use structure. This may be done in conjunction with varying the flow rates of centrate and concentrate from the single use structure, to maintain the level of cells in the centrate and concentrate within the programmed set limits that are stored in memory associated with the controller. Additionally the controller may also operate in accordance with its programming to vary other process parameters such as variation of bowl rotational speed, the introduction of dilutant and dilutant introduction rates as well as other process parameters to maintain the centrate and concentrate properties within programmed limits and desired process rates. Further in other exemplary arrangements other properties or parameters may be monitored and adjusted by the control system for purposes of achieving the desired products.

Figure 27:
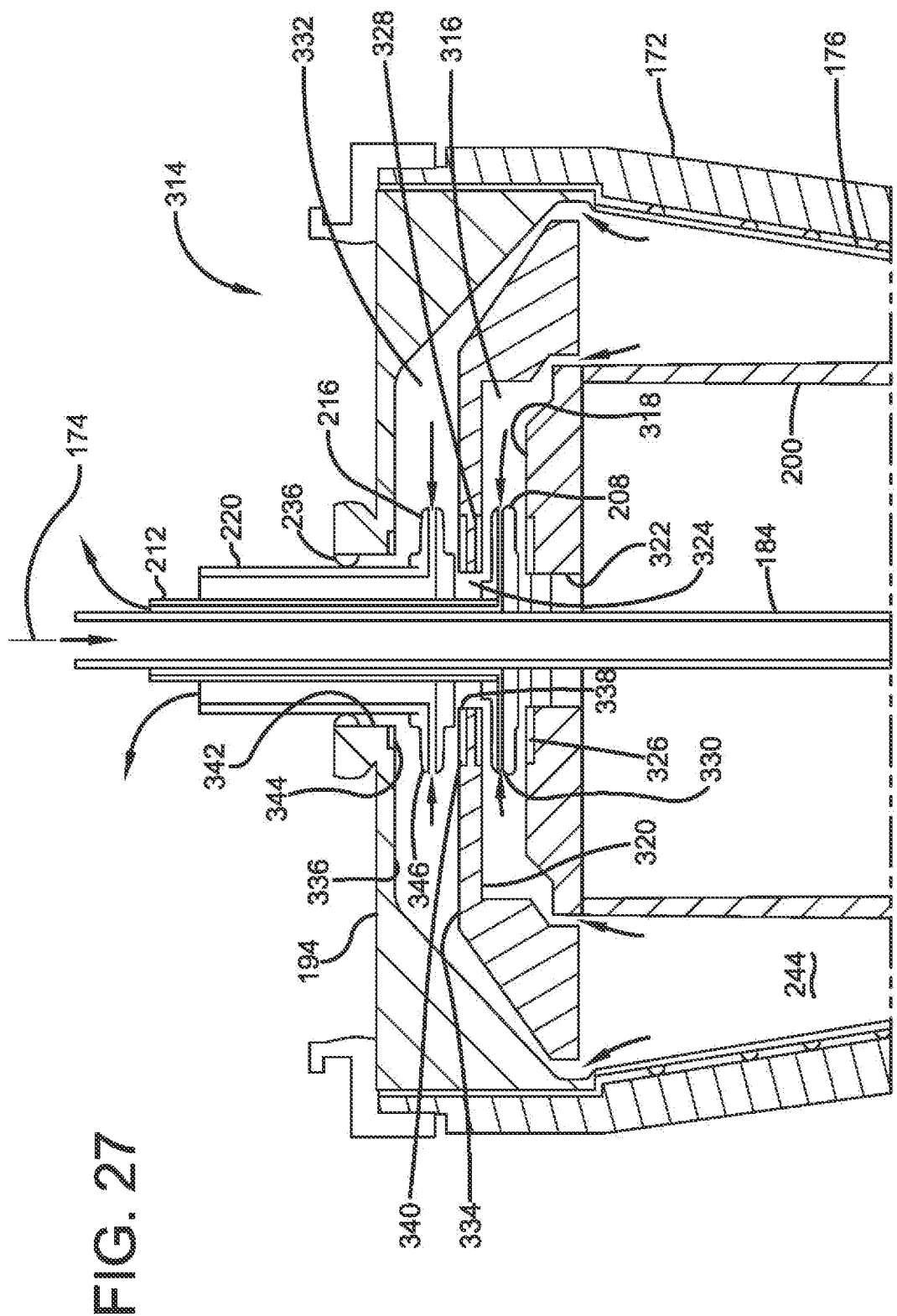
FIG. 27 is a cross-sectional view of an exemplary upper portion of a single use structure that includes vanes in the centrate pump chamber and the concentrate pump chamber for purposes of controlling the radial position of the air/liquid interface.

FIG. 27 shows a cross-sectional view of a further alternative single use centrifuge structure 314. Single use structure 314 is generally similar to single use structure 178 previously discussed except as specifically mentioned. Single use structure 314 includes elements that are operative to help assure that the air/liquid interface of the air pocket that extends in the single use structure and that isolates the seal 236 from the material that is being processed is more stably maintained at a desired radial location.

In the single use structure 314 the centrate pump 208 is positioned in a centrate pump chamber 316. Centrate pump chamber 316 is bounded vertically at the bottom by a circular lower centrate centripetal pump chamber surface 318. Centrate pump chamber 316 is bounded vertically at the upper side by a circular upper centrate centripetal pump chamber surface 320.

Lower centrate pump chamber surface 318 extends radially outward from a lower centrate centripetal pump chamber opening 322. In the exemplary arrangement the lower centrate centripetal pump chamber opening 322 extends through a circular top of the core 200 and corresponds to upper opening 202 previously discussed. The feed tube 184 extends through the lower centrate centripetal pump chamber opening.

Upper centrate centripetal pump chamber surface 320 extends radially outward from a circular upper centrate centripetal pump chamber opening 324. The feed tube 184 and the centrate discharge tube 212 extend axially through the upper centrate centripetal pump chamber opening.

A plurality of angularly spaced upward extending lower centrate chamber vanes 326 extend on the lower centrate centripetal pump chamber surface 318. Each of the lower centrate chamber vanes 326 extend radially outward beginning from the lower centrate centripetal pump chamber opening 322. The lower centrate chamber vanes 326 which are shown in greater detail in FIG. 28 extend radially outward from the axis of rotation 174 a lower centrate vane distance V. In the exemplary arrangement the lower centrate chamber vanes 326 extend upward in a circular recess on the lower centrate centripetal pump chamber surface 318. However it should be understood that this arrangement is exemplary and in other arrangements other configurations may be used; for example the radial length of the vanes, vane height, and the depth and diameter of the recess may be varied to achieve desired fluid pressure properties.

A plurality of angularly spaced downward extending upper centrate chamber vanes 328 extend from upper centrate centripetal pump chamber surface 320. Each of the upper centrate chamber vanes 328 extend radially outward beginning from the upper centrate centripetal pump chamber opening 324. The upper centrate chamber vanes extend radially outward from the axis of rotation 174 an upper centrate vane distance. In the exemplary arrangement the upper centrate vane distance substantially corresponds to the lower centrate vane distance V. In the exemplary arrangement the upper centrate chamber vanes extend downward in a circular recess on the upper centrate centripetal pump chamber surface that has a configuration like that shown for the lower centrate chamber vanes in FIG. 28, but in an inverted orientation.

In the exemplary arrangement shown the centrate centripetal pump 208 includes a substantially annular centrate centripetal pump opening 330. The substantially annular centrate centripetal pump opening 330 is disposed radially outward from the axis of rotation 174, a centrate pump opening distance. The centrate pump opening distance at which the centrate centripetal pump opening 330 is positioned, is a greater radial distance than the lower centrate vane distance and the upper centrate vane distance for reasons that are later discussed.

In the exemplary arrangement of the single use structure 314 the concentrate centripetal pump 216 is positioned in a concentrate pump chamber 332. Concentrate pump chamber 332 is bounded vertically at a lower side by a circular lower concentrate centripetal pump chamber surface 334. Concentrate pump chamber 332 is bounded vertically at an upper side by a circular upper concentrate centripetal pump chamber surface 336.

The lower concentrate centripetal pump chamber surface 334 extends radially outward from a lower concentrate centripetal pump chamber opening 338. In the exemplary arrangement the lower concentrate centripetal pump chamber opening corresponds in size to and is continuous with the upper centrate centripetal pump chamber opening 324. The feed tube 184 and the centrate discharge tube 212 extend through the lower concentrate centripetal pump chamber opening 338.

A plurality of angularly spaced upward extending lower concentrate chamber vanes 340 extend on lower concentrate centripetal pump chamber surface 334. The lower concentrate chamber vanes 334 extend radially outward beginning from the lower concentrate centripetal pump chamber opening 338. The lower concentrate chamber vanes 334 extend radially outward from the axis of rotation a lower concentrate vane distance. In the exemplary arrangement the lower concentrate chamber vanes 334 extend on a circular recess portion of the lower concentrate centripetal pump chamber surface similar to the upper and lower centrate chamber vanes previously discussed. Of course it should be understood that this configuration is exemplary.

Upper concentrate centripetal pump chamber surface 336 extends radially outward from an upper concentrate centripetal pump chamber opening 342. The feed tube 184, the centrate discharge tube 212 and the concentrate discharge tube 220 coaxially extend through the upper concentrate centripetal pump chamber opening 342. A plurality of angularly spaced upper concentrate chamber vanes 344 extend downward from surface 336. The upper concentrate chamber vanes extend radially outward from the upper concentrate centripetal pump chamber opening 342 an upper concentrate vane distance. The upper concentrate chamber vanes extend in an upward extending circular recess in the upper concentrate centripetal pump chamber surface. In the exemplary arrangement the upper concentrate chamber vanes are configured in a manner similar to the lower concentrate chamber vanes and the upper and lower centrate chamber vanes previously discussed. Of course it should be understood that this approach is exemplary and in other arrangements other approaches may be used.

Concentrate centripetal pump 216 includes a substantially annular concentrate pump opening 346. Concentrate pump opening is radially disposed from the axis of rotation 174 a concentrate pump opening distance. In the exemplary arrangement the upper and lower concentrate vane distances are less than the concentrate pump opening distance. Of course it should be understood that this configuration is exemplary and in other arrangements other approaches may be used.

Figure 28:
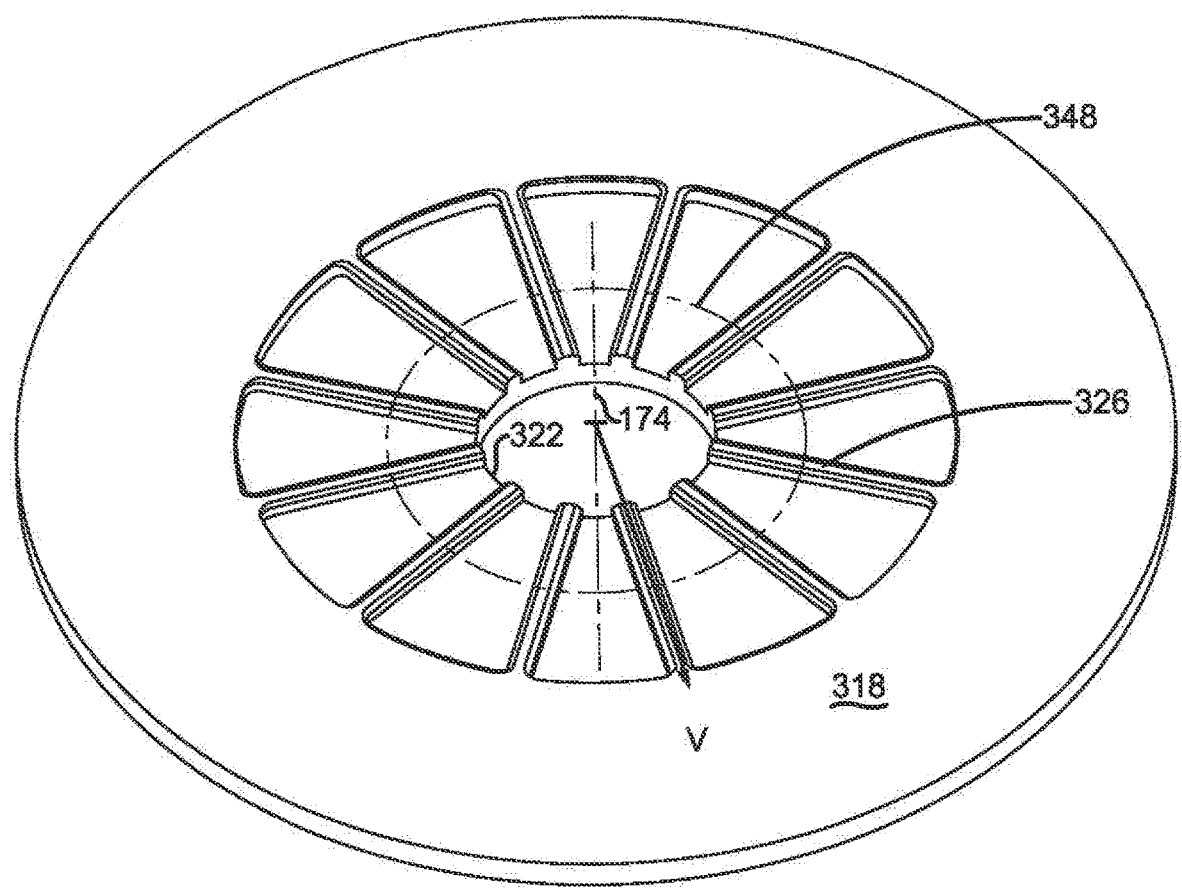
FIG. 28 is a perspective view of a chamber surface of an exemplary concentrate or centrate pump chamber and that includes a plurality of chamber vanes.
Figure 29:
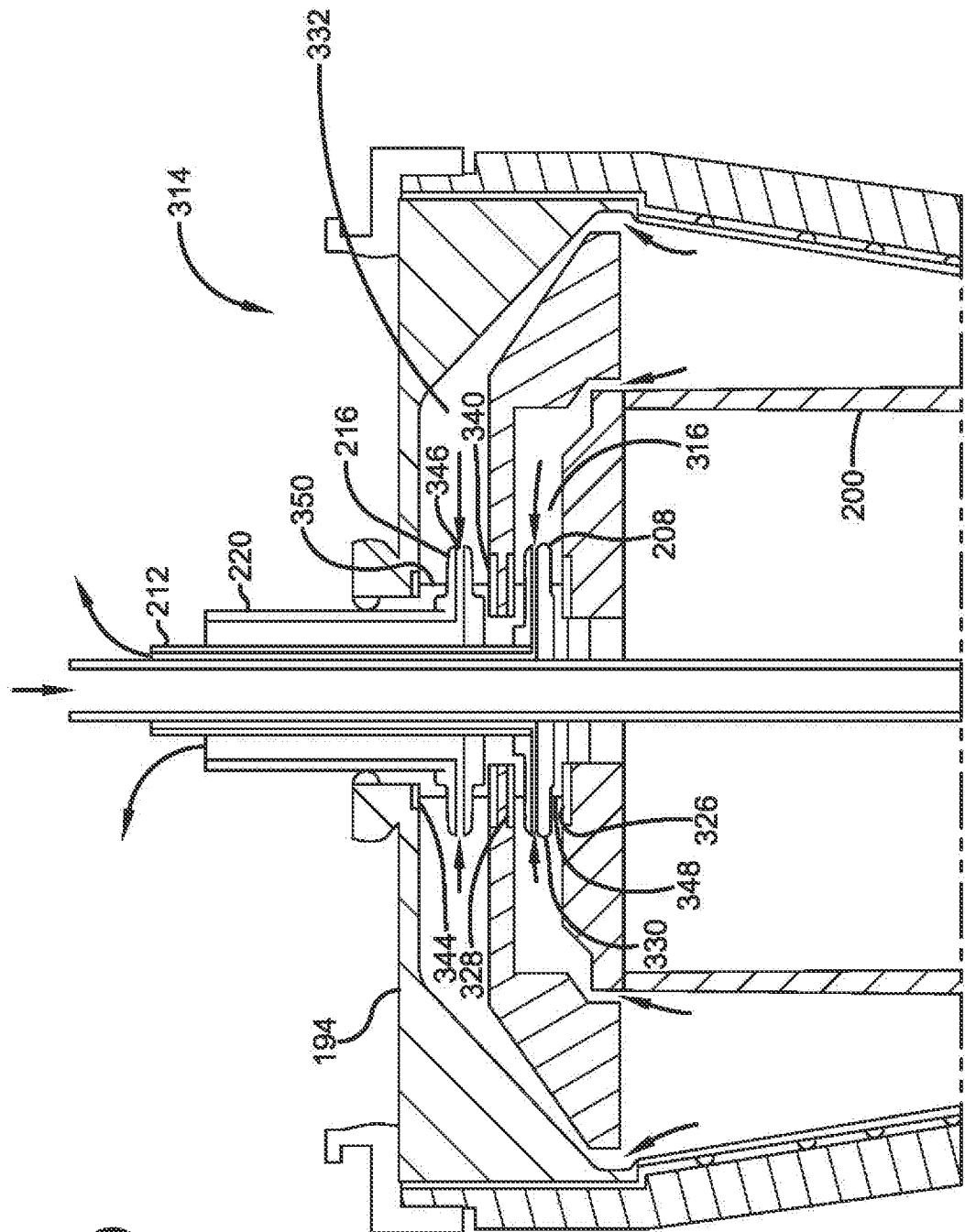
FIG. 29 is a cross-sectional view of an exemplary upper portion of a single use structure similar to that shown in FIG. 27 showing a position of an air/liquid interface.

In the exemplary single use structure 314 the upper and lower concentrate chamber vanes 344, 340, and the upper and lower centrate chamber vanes 326, 328 operate to stabilize and radially position the annular air/liquid interface 348 in the centrate pump chamber 330 and the air/liquid interface 350 in the concentrate pump chamber 332. As represented in FIG. 28 the air/liquid interface 348 is positioned radially intermediate along the radial length of the centrate chamber vanes. This is radially inward from the centrate pump opening 330. The radially extending centrate chamber vanes operate to provide centrifugal pumping force which maintains the annular air/liquid interface 348 at a radial location, both above and below the centrate centripetal pump, that is disposed radially inward of the centrate pump opening 330. In exemplary arrangements the vanes further help to stabilize the air/liquid interface so that it maintains a coaxial circular configuration both above and below the centrate pump. Further in exemplary arrangements the radial position of the interface relative to the axis of rotation can be controlled as later discussed so that the centrate pump opening 330 is consistently maintained in the liquid centrate and is not exposed to air.

The upper concentrate chamber vanes 344 and the lower concentrate chamber vanes 340 work in a similar manner to the centrate chamber vanes. The concentrate chamber vanes maintain the circular air/liquid interface 350 in the concentrate pump chamber 332 at a radial distance that is inward of the substantially annular concentrate pump opening 346. This configuration assures that the concentrate pump opening is consistently exposed to the concentrate and not to air. It should further be understood that although in the arrangement shown the centrate centripetal pump and the concentrate centripetal pump are of substantially the same size, in other arrangements the centripetal pumps may have different sizes. In such situations the radial distance from the axis of rotation that the centrate chamber vanes and the concentrate chamber vanes extend may be different. Also the radial position relative to the axis of rotation of the air/liquid interface in the centrate pump chamber and the concentrate pump chamber may be different. Numerous different vane configurations and arrangements may be utilized depending on the particular relationships between the components which make up the single use device and the particular material that is processed via the single use structure.

Figure 30:
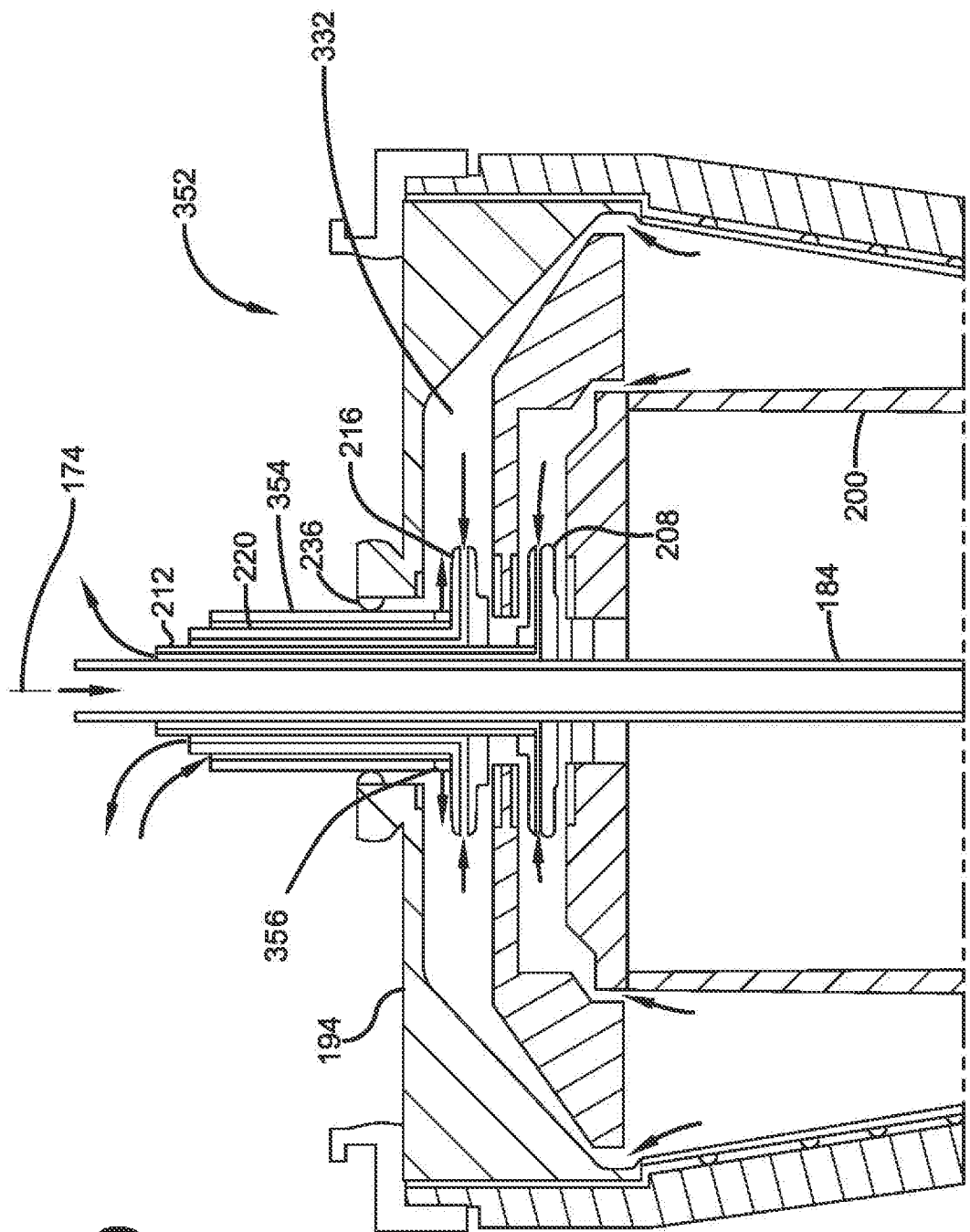
FIG. 30 is a cross-sectional view of an exemplary upper portion of a single use structure including an air passage for maintaining pressurized air in the air pocket.

FIG. 30 shows an upper portion of a further alternative single use structure 352. The single use structure 352 is similar to single use structure 304 except as otherwise discussed. Single use structure 352 includes an air tube 354 that extends in coaxial surrounding relation of the concentrate discharge tube 220. The air tube 354 is in communication with openings 356 inside the single use structure. Openings 356 extend from the interior of the air tube to above the concentrate centripetal pump 216 in the concentrate pump chamber 332. In this exemplary arrangement the seal 236 as schematically shown, operatively engages the air tube 354 to maintain the air tight engagement with the air tube as well as the concentrate discharge tube, centrate discharge tube and the feed tube. As can be appreciated the air tube may be utilized to selectively maintain the level of the air pressure in the air pocket within the single use structure. Such an arrangement may be utilized in connection with systems like those previously discussed or in other systems, in which an external supply of pressurized air is utilized to isolate the seal of the centrifuge structure from the material being processed and to maintain the air/liquid interface at a desirable location. Of course it should be understood that this structure is exemplary and other arrangements other approaches may be used.

FIG. 31 schematically shows a system 358 that may be used for continuously separating cell suspension into substantially cell free centrate and concentrate. System 358 is similar to system 170 previously discussed, except as otherwise mentioned herein. In the exemplary arrangement system 358 operates using a single use structure similar to single use structure 352. The controller 274 of system 358 operates to control the position of the air/liquid interface within the single use structure to assure that the interface is maintained radially inward relative to the axis of rotation from each of the centrate pump opening and the concentrate pump opening.

In the exemplary arrangement a flow back pressure regulator 360 is in fluid connection with the centrate discharge line 262. In the exemplary arrangement the flow back pressure regulator 360 is fluidly intermediate of the centrate discharge tube 212 and the centrate pump 266. The exemplary system 358 includes a source of pressurized air schematically indicated 362. The source of pressurized air 362 is connected to a pilot pressure control valve 364. The control valve is in operative connection with the controller 274. Signals from the controller 274 cause selectively variable pressure in a pilot line 366. The pilot line 366 is in fluid connection with the back pressure regulator 360. The pressure applied by the pilot pressure control valve 264 in the pilot line 366 is operative to control the centrate flow and consequently the centrate flow back pressure that is applied by the flow back pressure regulator 360.

In the exemplary arrangement a pressure control valve 368 is in fluid communication with the source of pressurized air 362. Control valve 368 is also in operative connection with the controller 274. In this exemplary arrangement the control valve 368 is controlled to selectively apply precise pressure to the air tube 354 and the air pocket within the upper portion of the single use structure 352.

In the exemplary arrangement the controller 274 operates in accordance with stored executable instructions to control the operation of the system 358 in a manner like that previously discussed in connection with system 170. Further in the exemplary arrangement the controller 274 operates to control the pilot pressure valve 364 to vary the back pressure that is applied to the centrate discharge tube 212 by the back pressure regulator 360. The controller 274 also operates to control valve 368. The controller operates to maintain and selectively vary the pressure applied in the air pocket at the top of the interior of the single use structure. The controller operates in accordance with its programming to vary the back pressure of the centrate flow and/or the air pocket pressure to maintain the air/liquid interface of the air pocket at a radial distance from the axis of rotation that is inward from the centrate pump opening 330 and the concentrate pump opening 346. This pressure variation in both the centrate flow back pressure and air pocket pressure, in combination with the action of the centrate chamber vanes and concentrate chamber vanes in the exemplary arrangement, maintain the stability and radially outward extent of the air/liquid interface so as to assure that introduction of air is minimized in the centrate and concentrate outputs from the single use structure. Further the ability to selectively vary the back pressure and flow of the centrate can impact the level of cells and corresponding detected optical density of the discharged concentrate. Thus the controller may operate in accordance with its programming to selectively vary both the concentrate flow rate, centrate back pressure and flow rate, internal air pocket pressure, the feed rate of cell suspension into the single use structure and perhaps other operating variables of the centrifugation process, to maintain the centrate and concentrate properties within the set limits and/or ranges stored in the at least one data store associated with the controller. Further the exemplary arrangement may enable separation of different types of materials and operations at different flow rates while maintaining reliable control of the separation process. Of course while it should be understood that the control of the position of the air/liquid interface is described in connection with features of system 170, such control may also be utilized in systems of other types which include other or different types of processing elements.

Thus the new centrifuge system and method of the exemplary arrangements achieve at least some of the above stated objectives, eliminates difficulties encountered in the use of prior devices and systems, solves problems and attains the desirable results described herein.

In the foregoing description certain terms have been used for brevity, clarity and understanding, however, no unnecessary limitations are to be implied there from because such terms are for descriptive purposes and are intended to be broadly construed. Moreover, the descriptions and illustrations herein are by way of examples and the invention is not limited to the exact details shown and described.

It should be understood that the features and/or relationships associated with one arrangement can be combined with features and/or relationships from another arrangement. That is, various features and/or relationships from various arrangements can be combined in further arrangements. The inventive scope of the disclosure is not limited to only the arrangements shown or described herein.

In the following claims any feature described as a means for performing a function shall be construed as encompassing any means known to those skilled in the filed as capable of performing the recited function, and shall not be limited to the structures shown herein or mere equivalents thereof.

Having described the features, discoveries and principles of the new and useful features, the manner in which they are constructed, utilized and operated, and the advantages and useful results attained, the new and useful structures, devices, elements, arrangements, parts, combinations, systems, equipment, operations and relationships are set forth in the appended claims.

We claim:
1. Apparatus comprising:
a multi-use rotatable centrifuge bowl, wherein the bowl is rotatable about a vertically extending axis and includes an axially centered cavity that is radially bounded by a bowl cavity wall,
a single use structure, wherein the single use structure is configured to be removably positioned in the axially centered cavity in engaged relation with the bowl,
wherein the single use structure bounds an interior area in which cells in a cell culture are separated through centrifugal force as a result of rotation of the single use structure, into cell centrate and cell concentrate,
wherein in an operative position the single use structure includes
an upper disc shape portion,
an annular outer wall, wherein the annular outer wall
externally is at least partially in radially abutting relation with the bowl cavity wall,
is in operative fluid tight relation with the upper disc shape portion adjacent to an upper end of the annular outer wall,
internally bounds a separation chamber in which the cell centrate and the cell concentrate are separated, wherein at least a portion of the separation chamber has a vertically truncated cone shape with a smaller inside radius adjacent to a lower end of the annular outer wall that is axially lower than the upper end, at least one vertically extending axially centered fluid tight tube, wherein the at least one axially centered fluid tight tube extends through the upper disc shape portion, is in fluid connection with the separation chamber, is operative to at least one of deliver cell culture into the interior area of the single use structure, deliver cell concentrate out of the interior area of the single use structure, and deliver cell centrate out of the interior area of the single use structure.

2. The apparatus according to claim 1 wherein the single use structure includes an axially centered cylindrical structure in the separation chamber, wherein the axially centered cylindrical structure includes at least one radially outer surface that is radially inwardly disposed away from the annular outer wall.

3. The apparatus according to claim 1 wherein the at least one axially centered fluid tight tube is operative to receive cell concentrate from a vertically uppermost and radially outermost area of the separation chamber, and deliver the received cell concentrate out of the interior area.

4. The apparatus according to claim 1 wherein the single use structure includes an axially centered cylindrical structure in the separation chamber, wherein the axially centered cylindrical structure includes at least one radially outer surface that is radially inwardly disposed away from the annular outer wall, wherein the at least one axially centered fluid tight tube is operative to receive cell concentrate from a vertically uppermost and radially outermost area of the separation chamber that is radially disposed outwardly away from the axially centered cylindrical structure, and deliver the received cell concentrate out of the interior area.

5. The apparatus according to claim 1 wherein the at least one axially centered fluid tight tube is operative to receive cell concentrate from a radially inward and vertically upward extending passage, wherein the passage extends fluidly intermediate of a vertically uppermost and radially outermost area of the separation chamber and the at least one axially centered fluid tight tube, and deliver cell concentrate out of the interior area.

6. The apparatus according to claim 1 wherein the at least one axially centered fluid tight tube is operative to receive cell concentrate from a radially inward and vertically upward extending passage, wherein the passage extends fluidly intermediate of a vertically uppermost and radially outermost area of the separation chamber and the at least one axially centered fluid tight tube, and deliver cell concentrate out of the interior area, wherein the interior area includes a centrate chamber, wherein the centrate chamber extends below the upward extending passage, wherein the centrate chamber is operative to receive cell centrate.

7. The apparatus according to claim 1 wherein the at least one portion of the separation chamber having the vertically truncated cone shape is immediately vertically adjacent to the upper disc shape portion.

8. The apparatus according to claim 1 wherein the single use structure includes an axially centered cylindrical structure in the separation chamber, wherein the axially centered cylindrical structure includes at least one radially outer surface that is radially inwardly disposed from the annular outer wall, and at least one radially inward surface that is disposed radially away from the vertically extending axis.

9. The apparatus according to claim 1 wherein the single use structure further includes an axially centered cylindrical structure in the separation chamber, wherein the axially centered cylindrical structure includes at least one radially outer surface that is radially inwardly disposed from the annular outer wall, at least one radially extending fluid passage, wherein the at least one radially extending fluid passage is positioned below the axially centered cylindrical structure.

10. The apparatus according to claim 1 wherein the single use structure further includes a cylindrical core, wherein the portion of the separation chamber that has the vertically truncated cone shape extends radially between an outer surface of the cylindrical core and the annular outer wall.

11. The apparatus according to claim 1 wherein the at least one axially centered fluid tight tube includes a feed tube that is operative to deliver cell culture into the interior area, and an outlet tube concentric with the feed tube that is operative to deliver one of cell centrate and cell concentrate from the interior area.

12. The apparatus according to claim 1 wherein the at least one axially centered fluid tight tube includes a feed tube that is operative to deliver cell culture into the interior area, a first outlet tube that is concentric with the feed tube, that is operative to deliver cell centrate from the interior area, and a second outlet tube that is concentric with the feed tube, that is operative to deliver cell concentrate from the interior area.

13. The apparatus according to claim 1 wherein the single use structure further includes a cylindrical core in the interior area vertically intermediate of the upper disc shape portion and the lower end, wherein the portion of the separation chamber that has the vertically truncated cone shape extends radially between an outer surface of the cylindrical core and the annular outer wall and vertically immediately adjacent to the upper disc shape portion.

14. The apparatus according to claim 1 wherein the single use structure further includes a cylindrical core in the interior area vertically intermediate of the upper disc shape portion and the lower end, wherein the portion of the separation chamber that has the vertically truncated cone shape extends radially between an outer surface of the cylindrical core and the annular outer wall, and vertically immediately adjacent to the upper disc shape portion, wherein the at least one axially centered fluid tight tube includes a feed tube, wherein the feed tube is operative to deliver cell culture to the interior area in the lower end, and a centrate outlet tube, wherein the centrate outlet tube is concentric with the feed tube, and is operative to deliver cell centrate that has passed through a cell centrate opening in the upper disc shape portion, wherein the cell centrate opening is open to the separation chamber radially outward from the cylindrical core.

15. The apparatus according to claim 1 wherein the single use structure further includes a cylindrical core in the interior area vertically intermediate of the upper disc shape portion and the lower end, wherein the portion of the separation chamber that has the vertically truncated cone shape extends radially between an outer surface of the cylindrical core and the annular outer wall, and vertically immediately adjacent to the upper disc shape portion, wherein the at least one axially centered fluid tight tube includes a feed tube, wherein the feed tube is operative to deliver cell culture to the interior area in the lower end, and a concentrate outlet tube, wherein the concentrate outlet tube is concentric with the feed tube, and is operative to deliver cell concentrate that has passed through a cell concentrate opening in the upper disc shape portion, wherein the cell concentrate opening is open to the separation chamber radially outward from the cylindrical core and at a vertically uppermost and radially outermost area of the portion of the separation chamber that has the vertically truncated cone shape.

16. The apparatus according to claim 1 wherein the single use structure further includes a cylindrical core in the interior area vertically intermediate of the upper disc shape portion and the lower end, wherein the portion of the separation chamber that has the vertically truncated cone shape extends radially between an outer surface of the cylindrical core and the annular outer wall, and vertically immediately adjacent to the upper disc shape portion, wherein the at least one axially centered fluid tight tube includes a feed tube, wherein the feed tube is operative to deliver cell culture to the interior area in the lower end, a centrate outlet tube, wherein the centrate outlet tube is concentric with the feed tube, and is operative to deliver cell centrate that has passed through a cell centrate opening in the upper disc shape portion, wherein the cell centrate opening is open to the separation chamber radially outward from the cylindrical core, a concentrate outlet tube, wherein the concentrate outlet tube, is concentric with the feed tube, is operative to deliver cell concentrate that has passed through a cell concentrate opening in the upper disc shape portion, wherein the cell concentrate opening is open to the separation chamber radially outward from the cylindrical core and the cell centrate opening, and at a vertically uppermost and radially outermost area of the portion of the separation chamber that has the vertically truncated cone shape.

17. The apparatus according to claim 1 wherein the single use structure further includes a cylindrical core within the interior area vertically intermediate of the upper disc shape portion and the lower end, wherein the portion of the separation chamber that has the vertically truncated cone shape extends radially between an outer surface of the cylindrical core and the annular outer wall, and vertically immediately adjacent to the upper disc shape portion, wherein the upper disc shape portion includes an axially centered centrate chamber therein, wherein the at least one axially centered fluid tight tube includes a feed tube, wherein the feed tube extends through the centrate chamber and is operative to deliver cell culture to the interior area in the lower end, and a centrate outlet tube, wherein the centrate outlet tube is concentric with the feed tube, and is operative to deliver cell centrate that has passed through a cell centrate opening in the upper disc shape portion and the cell centrate chamber, wherein the cell centrate opening is open to the separation chamber radially outward from the cylindrical core.

18. The apparatus according to claim 1 wherein the single use structure further includes a cylindrical core in the interior area vertically intermediate of the upper disc shape portion and the lower end, wherein the portion of the separation chamber that has the vertically truncated cone shape extends radially between an outer surface of the cylindrical core and the annular outer wall, and vertically immediately adjacent to the upper disc shape portion, wherein the upper disc shape portion includes an axially centered concentrate chamber, wherein the at least one axially centered fluid tight tube includes a feed tube, wherein the feed tube extends through the concentrate chamber and is operative to deliver cell culture to the interior area in the lower end, and a concentrate outlet tube, wherein the concentrate outlet tube is concentric with the feed tube, and is operative to deliver cell concentrate that has passed through a cell concentrate opening in the upper disc shape portion and the concentrate chamber, wherein the cell concentrate opening is open to the separation chamber radially outward from the cylindrical core and at a vertically uppermost and radially outermost area of the portion of the separation chamber that has the vertically truncated cone shape.

19. The apparatus according to claim 1
wherein the single use structure further includes
   a cylindrical core in the interior area vertically intermediate of the upper disc shape portion and the lower end,
wherein the portion of the separation chamber that has the vertically truncated cone shape extends radially between an outer surface of the cylindrical core and the annular outer wall, and vertically immediately adjacent to the upper disc shape portion,
wherein the upper disc shape portion includes
   an axially centered concentrate chamber, and
   an axially centered centrate chamber,
      wherein the axially centered centrate chamber extends vertically below the axially centered concentrate chamber,
wherein the at least one axially centered fluid tight tube includes
   a feed tube, wherein the feed tube extends through each of the axially centered concentrate chamber and the axially centered centrate chamber, and is operative to deliver cell culture to the interior area in the lower end,
   a centrate outlet tube, wherein the centrate outlet tube
      is concentric with the feed tube,
      extends through the axially centered concentrate chamber, and
      is operative to deliver cell centrate that has passed through a cell centrate opening in the upper disc shape portion and the axially centered cell centrate chamber, wherein the cell centrate opening is open to the separation chamber radially outward from the cylindrical core,
   a concentrate outlet tube, wherein the concentrate outlet tube,
      is concentric with the feed tube,
      is operative to deliver cell concentrate that has passed through the axially centered cell concentrate chamber and a cell concentrate opening in the upper disc shape portion, wherein the cell concentrate opening is open to the separation chamber radially outward from the cylindrical core and the cell centrate opening, and
      at a vertically uppermost and radially outermost area of the portion of the separation chamber that has the vertically truncated cone shape.

20. The apparatus according to claim 1
wherein the single use structure further includes
   a cylindrical core in the interior area vertically intermediate of the upper disc shape portion and the lower end,
wherein the portion of the separation chamber that has the vertically truncated cone shape extends radially between an outer surface of the cylindrical core and the annular outer wall, and vertically immediately adjacent to the upper disc shape portion,
wherein the upper disc shape portion includes
   an axially centered concentrate chamber,
   a concentrate centripetal pump in the axially centered concentrate chamber,
   an axially centered centrate chamber,
   a centrate centripetal pump in the axially centered centrate chamber,
      wherein the axially centered centrate chamber extends vertically below the axially centered concentrate chamber,
wherein the at least one axially centered fluid tight tube includes
   a feed tube, wherein the feed tube extends through each of the axially centered concentrate chamber and the axially centered centrate chamber, and is operative to deliver cell culture to the interior area in the lower end,
   a centrate outlet tube, wherein the centrate outlet tube
      is concentric with the feed tube,
      extends through the axially centered concentrate chamber,
      is operative to receive cell centrate through the centrate centripetal pump, and
      is operative to deliver cell centrate that has passed through a cell centrate opening in the upper disc shape portion, the axially centered cell centrate chamber, and the centrate centripetal pump, wherein the cell centrate opening is open to the separation chamber radially outward from the outer surface of the cylindrical core,
   a concentrate outlet tube, wherein the concentrate outlet tube,
      is concentric with the feed tube,
      is operative to receive cell concentrate through the concentrate centripetal pump,
      is operative to deliver cell concentrate that has passed through a cell concentrate opening in the upper disc shape portion, the axially centered cell concentrate chamber and the concentrate centripetal pump, wherein the cell concentrate opening is open to the separation chamber
         radially outward from the cylindrical core and the cell centrate opening, and
         at a vertically uppermost and radially outermost area of the portion of the separation chamber that has the vertically truncated cone shape.

21. Apparatus comprising:
a multi-use rotatable centrifuge bowl,
   wherein the bowl is rotatable about a vertically extending axis, and
   includes an axially centered cavity,
a single use structure, wherein the single use structure
   is removably positionable in the axially centered cavity, and
   when positioned in the axially centered cavity is rotatable in operative engagement with the centrifuge bowl,
wherein in an operative position the single use structure includes
   an upper disc shape portion,
   a continuous annular outer wall,
      wherein the upper disc shape portion and the continuous annular outer wall bound an interior area of the single use structure,
   wherein the continuous annular outer wall
      is in operative fluid tight connection with the upper disc shape portion adjacent to an upper end of the continuous annular outer wall,
      internally bounds a separation chamber within the interior area, wherein in the separation chamber cell culture is separated into cell centrate and cell concentrate responsive to rotation of the single use structure in operative engagement with the centrifuge bowl,
      wherein at least a portion of separation chamber has a vertically truncated cone shape with a smaller inside radius adjacent to a lower end of the separation chamber that is lower than the upper end,
at least one vertically extending axially centered fluid tight tube, wherein the at least one axially centered fluid tight tube
extends through the upper disc shape portion, and
is operative to at least one of
deliver cell culture into the interior area of the single use structure,
deliver cell centrate out of the interior area of the single use structure, and
deliver cell concentrate out of the interior area of the single use structure.

22. The apparatus according to claim 21
wherein the single use structure further includes
an axially centered cylindrical structure, wherein the axially centered cylindrical structure
extends in the separation chamber, and
is bounded radially outward by at least one radially outer surface,
wherein each radially outer surface of the axially centered cylindrical structure is disposed radially inwardly in the separation chamber from the continuous annular outer wall.

23. The apparatus according to claim 21
wherein the at least one axially centered fluid tight tube is operative to deliver cell concentrate from the interior area,
wherein the at least one axially centered fluid tight tube is operative to receive cell concentrate from a vertically uppermost and radially outermost area of the separation chamber.

24. The apparatus according to claim 21
wherein the at least one axially centered fluid tight tube is operative to deliver cell concentrate out of the interior area,
wherein the at least one axially centered fluid tight tube is operative to receive cell concentrate from a radially inward and vertically upward extending passage,
wherein the radially inward and vertically upward extending passage extends fluidly intermediate of a vertically uppermost and radially outermost area of the separation chamber and the at least one axially centered fluid tight tube.

25. The apparatus according to claim 21
wherein the portion of the separation chamber that has the vertically truncated cone shape is immediately adjacent to the upper disc shape portion.

26. The apparatus according to claim 21
wherein the single use structure further includes
a cylindrical core in the interior area that extends vertically intermediate of the upper disc shape portion and the lower end,
wherein the portion of the separation chamber that has the vertically truncated cone shape extends radially between an outer surface of the cylindrical core and the continuous annular outer wall, and vertically immediately adjacent to the upper disc shape portion,
wherein the at least one axially centered fluid tight tube includes
a feed tube, wherein the feed tube is operative to cause cell culture to be delivered to the lower end, and
a centrate outlet tube, wherein the centrate outlet tube
is concentric with the feed tube, and
is operative to deliver cell centrate that has passed from the separation chamber through a cell centrate opening in the upper disc shape portion radially outward of the cylindrical core.

27. The apparatus according to claim 21
wherein the single use structure further includes
a cylindrical core that is in the interior area vertically intermediate of the upper disc shape portion and the lower end,
wherein the portion of the separation chamber that has the vertically truncated cone shape extends radially between an outer surface of the cylindrical core and the continuous annular outer wall, and vertically immediately adjacent to the upper disc shape portion,
wherein the upper disc shape portion includes
an axially centered concentrate chamber,
a concentrate centripetal pump in the axially centered concentrate chamber,
an axially centered centrate chamber,
a centrate centripetal pump in the axially centered centrate chamber,
wherein the axially centered centrate chamber extends vertically below the axially centered concentrate chamber,
wherein the at least one axially centered fluid tight tube is rotationally stationary during bowl rotation and includes
a feed tube, wherein the feed tube extends through each of the axially centered concentrate chamber and the axially centered centrate chamber, and is operative to cause cell culture to be delivered to the lower end,
a centrate outlet tube, wherein the centrate outlet tube
is concentric with the feed tube,
extends through the axially centered concentrate chamber,
is operative to receive cell centrate through the centrate centripetal pump, and
is operative to deliver cell centrate that has passed through a cell centrate opening in the upper disc shape portion, the axially centered cell centrate chamber, and the centrate centripetal pump,
wherein the cell centrate opening is open to the separation chamber radially outward from the outer surface of the cylindrical core,
a concentrate outlet tube, wherein the concentrate outlet tube,
is concentric with the feed tube,
is operative to receive cell concentrate through the concentrate centripetal pump,
is operative to deliver cell concentrate that has passed through a cell concentrate opening in the upper disc shape portion, the axially centered cell concentrate chamber and the concentrate centripetal pump, wherein the cell concentrate opening is open to the separation chamber
radially outward from the cylindrical core and the cell centrate opening, and
at a vertically uppermost and radially outermost area of the portion of the separation chamber that has the vertically truncated cone shape.

28. Apparatus comprising:
a multi-use rotatable centrifuge bowl,
wherein the centrifuge bowl is rotatable about a vertically extending axis, and includes a vertically extending axially centered cavity, wherein the vertically extending axially centered cavity has a larger radius in a cavity upper portion than in a cavity lower portion, a single use structure, wherein the single use structure
is removably positionable in the vertically extending axially centered cavity through the cavity upper portion, and
when positioned in the vertically extending axially centered cavity is rotatable in operative engagement with the centrifuge bowl,
wherein in an operative position the single use structure includes
an upper disc shape portion,
a continuous outer annular outer wall,
wherein the upper disc shape portion and the continuous outer annular wall are engaged in operative fluid tight relation and bound an interior area of the single use structure,
wherein the interior area of the single use structure includes a separation chamber,
wherein the separation chamber
it is bounded upwardly by the upper disc shape portion and radially by an inner surface of the continuous outer annular wall,
has a vertically truncated cone shape with a smaller inside radius adjacent to a lower end of the separation chamber that is disposed vertically away from the upper disc shape portion,
wherein rotation of the single use structure and the centrifuge bowl is operative to cause cell culture to be separated into cell centrate and cell concentrate in the separation chamber,
at least one vertically extending axially centered fluid tight tube, wherein
the at least one axially centered fluid tight tube
extends in the upper disc shape portion, and
is operative to deliver cell concentrate from an uppermost and radially outermost area of the separation chamber, out of the interior area of the single use structure.

* * * * *